(12) United States Patent
Butcher et al.

(10) Patent No.: US 6,692,922 B2
(45) Date of Patent: Feb. 17, 2004

(54) METHOD FOR IDENTIFYING AGENTS WHICH MODULATE CHEMOKINE "MEC"-INDUCED FUNCTIONS OF CCR3

(75) Inventors: Eugene C. Butcher, Portola Valley, CA (US); Eric J. Kunkel, Redwood City, CA (US); Junliang Pan, El Cerrito, CA (US); Dulce Soler-Ferrán, Watertown, MA (US)

(73) Assignees: The Board of Trustees of the Leland Stanford Junior University, Palo Alto, CA (US); Millennium Pharmaceuticals, Inc., Cambridge, MA (US)

( * ) Notice: Subject to any disclaimer, the term of this patent is extended or adjusted under 35 U.S.C. 154(b) by 78 days.

(21) Appl. No.: 09/931,381

(22) Filed: Aug. 15, 2001

(65) Prior Publication Data

US 2002/0137107 A1 Sep. 26, 2002

Related U.S. Application Data

(63) Continuation-in-part of application No. 09/638,914, filed on Aug. 15, 2000.

(51) Int. Cl.$^7$ .......................... G01N 33/53; C07K 17/00
(52) U.S. Cl. ......................................... 435/7.1; 530/350
(58) Field of Search ............................ 435/7.1; 530/350

(56) References Cited

U.S. PATENT DOCUMENTS 6,306,653 B1   10/2001   Papsidero et al. .......... 435/331

FOREIGN PATENT DOCUMENTS

| WO | WO 96/22371 | 6/1996 |
| WO | WO 97/21812 | 6/1997 |
| WO | WO 97/22698 | 6/1997 |
| WO | WO 98/23750 | 6/1998 |
| WO | WO 99/36540 | 7/1999 |
| WO | WO 00/38713 | 7/2000 |

OTHER PUBLICATIONS

Kunkel, et al., "Lymphocyte CC Chemokine Receptor 9 and Epithelial Thymus–Expressed Chemokine (TECK) Expression Distinguish the Small Intestinal Immune Compartment: Epithelial Expression of Tissue–Specific Chemokines as an Organizing Principle in Regional Immunity," *J. Exp. Med.* 192(5):761–767 (2000).
CCL28 Polyclonal Antibodies AF533 and BAF533, *de novo, New Products from R&D Systems*, pp. 5 and 7 (2001).
CCL28 Polyclonal Antibodies AF717 and BAF717, and CCL28 Monoclonal Antibody MAB717, *de novo, New Products from R&D Systems*, pp. 4 and 5 (2000).
Pan, J. et al., "Cutting Edge: A Novel Chemokine Ligand for CCR10 and CCR3 Expressed by Epithelial Cells in Mucosal Tissues," *J. Immunol.* 165:2943–2949 (2000).
Wang, W. et al., "Identification of a Novel Chemokine (CCL28), which Binds CCR10 (GPR2),"0 *J. Biol. Chem.* 275 (29):22313–22323 (2000).
Homey, B. et al., "Cutting Edge: the Orphan Chemokine Receptor G Protein–Coupled Receptor–2 (GPR–2, CCR10) Binds the Skin–Associated Chemokine CCL27 (CTACK/ALP/ILC)," *J. Immunol.* 164:3465–3470 (2000).
Gosling, J. et al., "Cutting Edge: Identification of a Novel Chemokine Receptor That Binds Dendritic Cell—and T Cell–Active Chemokines Including ELC, SLC, and TECK," *J. Immunol.* 164:2851–2856 (2000).
Daugherty, B.L. et al., "Cloning, Expression, and Characterization of the Human Eosinophil Eotaxin Receptor," *J. Exp. Med.* 183:2349–2354 (1996).
Ponath, P.D. et al., "Molecular Cloning and Characterization of a Human Eotaxin Receptor Expressed Selectively on Eosinophils," *J. Exp. Med.* 183:2437–2448 (1996).
Heath, H. et al., "Chemokine Receptor Usage by Human Eosinophils," *J. Clin. Invest.* 99 (2):178–184 (1997).
Forssmann, U. et al., "Eotaxin–2, a Novel CC Chemokine that is Selective for the Chemokine Receptor CCR3, and Acts Like Eotaxin on Human Eosinophil and Basophil Leukocytes," *J. Exp. Med.* 185 (12):2171–2176 (1997).
Kitaura, M. et al., "Molecular Cloning of Human Eotaxin, and Eosinophil–selective CC Chemokine, and Identification of a Specific Eosinophil Eotaxin Receptor, CC Chemokine Receptor 3," *J. Biol. Chem.* 271 (13):7725–7730 (1996).
Baggiolini, M. & Dahinden, C.A., "CC Chemokines in Allergic Inflammation," *Immunology Today* 15 (3):127–133 (1994).
Campbell, J.J. and Butcher, E.C., "Chemokines in Tissue–specific and Microenvironment–specific Lymphocyte Homing," *Current Opinion in Immunology* 12:336–341 (2000).
Bonini, J.A. & Steiner D.F., "Molecular Cloning and Expression of a Novel Rat CC–Chemokine Receptor (rCCR10rR) That Binds MCP–1 and MIP–1β with High Affinity," *DNA and Cell and Biology* 16 (9):1023–1030 (1997).
Miller, S.D. et al., "Periductal Mastitis— Masquerading as Carcinoma," *Dermatol. Surg.* 24:383–385 (1998).

(List continued on next page.)

*Primary Examiner*—Gary Kunz
*Assistant Examiner*—Sharon Turner
(74) *Attorney, Agent, or Firm*—Hamilton, Brook, Smith & Reynolds, P.C.

(57) ABSTRACT

The invention relates to the interaction of MEC with CCR3 and/or CCR10 and to agents (e.g., ligands, antibodies, antagonists, agonists, inhibitors, promoters) which alter said interaction. In one aspect, the invention relates to methods for detecting or identifying an agent (i.e., molecule or compound) which can modulate (inhibit, promote) the binding of MEC to CCR3 and/or CCR10. In another aspect, the invention relates to a method of treating a subject having an inflammatory condition, comprising administering to the subject an effective amount of an agent which modulates the binding of MEC to CCR3 and/or CCR10.

26 Claims, 25 Drawing Sheets

OTHER PUBLICATIONS

Bonini, J.A. et al., "Cloning, Expression, and Chromosomal Mapping of a Novel Human CC–Chemokine Receptor (CCR10) That Displays High–Affinity Binding for MCP–1 and MCP–3," *DNA and Cell Biology 16 (10)*:1249–1256 (1997).

Morales, J. et al., "CTACK, a Skin–associated Chemokine that Preferentially Attracts Skin–homing Memory T Cells," *Proc. Natl. Acad. Sci. USA 96 (25)*:14470–14475 (1999).

Jarmin, D.I. et al., "Cutting Edge: Identification of the Orphan Receptor G–Protein–Coupled Receptor 2 as CCR10, a Specific Receptor for the Chemokine ESkine,"*J. Immunol. 164*:3460–3464 (2000).

GenBank Accession No. NP_057686, (2000) "G Protein–coupled Receptor 2; CC Chemokine Receptor 10 [*Homo sapiens*]," [online], [retrieved onNov. 29, 2000]. Retrieved from the Internet: <URL:http://www.ncbi.nlm.nih.gov>.

GenBank Accession No. U86357, (1997) "*Mus Musculus* Chemokine (TECK) mRNA, Complete Cds," [online], [retrieved on Nov. 29, 2000]. Retrieved from the Internet: <URL:http://www.ncbi.nlm.nih.gov>.

GenBank Accession No. U86358, (1997) "Human Chemokine (TECK) mRNA, Complete Cds," [online], [retrieved on Nov. 29, 2000]. Retrieved from the Internet: <URL:http://www.ncbi.nlm.nih.gov>.

GenBank Accession No. AF201450, (1999) "*Danio rerio* CC Chemokine CCL1 (CCL1) mRNA, Complete Cds," [online], [retrieved on Nov. 29, 2000]. Retrieved from the Internet: <URL:http://www.ncbi.nlm.nih.gov>.

GenBank Accession No. AF082393, (1999) "*Homo sapiens* Skinkine mRNA, Complete Cds," [online], [retrieved on Nov. 29, 2000]. Retrieved from the Internet: <URL:http://www.ncbi.nlm.nih.gov>.

GenBank Accession No. AF082392, (1999) "*Mus musculus* Skinkine mRNA, Complete Cds," [online], [retrieved on Nov. 29, 2000]. Retrieved from the Internet: <URL:http://www.ncbi.nlm.nih.gov>.

GenBank Accession No. D86955, (1999) "*Homo sapiens* mRNA for CC Chemokine LARC Precursor, Complete Cds," [online], [retrieved on Nov. 29, 2000]. Retrieved from the Internet: <URL:http://www.ncbi.nlm.nih.gov>.

GenBank Accession No. NM_016602, (2000) "*Homo sapiens* G Protein–coupled Receptor 2 (GPR2), mRNA,"[online], [retrieved on Nov. 29, 2000]. Retrieved from the Internet: <URL:http://www.ncbi.nlm.nih.gov>.

GenBank Accession No. AAF72871, (2000) "7–Transmembrane G–Protein coupled Receptor 2 [*Homo sapiens*]," [online], [retrieved on Nov. 29, 2000]. Retrieved from the Internet: <URL:http://www.ncbi.nlm.nih.gov>.

GenBank Accession No. U94888, (2000) "*Homo sapiens* CC–Chemokine–binding Receptor JAB61 mRNA, Complete Cds," [online], [retrieved on Nov. 29, 2000]. Retrieved from the Internet: <URL:http://www.ncbi.nlm.nih.gov>.

GenBank Accession No. AF208237, (2000) "*Homo sapiens* 7–Transmembrane G–Protein coupled Receptor 2 (GPR2) mRNA, complete cds," [online], [retrieved on Nov. 29, 2000]. Retrieved from the Internet: <URL:http://www.ncbi.nlm.nih.gov>.

GenBank Accession No. U49727, (1996) "Human C-C Chemokine Receptor 3 (CKR–3) Gene, Complete Cds," [online], [retrieved on Nov. 29, 2000]. Retrieved from the Internet: <URL:http://www.ncbi.nlm.nih.gov>.

GenBank Accession No. AF266504, (2000) "*Homo sapiens* Mucosae–associated Epithelial Chemokine mRNA, Complete Cds," [online], [retrieved on Nov. 29, 2000]. Retrieved from the Internet: <URL:http://www.ncbi.nlm.nih.gov>.

Czinn, S.J., and Lamm, M.E., "Selective Chemotaxis of Subsets of B Lymphocytes from Gut–Associated Lymphoid Tissue and its Implications for the Recruitment of Mucosal Plasma Cells", *J. Immunol., 136(10)*:3607–3611 (1986).

Wehrli, N. et al., "Changing Responsiveness to Chemokines Allows Medullary Plasmablasts to Leave Lymph Nodes", *Eur. J. Immunol., 31(2)*:609–616 (2001).

Curtis, J.L. et al., "Adhesion Receptor Phenotypes of Murine Lung CD4+ T Cells During the Pulmonary Immune Response to Sheep Erythrocytes", *Am. J. Respir. Cell Mol. Biol., 12(5)*:520–530 (1995).

Ishikawa–Mochizuki, I. et al., "Molecular Cloning of a Novel CC Chemokine, Interleukin–11 Receptor a–Locus Chemokine (ILC), Which is Located on Chromosome 9p13 and a Potential Homologue of a CC Chemokine Encoded by Molluscum contagiosum Virus", *FEBS Letters, 460*:544–548, (1999).

Hargreaves, D.C. et al., "A Coordinated Change in Chemokine Responsiveness Guides Plasma Cell Movements", *J. Exp. Med., 194(1)*:45–56 (2001).

Biotinylated Anti–human CCL28 Antibody. R&D Systems (2000).

FIG. 1A

```
  1  tgatcgaacagcctcacttgtgttgctgtcagtgccagtaggcaggcaggaatgcagca   60
                                                          M  Q  Q
 61  gagaggactcgccatcgtgctggcctgctgtgcggccctacatgcctcagaagccat   120
      R  G  L  A  I  V  A  L  A  V  C  A  A  L  H  A  S  E  A  I
121  acttcccattgcctccagctgttgcacgtgttgcacatcatattccagaaggctcct   180
      L  P  I  A  S  C  C  T  E  V  S  H  H  I  S  R  R  L  L
181  ggaaagagtgaataatgtgtcgcatccagagagctgatggggattgtgactggctgtgt   240
      E  R  V  N  M  C  R  I  Q  R  A  D  G  D  C  D  L  A  A  V
241  catcctcatgtcaagcgcaagtcgtcagcgaagaatctgtgtcagccatactgttaagca   300
      I  L  H  V  K  R  R  R  I  C  V  S  P  H  N  H  T  V  K  Q
301  gtggatgaaagtgcaagtgccaagaaaaatggtaaagaatgtttgccacaggaagaa   360
      W  M  K  V  Q  A  A  K  K  N  G  K  G  N  V  C  H  R  K  K
361  acaccatggcaagagaggaacagtgaacaggcacatcaggggaaacacgaaacatacggcca   420
      H  H  G  K  R  N  S  N  R  A  H  Q  G  K  H  E  T  Y  G  H
421  taaaactccttattagagagtctacagataaatctacagagacaattcctcaagtggact   480
      K  T  P  Y  *
481  tggccatgattggttcctgcatactgatgaactactgatgtcagctggtctgaagga   540
541  ccctaccagaagctaaatcatcaaagaatgcaatttccatatcctaatgattcaatctcc   600
601  cttaccctgaccaatcagtggcccaatttccagcccccttgcctcccagaacccagcc   660
661  cagaactcttcagagatttaagaatctcctcctacctcctgactcagcaccatgtaatca   720
721  ttaaactctctgctgcaaaaaaaaaaaaaaaaaaaaaaaaaaaaaaaaa   768
```

Chromosome 5
CTD2282F8

| Exon | Location in cDNA | Length in bp | Sequence at intron-exon junction | | Intron Length in bp |
|---|---|---|---|---|---|
| | | | 3' splice site | 5' splice site | |
| I | 1-116 | 116 | | TGATCGAA--CTCAGAAGgtgagtgg... (SEQ ID NO:3) | >22,000 |
| II | 117-243 | 127 | ..tcttttagCCATACTT--GCTGTCATgtgagtgc... (SEQ ID NO:5) | (SEQ ID NO:4) (SEQ ID NO:6) | 6296 |
| III | 244-495 | 252 | ..tctaacagCCTTCATG--GATTGGTTgtaagttt... (SEQ ID NO:7) | (SEQ ID NO:8) | 4857 |
| IV | 496-739 | 244 | ..tctttcagGTCCTGCA--GCTGCAAA (SEQ ID NO:9) | (SEQ ID NO:10) | |

FIG. 1C

```
hMEC    --ILPIASSCCTEVSHH-ISRRLIERVNMCRIQRADGDCDLAAVILHVKRR--RICVSPHN
hCTACK  FLLPPSTACCTQLYRKPLSDKLLRKVIQVELQEADGDCHLQAFVLHLAQR--SICIHPQN
mCTACK  LPLPSSTSCCTQLYRQPLPSRLLRRIVHMELQEADGDCHLQAVVLHLARR--SVCVHPQN
hTECK   --QGVFEDCCLAYHYP-IGWAVLRRAWTYRIQEVSGSCNLPAAIFYLPKRHRKV--CGNPKS
mTECK   --QGAFEDCCLGYQHR-IKWNVLRHARNYHQQEVSGSCNLRAVRFYFRQK--VVCGNPED hMEC    HTVKQWMKVQAAKKNG---KGNVCHRKKHHGKRNSNRAHQGKHETYGHKTPY--------
hCTACK  PSLSQWFEHQERKLHGTLPKLNFGMLRKMG-------------------------------
mCTACK  RSLARWLERQGKRLQGTVPSINLVLQKKMYSNPQQQN------------------------
hTECK   REVQRAMKLLDARNKV-FAKLHHNMQTFQAGPHAVKKLSSGNSKLSSSKFSNPISSSKRN
mTECK   MNVKRAIRILTARKRLVHWKSASDSQTERKKSNHMKSKVENPNSTSVRSATLGHPRMVMM hMEC    -----------
hCTACK  -----------
mCTACK  -----------
hTECK   VSLLISANSGL
mTECK   PRKTNN-----
```

FIG. 3B

| | | | | | | | | | | | |
|---|---|---|---|---|---|---|---|---|---|---|---|
| whole brain | cerebellum, left | substania nigra | heart | esophagus | colon transverse | kidney | lung | liver | Leukemia, HL-60 | fetal brain | yeast total RNA |
| cerebral cortex | cerebellum, right | accumbens nucleus | aorta | stomach | colon descending | skeletal muscle | placenta | pancreas | HeLa S3 | fetal heart | yeast tRNA |
| frontal lobe | corpus callosum | thalamus | atrium, left | duodenum | rectum | spleen | bladder | adrenal gland | Leukemia, K-562 | fetal kidney | E. coli rRna |
| parietal lobe | amygdala | pituitary gland | atrium, right | jejunum | | thymus | uterus | thyroid gland | Leukemia, MOLT-4 | fetal liver | E. coli DNA |
| occipital lobe | caudate nucleus | spinal cord | ventricle, left | ileum | | peripheral blood leukocyte | prostate | salivary gland | Burkitt's lymphoma, Raji | fetal spleen | Poly r(A) |
| temporal lobe | hippo-campus | | ventricle, right | ilocecum | | lymph node | testis | mammary gland | Burkitt's lymphomas, Daudi | fetal thymus | human $C_0t$-1 DNA |
| paracentral gyrus of cerebral cortex | medulla oblongata | | inter-ventricular septum | appendix | | bone marrow | ovary | | colorectal adeno-carcinoma, SW480 | fetal lung | human DNA 100 ng |
| pons | putamen | | apex of the heart | colon ascending | | trachea | | | lung carcinoma, A549 | | human DNA 500 ng |

```
  1  aatccttttc ctggcacctc tgatatcctt ttgaaattca tgttaaagaa tccctaggct
 61  gctatcacat gtggcatctt tgttgagtac atgaataaat caactggtgt gttttacgga
121  ggatgattat gcttcattgt gggattgtat ttttcttctt ctatcacagg gagaagtgaa
181  atgacaacct cactagatac agttgagacc tttggtacca catcctacta tgatgacgtg
241  ggcctgctct gtgaaaaagc tgataccaga gcactgatgg cccagtttgt gccccgctg
301  tactccctgg tgttcactgt gggcctcttg ggcaatgtgg tggtgtgat gatcctcata
361  aaatacagga ggctccgaat tatgaccaac atctacctgc tcaacctgc catttcggac
421  ctgctcttcc tcgtcaccct tccattctgg tccactatg atccactatg taactgggtt
481  tttggccatg gcatgtgtaa gctcctctca gggttttatc acacaggctt gtacagcgag
541  atctttttca taatcctgct gacaatcgac aggtacctgg ccattgtcca tgctgtgttt
601  gcccttcgag cccgactgt cacttttggt gtcatcacca ccattgtcac ctgggcctg
661  gcagtgctag cagtcttcc tgaatttatc ttctatgaga ctgaagagtt gttgaagag
721  actctttgca gtgctcttta cccagaggat acagtatata gctggagca tttccacact
781  ctgagaatga ccatctctg tctcgttctc cctctgctcg ttatgccat ctgctacaca
841  ggaatcatca aaacgctgct gaggtgcccc agtaaaaaaa agtacaaggc catccggctc
901  attttgtca tcatggcggt gtttttcatt ttctggacac cctacaatgt ggctatcctt
961  ctctcttcct atcaatccat cttatttgga aatgactgtg agcggacgaa gcatctggac
```

FIG. 4A

```
1021 ctggtcatgc tggtgacaga ggtgatcgcc tactcccact gctgcatgaa cccggtgatc
1081 tacgcctttg ttggagagag gttccggaag tacctgcgcc acttcttcca caggcacttg
1141 ctcatgcacc tgggcagata catcccattc cttcctagtg agaagctgga aagaaccagc
1201 tctgtctctc catccacagc agagccggaa ctctctattg tgttttaggt agatgcagaa
1261 aattgcctaa agaggaagga ccaaggagat naagcaaaca cattaagcct tccacactca
1321 cctctaaaac agtccttcaa accttccagt gcaacactga agctcttaag acactgaaat
1381 atacacacag cagtagcagt agatgcatgt accctaaggt cattaccaca ggccagggct
1441 gggcagcgta ctcatcatca acctaaaaag cagagctttg cttctctctc taaaatgagt
1501 tacctatatt ttaatgcacc tgaatgttag atagttacta tatgccgcta caaaaaggta
1561 aaacttttta tattttatac attaacttca gccagctatt atataaataa aacattttca
1621 cacaatacaa taagttaact atttattttt ctaatgtgcc tagttctttc cctgcttaat
1681 gaaaagctt
```

FIG. 4B

```
  1 mttsldtvet fgttsyyddv glicekadtr almaqfvppl yslvftvgll gnvvvmili
 61 kyrrlrimtn iylnlaisd llflvtlpfw ihyvrghnwv fghgmcklls gfyhtglyse
121 iffilltid rylaivhavf alrartvtfg vitsivtwgl avlaalpefi fyeteelfee
181 tlcsalyped tvyswrhfht lrmtifclvl pllvmaicyt giiktllrcp skkkykairl
241 ifvimavffi fwtpynvail lssyqsilfg ndcertkhld lvmlvtevia yshccmnpvi
301 yafvgerfrk ylrhffhrhl lmhlgryipf lpseklerts svspstaepe lsivf
```

FIG. 5

```
  1 agagatgggg acggaggcca cagagcaggt ttcctggggc cattactctg gggatgaaga
 61 ggacgcatac tcggctgagc cactgccgga gctttgctac aaggccgatg tccaggcctt
121 cagccgggcc ttccaaccca gtgtctccct gaccgtggct gcgctgggtc tggccggcaa
181 tggcctggtc ctggccaccc acctggcagc ccgacgcgca gcgcgtcgc ccacctctgc
241 ccacctgctc cagctggccc cagctggcct cttgctggcc ctgactctgc ccttcgcggc
301 agcagggct cttcagggct ggagtctggg aagtgccacc tgccgcacca tctctggcct
361 ctactcggcc tccttccacg ccggcttcct cttcctggcc tgtatcagcg ccgaccgcta
421 cgtggccatc gcgcgagcgc gtcatcgtgt ggctgctgtc tccactcccg gcgctgctt
481 cttggtctcc gtcatcgtgt ggctgctgtc actgctctg gcgctgcctg cgctgctctt
541 cagccaggat gggcagcggg aaggccaacg acgctgtcgc ctcatcttcc ccgagggcct
601 cacgcagacg gtgaaggggg cgagcgccgt ggcgcaggtg gccctgggct tcgcgctgcc
661 gctgggcgtc atggtagcct gctacgcgct tctgggccgc acgctgctgg ccgccagggg
721 gcccgagcgc cggcgtgcgc tgcgcgtcgt ggtggtctg gtggccgcct tcgtggtgct
781 gcagctgccc tacagcctcg cccctgctgct ggatactgcc gatctactgc ctgcgcga
```

FIG. 6A

```
 841  gcggagctgc  cctgccagca  aacgcaagga  tgtcgcactg  ctggtgacca  gcggcttggc
 901  cctcgcccgc  tgtggcctca  atcccgttct  ctacgccttc  ctgggcctgc  gcttccgcca
 961  ggacctgcgg  aggctgctac  ggggtggggag  ctcgccctca  gggcctcaac  cccgccgcgg
1021  ctgcccccgc  cggcccccgcc  tttcttcctg  ctcagctccc  acggagaccc  acagtctctc
1081  ctgggacaaac  tagggctgcg  aatctagagg  aggggggcagg  ctgagggtcg  tgggaaaggg
1141  gagtaggtgg  gggacactg  agaaagaggc  agggacctaa  agggactacc  tctgtgcctt
1201  gccacattaa  attgataaca  tggaaatgaa  aaaaaaaaaa  aaaa
```

FIG. 6B

```
  1 mgteateqvs wghysgdeed aysaeplpel cykadvqafs rafqpsvslt vaalglagng
 61 lvlathlaar raarsptsah llqlaladll laltlpfaaa galqgwslgs atcrtisgly
121 sasfhagflf lacisadryv aiaralpagp rpstpgrahl vsvivwllsl llalpallfs
181 qdgqreggrr crlifpeglt qtvkgasava qvalgfalpl gvmvacyall grtllaargp
241 errralrvvv alvaafvvlq lpyslallld tadllaarer scpaskrkdv allvtsglal
301 arcglnpvly aflglrfrqd lrrllrggss psgpqprrgc prrprlsscs aptethslsw
361 dn
```

FIG. 7

```
  1 atgggacgg aggccacaga gcaggtttcc tgggccatt actctgggga tgaagaggac
 61 gcatactcgg ctgagccact gccggagctt tgctacaagg ccgatgtcca ggccttcagc
121 cgggccttcc aacccagtgt ctccctgacc gtggctgcgc tgggtctggc cggcaatggc
181 ctggtcctgg ccacccacct ggcagcccga cgcgcagcgc gctcgcccac ctctgcccac
241 ctgctccagc tggccctggc cgacctcttg ctggccctga ctctgccctt cgcggcagca
301 gggctcttc agggtggag tctgggaagt cttcctcttc gccacctgcc gcaccatctc tggctctac
361 tcggcctcct tccacgccgg cttcctcttc ctgcctgta tcagcgccga ccgctacgtg
421 gccatcgcgc gagcgctccc agccgggccg ctccctggcg ctcctcccgg cgcacacttg
481 gtctccgtca tcgtgtggct gctgtcactg cccctggcgc tgcctgcgct gtctcttcagc
541 caggatgggc agcgggaagg ccaacgacgc tgtcgcctca tcttcccga gggcctcacg
601 cagacggtga aggggcgag cgccgtggcg caggtggccc tgggcttcgc gctgccgctg
661 ggcgtcatgg tagcctgcta cgcgcttctg ggccgcacgc tggccgccag ggggcccgag
721 cgccggcgtg cgctgcgcgt cgtggtggct ctggtggcgg ccttcgtggt gctcgtgcag
781 ccctacagcc tgcccctgct gctggatact gccgatctac tggctgcgcg cgagcggagc
```

FIG. 8A

```
 841  tgccctgcca gcaaacgcaa ggatgtcgca ctgctggtga ccagcggctt ggccctcgcc
 901  cgctgtggcc tcaatcccgt tctctacgcc ttcctgggcc tgcgcttccg ccaggacctg
 961  cggaggctgc tacggggtgg gagctgcccc tcagggcctc aacccgcgcg cggctgcccc
1021  cgccggcccc gcctttcttc ctgctcagct cccacggaga cccacagtct ctcctgggac
1081  aactag
```

FIG. 8B

```
  1 mgteateqvs wghysgdeed aysaeplpel cykadvgafs rafqpsvslt vaalglagng
 61 lvlathlaar raarsptsah llqlaladll laltlpfaaa galqgwslgs atcrtisgly
121 sasfhagflf lacisadryv aiaralpagp rpstpgrahl vsvivwllsl llalpallfs
181 qdgqreggrr crlifpeglt qtvkgasava qvalgfalpl gvmvacyall grtlaargpe
241 rrralrvvva lvaafvvlql pyslalldt adllaarers cpaskrkdva llvtsglala
301 rcglnpvlya flglrfrqdl rrllrggscp sgpqprrgcp rrprlsscsa ptethslswd
361 n
```

FIG. 9

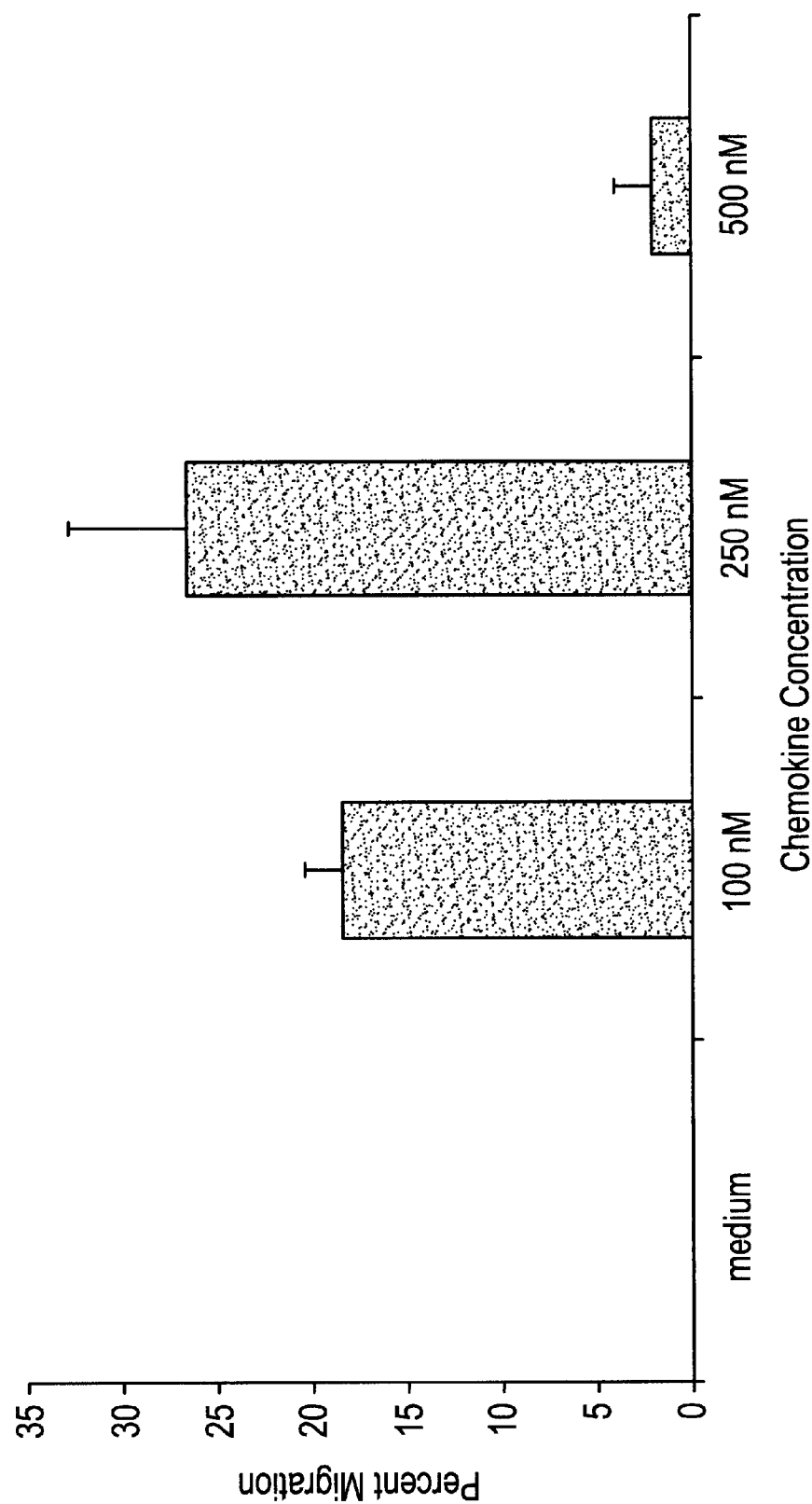

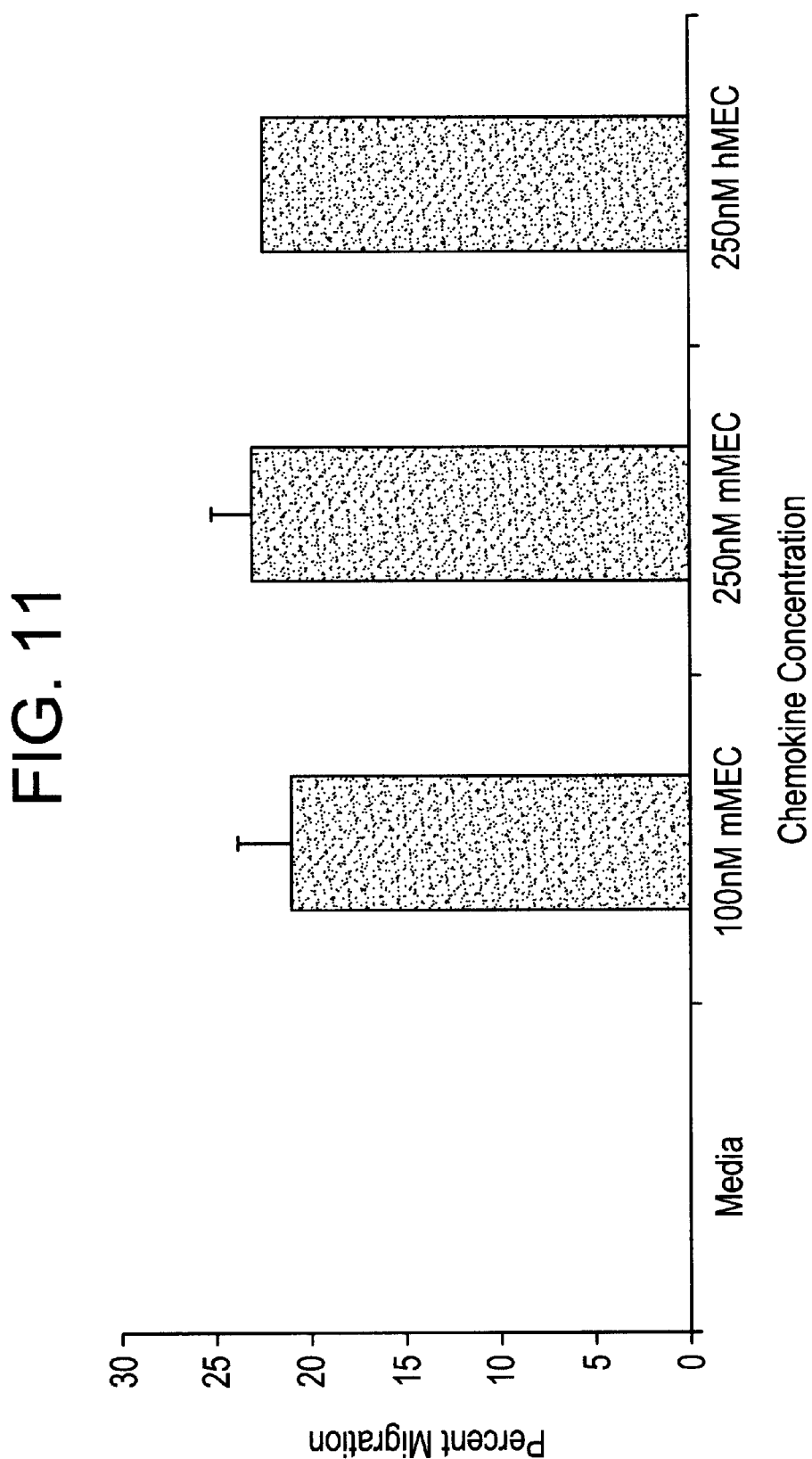

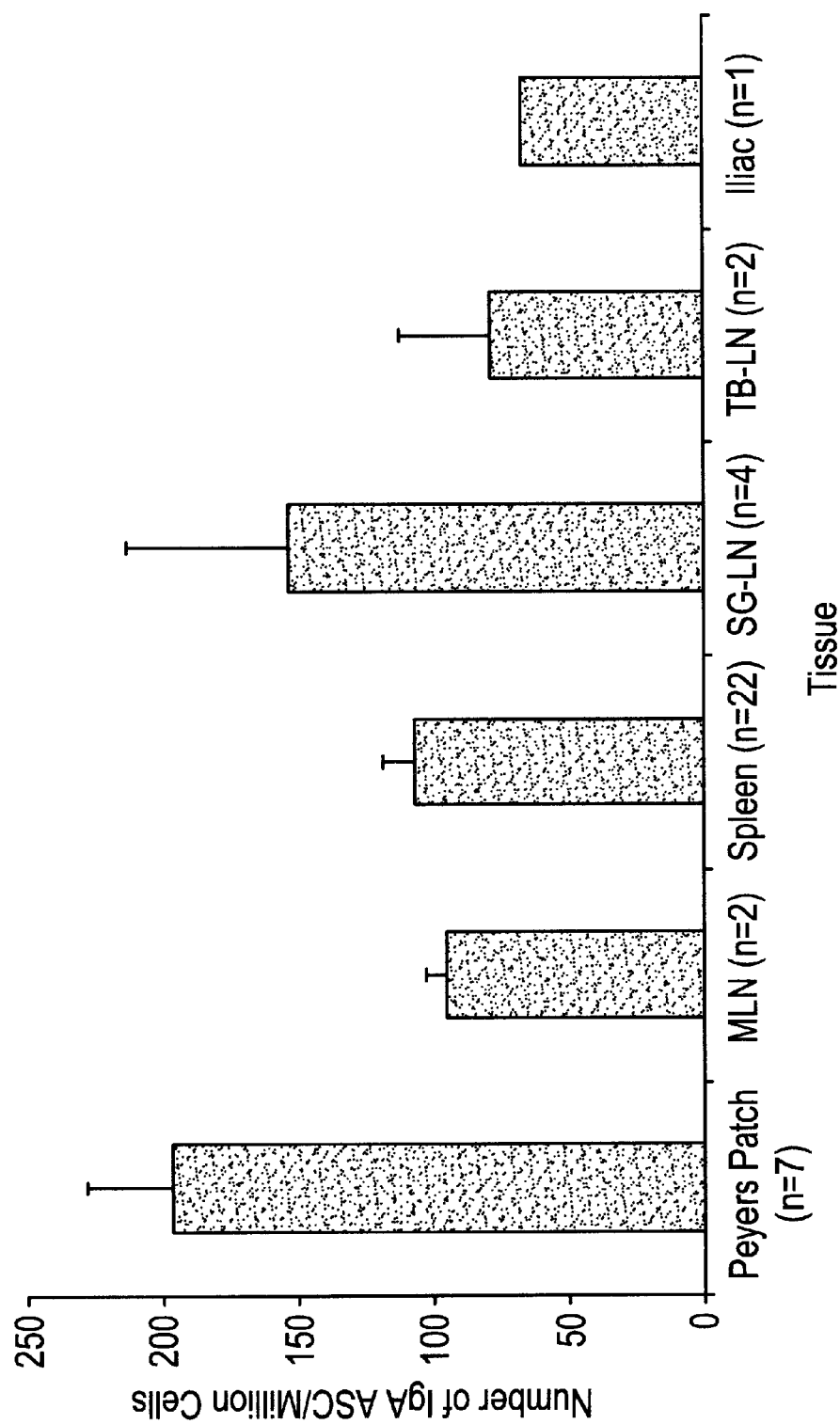

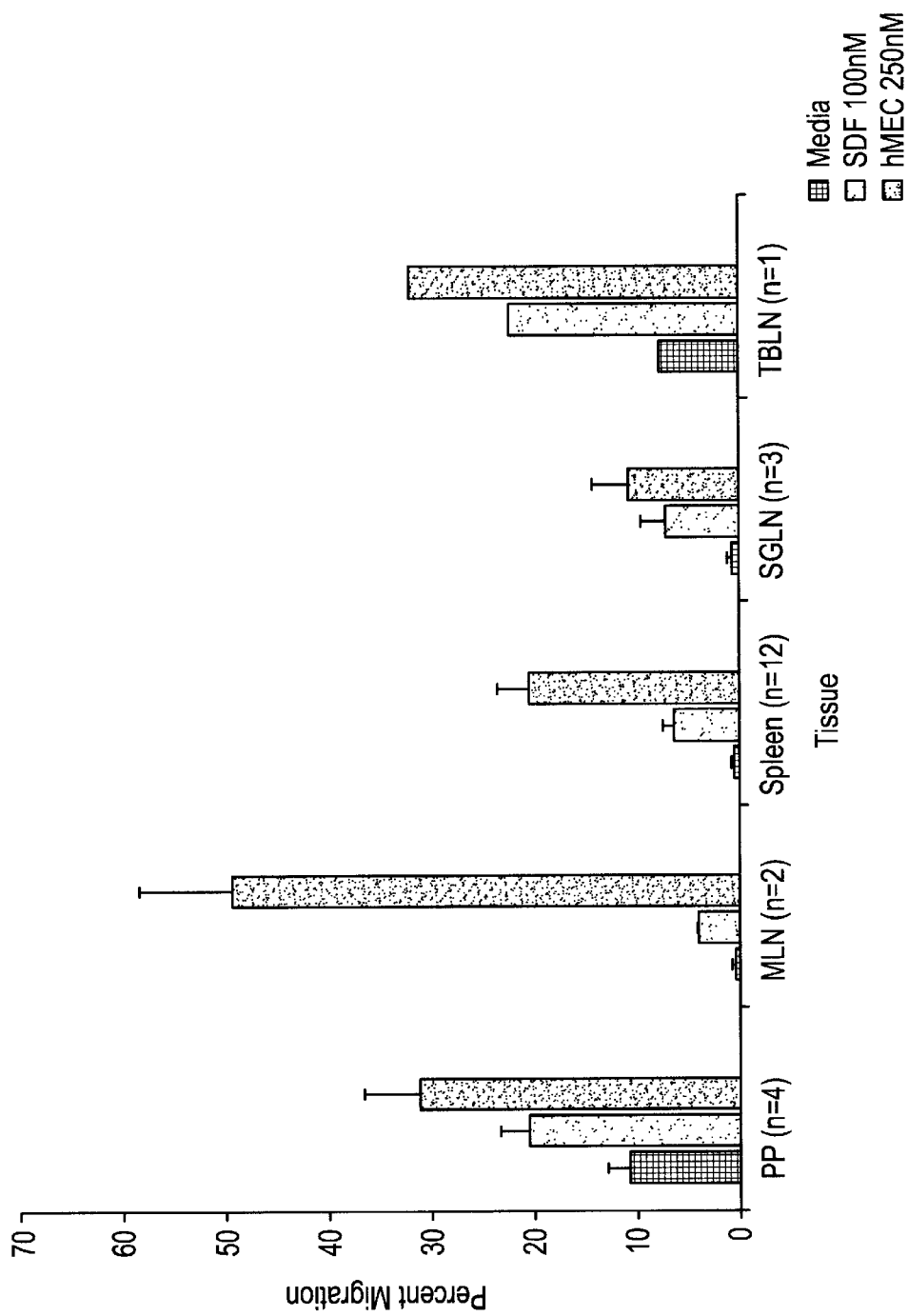

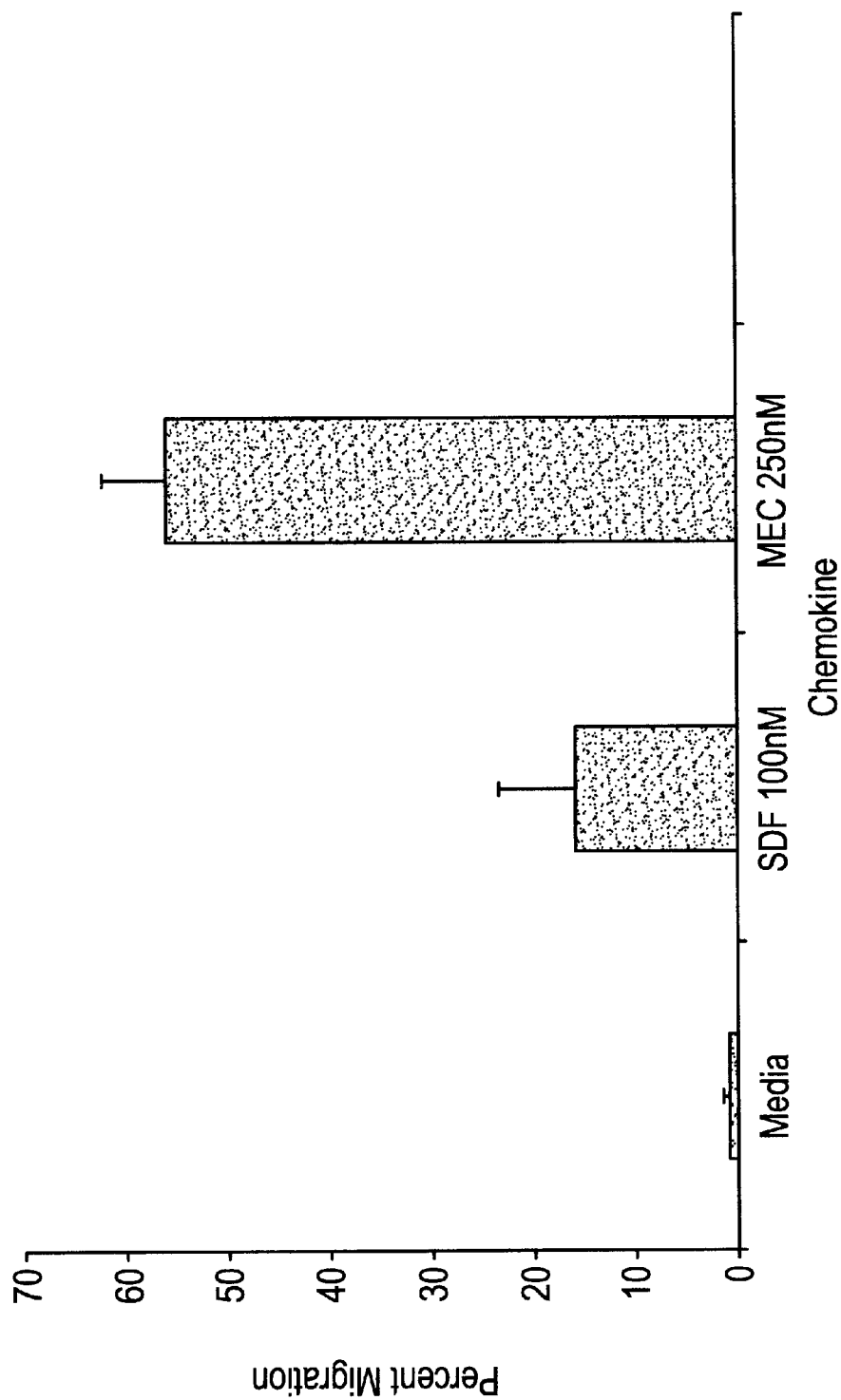

SEQUENCE LISTING

```
<160> NUMBER OF SEQ ID NOS: 24

<210> SEQ ID NO 1
<211> LENGTH: 768
<212> TYPE: DNA
<213> ORGANISM: Homo sapiens
<220> FEATURE:
<221> NAME/KEY: CDS
<222> LOCATION: (53)...(436)

<400> SEQUENCE: 1
tgatcgaaca gcctcacttg tgttgctgtc agtgccagta gggcaggcag ga atg cag         58
                                                          Met Gln
                                                            1 cag aga gga ctc gcc atc gtg gcc ttg gct gtc tgt gcg gcc cta cat         106
Gln Arg Gly Leu Ala Ile Val Ala Leu Ala Val Cys Ala Ala Leu His
         5                  10                  15 gcc tca gaa gcc ata ctt ccc att gcc tcc agc tgt tgc acg gag gtt         154
Ala Ser Glu Ala Ile Leu Pro Ile Ala Ser Ser Cys Cys Thr Glu Val
     20                  25                  30 tca cat cat att tcc aga agg ctc ctg gaa aga gtg aat atg tgt cgc         202
Ser His His Ile Ser Arg Arg Leu Leu Glu Arg Val Asn Met Cys Arg
 35                  40                  45                  50 atc cag aga gct gat ggg gat tgt gac ttg gct gct gtc atc ctt cat         250
Ile Gln Arg Ala Asp Gly Asp Cys Asp Leu Ala Ala Val Ile Leu His
                 55                  60                  65 gtc aag cgc aga aga atc tgt gtc agc ccg cac aac cat act gtt aag         298
Val Lys Arg Arg Arg Ile Cys Val Ser Pro His Asn His Thr Val Lys
             70                  75                  80 cag tgg atg aaa gtg caa gct gcc aag aaa aat ggt aaa gga aat gtt         346
Gln Trp Met Lys Val Gln Ala Ala Lys Lys Asn Gly Lys Gly Asn Val
         85                  90                  95 tgc cac agg aag aaa cac cat ggc aag agg aac agt aac agg gca cat         394
Cys His Arg Lys Lys His His Gly Lys Arg Asn Ser Asn Arg Ala His
    100                 105                 110 cag ggg aaa cac gaa aca tac ggc cat aaa act cct tat tag              436
Gln Gly Lys His Glu Thr Tyr Gly His Lys Thr Pro Tyr *
115                 120                 125 agagtctaca gataaatcta cagagacaat tcctcaagtg gacttggcca tgattggttg         496
tcctgcatac tgatgaaact actgatgtca gctggtctga aggaccctac cagaagctaa         556
atcatcaaag aatgcaattt ccatatccta atgattcaat ctcccttacc ctgaccaatc         616
agtggcccaa attttccagc cccttgcctc ccagaacccc agcccagaac tcttcagaga         676
tttaagaatc tcctcctacc tcctgactca gcaccatgta atcattaaac tctctgctgc         736
aaaaaaaaaa aaaaaaaaa aaaaaaaaa aa                                        768

<210> SEQ ID NO 2
<211> LENGTH: 127
<212> TYPE: PRT
```

```
<213> ORGANISM: Homo sapiens
<220> FEATURE:
<221> NAME/KEY: SIGNAL
<222> LOCATION: (1)...(22)

<400> SEQUENCE: 2

Met Gln Gln Arg Gly Leu Ala Ile Val Ala Leu Ala Val Cys Ala Ala
        -20                 -15                 -10
Leu His Ala Ser Glu Ala Ile Leu Pro Ile Ala Ser Ser Cys Cys Thr
     -5                   1               5                   10
Glu Val Ser His His Ile Ser Arg Arg Leu Leu Glu Arg Val Asn Met
                15                  20                  25
Cys Arg Ile Gln Arg Ala Asp Gly Asp Cys Asp Leu Ala Ala Val Ile
            30                  35                  40
Leu His Val Lys Arg Arg Arg Ile Cys Val Ser Pro His Asn His Thr
            45                  50                  55
Val Lys Gln Trp Met Lys Val Gln Ala Ala Lys Lys Asn Gly Lys Gly
        60                  65                  70
Asn Val Cys His Arg Lys Lys His Gly Lys Arg Asn Ser Asn Arg
75                  80                  85                  90
Ala His Gln Gly Lys His Glu Thr Tyr Gly His Lys Thr Pro Tyr
                95                  100                 105

<210> SEQ ID NO 3
<211> LENGTH: 8
<212> TYPE: DNA
<213> ORGANISM: Homo sapiens
<220> FEATURE:
<221> NAME/KEY: exon
<222> LOCATION: (1)...(8)

<400> SEQUENCE: 3 tgatcgaa                                                                 8

<210> SEQ ID NO 4
<211> LENGTH: 16
<212> TYPE: DNA
<213> ORGANISM: Homo sapiens
<220> FEATURE:
<221> NAME/KEY: exon
<222> LOCATION: (1)...(8)
<221> NAME/KEY: intron
<222> LOCATION: (9)...(16)

<400> SEQUENCE: 4
ctcagaaggt gagtgg                                                        16

<210> SEQ ID NO 5
<211> LENGTH: 16
<212> TYPE: DNA
<213> ORGANISM: Homo sapiens
<220> FEATURE:
<221> NAME/KEY: intron
<222> LOCATION: (1)...(8)
<221> NAME/KEY: exon
<222> LOCATION: (9)...(16)

<400> SEQUENCE: 5
tcttttagcc atactt                                                        16

<210> SEQ ID NO 6
<211> LENGTH: 16
<212> TYPE: DNA
<213> ORGANISM: Homo sapiens
```

-continued

```
<220> FEATURE:
<221> NAME/KEY: exon
<222> LOCATION: (1)...(8)
<221> NAME/KEY: intron
<222> LOCATION: (9)...(16)
<223> OTHER INFORMATION: 16

<400> SEQUENCE: 6
gctgtcatgt gagtgc                                                              16

<210> SEQ ID NO 7
<211> LENGTH: 16
<212> TYPE: DNA
<213> ORGANISM: Homo sapiens
<220> FEATURE:
<221> NAME/KEY: intron
<222> LOCATION: (1)...(8)
<221> NAME/KEY: exon
<222> LOCATION: (9)...(16)
<223> OTHER INFORMATION: 16

<400> SEQUENCE: 7
tctaacagcc ttcatg                                                              16

<210> SEQ ID NO 8
<211> LENGTH: 16
<212> TYPE: DNA
<213> ORGANISM: Homo sapiens
<220> FEATURE:
<221> NAME/KEY: exon
<222> LOCATION: (1)...(8)
<221> NAME/KEY: intron
<222> LOCATION: (9)...(16)

<400> SEQUENCE: 8
gattggttgt aagttt                                                              16

<210> SEQ ID NO 9
<211> LENGTH: 16
<212> TYPE: DNA
<213> ORGANISM: Homo sapiens
<220> FEATURE:
<221> NAME/KEY: intron
<222> LOCATION: (1)...(8)
<221> NAME/KEY: exon
<222> LOCATION: (9)...(16)

<400> SEQUENCE: 9
tctttcaggt cctgca                                                              16

<210> SEQ ID NO 10
<211> LENGTH: 8
<212> TYPE: DNA
<213> ORGANISM: Homo sapiens
<220> FEATURE:
<221> NAME/KEY: exon
<222> LOCATION: (1)...(8)

<400> SEQUENCE: 10 gctgcaaa                                                                        8

<210> SEQ ID NO 11
<211> LENGTH: 112
<212> TYPE: PRT
<213> ORGANISM: Homo sapiens

<400> SEQUENCE: 11

Met Lys Gly Pro Pro Thr Phe Cys Ser Leu Leu Leu Leu Ser Leu Leu
```

-continued

```
                1               5                      10                        15
Leu Ser Pro Asp Pro Thr Ala Ala Phe Leu Leu Pro Pro Ser Thr Ala
                20                      25                      30

Cys Cys Thr Gln Leu Tyr Arg Lys Pro Leu Ser Asp Lys Leu Leu Arg
            35                      40                      45

Lys Val Ile Gln Val Glu Leu Gln Glu Ala Asp Gly Asp Cys His Leu
        50                      55                      60

Gln Ala Phe Val Leu His Leu Ala Gln Arg Ser Ile Cys Ile His Pro
65                      70                      75                      80

Gln Asn Pro Ser Leu Ser Gln Trp Phe Glu His Gln Glu Arg Lys Leu
                85                      90                      95

His Gly Thr Leu Pro Lys Leu Asn Phe Gly Met Leu Arg Lys Met Gly
                100                     105                     110
```

<210> SEQ ID NO 12
<211> LENGTH: 120
<212> TYPE: PRT
<213> ORGANISM: Mus musculus

<400> SEQUENCE: 12

```
Met Met Glu Gly Leu Ser Pro Ala Ser Ser Leu Pro Leu Leu Leu Leu
1               5                       10                      15

Leu Leu Ser Pro Ala Pro Glu Ala Ala Leu Pro Leu Pro Ser Ser Thr
                20                      25                      30

Ser Cys Cys Thr Gln Leu Tyr Arg Gln Pro Leu Pro Ser Arg Leu Leu
            35                      40                      45

Arg Arg Ile Val His Met Glu Leu Gln Glu Ala Asp Gly Asp Cys His
        50                      55                      60

Leu Gln Ala Val Val Leu His Leu Ala Arg Arg Ser Val Cys Val His
65                      70                      75                      80

Pro Gln Asn Arg Ser Leu Ala Arg Trp Leu Glu Arg Gln Gly Lys Arg
                85                      90                      95

Leu Gln Gly Thr Val Pro Ser Leu Asn Leu Val Leu Gln Lys Lys Met
                100                     105                     110

Tyr Ser Asn Pro Gln Gln Gln Asn
            115                     120
```

<210> SEQ ID NO 13
<211> LENGTH: 150
<212> TYPE: PRT
<213> ORGANISM: Homo sapiens

<400> SEQUENCE: 13

```
Met Asn Leu Trp Leu Leu Ala Cys Leu Val Ala Gly Phe Leu Gly Ala
1               5                       10                      15

Trp Ala Pro Ala Val His Thr Gln Gly Val Phe Glu Asp Cys Cys Leu
                20                      25                      30

Ala Tyr His Tyr Pro Ile Gly Trp Ala Val Leu Arg Arg Ala Trp Thr
            35                      40                      45

Tyr Arg Ile Gln Glu Val Ser Gly Ser Cys Asn Leu Pro Ala Ala Ile
        50                      55                      60

Phe Tyr Leu Pro Lys Arg His Arg Lys Val Cys Gly Asn Pro Lys Ser
65                      70                      75                      80

Arg Glu Val Gln Arg Ala Met Lys Leu Leu Asp Ala Arg Asn Lys Val
                85                      90                      95

Phe Ala Lys Leu His His Asn Met Gln Thr Phe Gln Ala Gly Pro His
```

```
                    100                 105                 110
Ala Val Lys Lys Leu Ser Ser Gly Asn Ser Lys Leu Ser Ser Ser Lys
            115                 120                 125

Phe Ser Asn Pro Ile Ser Ser Lys Arg Asn Val Ser Leu Leu Ile
        130                 135                 140

Ser Ala Asn Ser Gly Leu
145                 150

<210> SEQ ID NO 14
<211> LENGTH: 144
<212> TYPE: PRT
<213> ORGANISM: Mus musculus

<400> SEQUENCE: 14

Met Lys Leu Trp Leu Phe Ala Cys Leu Val Ala Cys Phe Val Gly Ala
 1               5                  10                  15

Trp Met Pro Val Val His Ala Gln Gly Ala Phe Glu Asp Cys Cys Leu
            20                  25                  30

Gly Tyr Gln His Arg Ile Lys Trp Asn Val Leu Arg His Ala Arg Asn
        35                  40                  45

Tyr His Gln Gln Glu Val Ser Gly Ser Cys Asn Leu Arg Ala Val Arg
    50                  55                  60

Phe Tyr Phe Arg Gln Lys Val Val Cys Gly Asn Pro Glu Asp Met Asn
65                  70                  75                  80

Val Lys Arg Ala Ile Arg Ile Leu Thr Ala Arg Lys Arg Leu Val His
                85                  90                  95

Trp Lys Ser Ala Ser Asp Ser Gln Thr Glu Arg Lys Lys Ser Asn His
            100                 105                 110

Met Lys Ser Lys Val Glu Asn Pro Asn Ser Thr Ser Val Arg Ser Ala
        115                 120                 125

Thr Leu Gly His Pro Arg Met Val Met Met Pro Arg Lys Thr Asn Asn
    130                 135                 140

<210> SEQ ID NO 15
<211> LENGTH: 1689
<212> TYPE: DNA
<213> ORGANISM: Homo sapiens
<220> FEATURE:
<221> NAME/KEY: CDS
<222> LOCATION: (181)...(1248)
<221> NAME/KEY: misc_feature
<222> LOCATION: (1291)...(1291)
<223> OTHER INFORMATION: n = A, T, C or G

<400> SEQUENCE: 15 aatcctttc  ctggcacctc  tgatatcctt  ttgaaattca  tgttaaagaa  tccctaggct      60
gctatcacat  gtggcatctt  tgttgagtac  atgaataaat  caactggtgt  gttttacgga    120
ggatgattat  gcttcattgt  gggattgtat  ttttcttctt  ctatcacagg  gagaagtgaa    180 atg aca acc tca cta gat aca gtt gag acc ttt ggt acc aca tcc tac          228
Met Thr Thr Ser Leu Asp Thr Val Glu Thr Phe Gly Thr Thr Ser Tyr
 1               5                  10                  15 tat gat gac gtg ggc ctg ctc tgt gaa aaa gct gat acc aga gca ctg          276
Tyr Asp Asp Val Gly Leu Leu Cys Glu Lys Ala Asp Thr Arg Ala Leu
            20                  25                  30 atg gcc cag ttt gtg ccc ccg ctg tac tcc ctg gtg ttc act gtg ggc          324
Met Ala Gln Phe Val Pro Pro Leu Tyr Ser Leu Val Phe Thr Val Gly
        35                  40                  45 ctc ttg ggc aat gtg gtg gtg gtg atg atc ctc ata aaa tac agg agg          372
```

```
                                                          -continued

Leu Leu Gly Asn Val Val Val Met Ile Leu Ile Lys Tyr Arg Arg
     50              55              60 ctc cga att atg acc aac atc tac ctg ctc aac ctg gcc att tcg gac       420
Leu Arg Ile Met Thr Asn Ile Tyr Leu Leu Asn Leu Ala Ile Ser Asp
 65              70              75              80 ctg ctc ttc ctc gtc acc ctt cca ttc tgg atc cac tat gtc agg ggg       468
Leu Leu Phe Leu Val Thr Leu Pro Phe Trp Ile His Tyr Val Arg Gly
             85              90              95 cat aac tgg gtt ttt ggc cat ggc atg tgt aag ctc ctc tca ggg ttt       516
His Asn Trp Val Phe Gly His Gly Met Cys Lys Leu Leu Ser Gly Phe
         100             105             110 tat cac aca ggc ttg tac agc gag atc ttt ttc ata atc ctg ctg aca       564
Tyr His Thr Gly Leu Tyr Ser Glu Ile Phe Phe Ile Ile Leu Leu Thr
     115             120             125 atc gac agg tac ctg gcc att gtc cat gct gtg ttt gcc ctt cga gcc       612
Ile Asp Arg Tyr Leu Ala Ile Val His Ala Val Phe Ala Leu Arg Ala
130             135             140 cgg act gtc act ttt ggt gtc atc acc agc atc gtc acc tgg ggc ctg       660
Arg Thr Val Thr Phe Gly Val Ile Thr Ser Ile Val Thr Trp Gly Leu
145             150             155             160 gca gtg cta gca gct ctt cct gaa ttt atc ttc tat gag act gaa gag       708
Ala Val Leu Ala Ala Leu Pro Glu Phe Ile Phe Tyr Glu Thr Glu Glu
             165             170             175 ttg ttt gaa gag act ctt tgc agt gct ctt tac cca gag gat aca gta       756
Leu Phe Glu Glu Thr Leu Cys Ser Ala Leu Tyr Pro Glu Asp Thr Val
         180             185             190 tat agc tgg agg cat ttc cac act ctg aga atg acc atc ttc tgt ctc       804
Tyr Ser Trp Arg His Phe His Thr Leu Arg Met Thr Ile Phe Cys Leu
     195             200             205 gtt ctc cct ctg ctc gtt atg gcc atc tgc tac aca gga atc atc aaa       852
Val Leu Pro Leu Leu Val Met Ala Ile Cys Tyr Thr Gly Ile Ile Lys
210             215             220 acg ctg ctg agg tgc ccc agt aaa aaa aag tac aag gcc atc cgg ctc       900
Thr Leu Leu Arg Cys Pro Ser Lys Lys Lys Tyr Lys Ala Ile Arg Leu
225             230             235             240 att ttt gtc atc atg gcg gtg ttt ttc att ttc tgg aca ccc tac aat       948
Ile Phe Val Ile Met Ala Val Phe Phe Ile Phe Trp Thr Pro Tyr Asn
             245             250             255 gtg gct atc ctt ctc tct tcc tat caa tcc atc tta ttt gga aat gac       996
Val Ala Ile Leu Leu Ser Ser Tyr Gln Ser Ile Leu Phe Gly Asn Asp
         260             265             270 tgt gag cgg acg aag cat ctg gac ctg gtc atg ctg gtg aca gag gtg      1044
Cys Glu Arg Thr Lys His Leu Asp Leu Val Met Leu Val Thr Glu Val
     275             280             285 atc gcc tac tcc cac tgc tgc atg aac ccg gtg atc tac gcc ttt gtt      1092
Ile Ala Tyr Ser His Cys Cys Met Asn Pro Val Ile Tyr Ala Phe Val
290             295             300 gga gag agg ttc cgg aag tac ctg cgc cac ttc ttc cac agg cac ttg      1140
Gly Glu Arg Phe Arg Lys Tyr Leu Arg His Phe Phe His Arg His Leu
305             310             315             320 ctc atg cac ctg ggc aga tac atc cca ttc ctt cct agt gag aag ctg      1188
Leu Met His Leu Gly Arg Tyr Ile Pro Phe Leu Pro Ser Glu Lys Leu
             325             330             335 gaa aga acc agc tct gtc tct cca tcc aca gca gag ccg gaa ctc tct      1236
Glu Arg Thr Ser Ser Val Ser Pro Ser Thr Ala Glu Pro Glu Leu Ser
         340             345             350 att gtg ttt tag gtagatgcag aaaattgcct aagaggaag gaccaaggag          1288
Ile Val Phe  *
355
```

-continued

```
atnaagcaaa cacattaagc cttccacact caccctctaaa acagtccttc aaaccttcca    1348
gtgcaacact gaagctctta agacactgaa atatacacac agcagtagca gtagatgcat    1408
gtaccctaag gtcattacca caggccaggg ctgggcagcg tactcatcat caacctaaaa    1468
agcagagctt tgcttctctc tctaaaatga gttacctata ttttaatgca cctgaatgtt    1528
agatagttac tatatgccgc tacaaaaagg taaaacttt tatattttat acattaactt    1588
cagccagcta ttatataaat aaaacatttt cacacaatac aataagttaa ctatttatt    1648 ttctaatgtg cctagttctt tccctgctta atgaaaagct t                        1689
```

<210> SEQ ID NO 16
<211> LENGTH: 355
<212> TYPE: PRT
<213> ORGANISM: Homo sapiens

<400> SEQUENCE: 16

```
Met Thr Thr Ser Leu Asp Thr Val Glu Thr Phe Gly Thr Thr Ser Tyr
  1               5                  10                  15

Tyr Asp Asp Val Gly Leu Leu Cys Glu Lys Ala Asp Thr Arg Ala Leu
             20                  25                  30

Met Ala Gln Phe Val Pro Pro Leu Tyr Ser Leu Val Phe Thr Val Gly
         35                  40                  45

Leu Leu Gly Asn Val Val Val Val Met Ile Leu Ile Lys Tyr Arg Arg
     50                  55                  60

Leu Arg Ile Met Thr Asn Ile Tyr Leu Leu Asn Leu Ala Ile Ser Asp
 65                  70                  75                  80

Leu Leu Phe Leu Val Thr Leu Pro Phe Trp Ile His Tyr Val Arg Gly
                 85                  90                  95

His Asn Trp Val Phe Gly His Gly Met Cys Lys Leu Leu Ser Gly Phe
            100                 105                 110

Tyr His Thr Gly Leu Tyr Ser Glu Ile Phe Phe Ile Ile Leu Leu Thr
        115                 120                 125

Ile Asp Arg Tyr Leu Ala Ile Val His Ala Val Phe Ala Leu Arg Ala
    130                 135                 140

Arg Thr Val Thr Phe Gly Val Ile Thr Ser Ile Val Thr Trp Gly Leu
145                 150                 155                 160

Ala Val Leu Ala Ala Leu Pro Glu Phe Ile Phe Tyr Glu Thr Glu Glu
                165                 170                 175

Leu Phe Glu Glu Thr Leu Cys Ser Ala Leu Tyr Pro Glu Asp Thr Val
            180                 185                 190

Tyr Ser Trp Arg His Phe His Thr Leu Arg Met Thr Ile Phe Cys Leu
        195                 200                 205

Val Leu Pro Leu Leu Val Met Ala Ile Cys Tyr Thr Gly Ile Ile Lys
    210                 215                 220

Thr Leu Leu Arg Cys Pro Ser Lys Lys Lys Tyr Lys Ala Ile Arg Leu
225                 230                 235                 240

Ile Phe Val Ile Met Ala Val Phe Phe Ile Phe Trp Thr Pro Tyr Asn
                245                 250                 255

Val Ala Ile Leu Leu Ser Ser Tyr Gln Ser Ile Leu Phe Gly Asn Asp
            260                 265                 270

Cys Glu Arg Thr Lys His Leu Asp Leu Val Met Leu Val Thr Glu Val
        275                 280                 285

Ile Ala Tyr Ser His Cys Cys Met Asn Pro Val Ile Tyr Ala Phe Val
    290                 295                 300
```

-continued

```
Gly Glu Arg Phe Arg Lys Tyr Leu Arg His Phe His Arg His Leu
305                 310                 315                 320

Leu Met His Leu Gly Arg Tyr Ile Pro Phe Leu Pro Ser Glu Lys Leu
            325                 330                 335

Glu Arg Thr Ser Ser Val Ser Pro Ser Thr Ala Glu Pro Glu Leu Ser
            340                 345                 350

Ile Val Phe
        355

<210> SEQ ID NO 17
<211> LENGTH: 1244
<212> TYPE: DNA
<213> ORGANISM: Homo sapiens
<220> FEATURE:
<221> NAME/KEY: CDS
<222> LOCATION: (5)...(1093)

<400> SEQUENCE: 17 agag atg ggg acg gag gcc aca gag cag gtt tcc tgg ggc cat tac tct        49
     Met Gly Thr Glu Ala Thr Glu Gln Val Ser Trp Gly His Tyr Ser
       1               5                  10                  15 ggg gat gaa gag gac gca tac tcg gct gag cca ctg ccg gag ctt tgc        97
Gly Asp Glu Glu Asp Ala Tyr Ser Ala Glu Pro Leu Pro Glu Leu Cys
             20                  25                  30 tac aag gcc gat gtc cag gcc ttc agc cgg gcc ttc caa ccc agt gtc       145
Tyr Lys Ala Asp Val Gln Ala Phe Ser Arg Ala Phe Gln Pro Ser Val
         35                  40                  45 tcc ctg acc gtg gct gcg ctg ggt ctg gcc ggc aat ggc ctg gtc ctg       193
Ser Leu Thr Val Ala Ala Leu Gly Leu Ala Gly Asn Gly Leu Val Leu
     50                  55                  60 gcc acc cac ctg gca gcc cga cgc gca gcg cgc tcg ccc acc tct gcc       241
Ala Thr His Leu Ala Ala Arg Arg Ala Ala Arg Ser Pro Thr Ser Ala
 65                  70                  75 cac ctg ctc cag ctg gcc ctg gcc gac ctc ttg ctg gcc ctg act ctg       289
His Leu Leu Gln Leu Ala Leu Ala Asp Leu Leu Leu Ala Leu Thr Leu
 80                  85                  90                  95 ccc ttc gcg gca gca ggg gct ctt cag ggc tgg agt ctg gga agt gcc       337
Pro Phe Ala Ala Ala Gly Ala Leu Gln Gly Trp Ser Leu Gly Ser Ala
                100                 105                 110 acc tgc cgc acc atc tct ggc ctc tac tcg gcc tcc ttc cac gcc ggc       385
Thr Cys Arg Thr Ile Ser Gly Leu Tyr Ser Ala Ser Phe His Ala Gly
            115                 120                 125 ttc ctc ttc ctg gcc tgt atc agc gcc gac cgc tac gtg gcc atc gcg       433
Phe Leu Phe Leu Ala Cys Ile Ser Ala Asp Arg Tyr Val Ala Ile Ala
        130                 135                 140 cga gcg ctc cca gcc ggg ccg cgg ccc tcc act ccc ggc cgc gca cac       481
Arg Ala Leu Pro Ala Gly Pro Arg Pro Ser Thr Pro Gly Arg Ala His
145                 150                 155 ttg gtc tcc gtc atc gtg tgg ctg ctg tca ctg ctc ctg gcg ctg cct       529
Leu Val Ser Val Ile Val Trp Leu Leu Ser Leu Leu Leu Ala Leu Pro
160                 165                 170                 175 gcg ctg ctc ttc agc cag gat ggg cag cgg gaa ggc caa cga cgc tgt       577
Ala Leu Leu Phe Ser Gln Asp Gly Gln Arg Glu Gly Gln Arg Arg Cys
                180                 185                 190 cgc ctc atc ttc ccc gag ggc ctc acg cag acg gtg aag ggg gcg agc       625
Arg Leu Ile Phe Pro Glu Gly Leu Thr Gln Thr Val Lys Gly Ala Ser
            195                 200                 205 gcc gtg gcg cag gtg gcc ctg ggc ttc gcg ctg ccg ctg ggc gtc atg       673
Ala Val Ala Gln Val Ala Leu Gly Phe Ala Leu Pro Leu Gly Val Met
        210                 215                 220
```

```
gta gcc tgc tac gcg ctt ctg ggc cgc acg ctg ctg gcc gcc agg ggg        721
Val Ala Cys Tyr Ala Leu Leu Gly Arg Thr Leu Leu Ala Ala Arg Gly
        225                 230                 235 ccc gag cgc cgg cgt gcg ctg cgc gtc gtg gtg gct ctg gtg gcg gcc        769
Pro Glu Arg Arg Arg Ala Leu Arg Val Val Val Ala Leu Val Ala Ala
240                 245                 250                 255 ttc gtg gtg ctg cag ctg ccc tac agc ctc gcc ctg ctg gat act            817
Phe Val Val Leu Gln Leu Pro Tyr Ser Leu Ala Leu Leu Asp Thr
                260                 265                 270 gcc gat cta ctg gct gcg cgc gag cgg agc tgc cct gcc agc aaa cgc        865
Ala Asp Leu Leu Ala Ala Arg Glu Arg Ser Cys Pro Ala Ser Lys Arg
        275                 280                 285 aag gat gtc gca ctg ctg gtg acc agc ggc ttg gcc ctc gcc cgc tgt        913
Lys Asp Val Ala Leu Leu Val Thr Ser Gly Leu Ala Leu Ala Arg Cys
290                 295                 300 ggc ctc aat ccc gtt ctc tac gcc ttc ctg ggc ctg cgc ttc cgc cag        961
Gly Leu Asn Pro Val Leu Tyr Ala Phe Leu Gly Leu Arg Phe Arg Gln
        305                 310                 315 gac ctg cgg agg ctg cta cgg ggt ggg agc tcg ccc tca ggg cct caa       1009
Asp Leu Arg Arg Leu Leu Arg Gly Gly Ser Ser Pro Ser Gly Pro Gln
320                 325                 330                 335 ccc cgc cgc ggc tgc ccc cgc cgg ccc cgc ctt tct tcc tgc tca gct       1057
Pro Arg Arg Gly Cys Pro Arg Arg Pro Arg Leu Ser Ser Cys Ser Ala
                340                 345                 350 ccc acg gag acc cac agt ctc tcc tgg gac aac tag ggctgcgaat            1103
Pro Thr Glu Thr His Ser Leu Ser Trp Asp Asn *
        355                 360 ctagaggagg gggcaggctg agggtcgtgg gaaaggggag taggtggggg aacactgaga     1163
aagaggcagg gacctaaagg gactacctct gtgccttgcc acattaaatt gataacatgg     1223
aaatgaaaaa aaaaaaaaaa a                                              1244

<210> SEQ ID NO 18
<211> LENGTH: 362
<212> TYPE: PRT
<213> ORGANISM: Homo sapiens

<400> SEQUENCE: 18

Met Gly Thr Glu Ala Thr Glu Gln Val Ser Trp Gly His Tyr Ser Gly
1               5                   10                  15

Asp Glu Glu Asp Ala Tyr Ser Ala Glu Pro Leu Pro Glu Leu Cys Tyr
            20                  25                  30

Lys Ala Asp Val Gln Ala Phe Ser Arg Ala Phe Gln Pro Ser Val Ser
        35                  40                  45

Leu Thr Val Ala Ala Leu Gly Leu Ala Gly Asn Gly Leu Val Leu Ala
    50                  55                  60

Thr His Leu Ala Ala Arg Arg Ala Ala Arg Ser Pro Thr Ser Ala His
65                  70                  75                  80

Leu Leu Gln Leu Ala Leu Ala Asp Leu Leu Leu Ala Leu Thr Leu Pro
                85                  90                  95

Phe Ala Ala Gly Ala Leu Gln Gly Trp Ser Leu Gly Ser Ala Thr Cys
            100                 105                 110

Cys Arg Thr Ile Ser Gly Leu Tyr Ser Ala Ser Phe His Ala Gly Phe
        115                 120                 125

Leu Phe Leu Ala Cys Ile Ser Ala Asp Arg Tyr Val Ala Ile Ala Arg
    130                 135                 140

Ala Leu Pro Ala Gly Pro Arg Pro Ser Thr Pro Gly Arg Ala His Leu
145                 150                 155                 160
```

```
Val Ser Val Ile Val Trp Leu Leu Ser Leu Leu Ala Leu Pro Ala
            165                 170                 175

Leu Leu Phe Ser Gln Asp Gly Gln Arg Glu Gly Gln Arg Arg Cys Arg
        180                 185                 190

Leu Ile Phe Pro Glu Gly Leu Thr Gln Thr Val Lys Gly Ala Ser Ala
        195                 200                 205

Val Ala Gln Val Ala Leu Gly Phe Ala Leu Pro Leu Gly Val Met Val
        210                 215                 220

Ala Cys Tyr Ala Leu Leu Gly Arg Thr Leu Leu Ala Ala Arg Gly Pro
225                 230                 235                 240

Glu Arg Arg Arg Ala Leu Arg Val Val Ala Leu Val Ala Ala Phe
            245                 250                 255

Val Val Leu Gln Leu Pro Tyr Ser Leu Ala Leu Leu Leu Asp Thr Ala
            260                 265                 270

Asp Leu Leu Ala Ala Arg Glu Arg Ser Cys Pro Ala Ser Lys Arg Lys
            275                 280                 285

Asp Val Ala Leu Leu Val Thr Ser Gly Leu Ala Leu Ala Arg Cys Gly
            290                 295                 300

Leu Asn Pro Val Leu Tyr Ala Phe Leu Gly Leu Arg Phe Arg Gln Asp
305                 310                 315                 320

Leu Arg Arg Leu Leu Arg Gly Gly Ser Ser Pro Ser Gly Pro Gln Pro
            325                 330                 335

Arg Arg Gly Cys Pro Arg Pro Arg Leu Ser Ser Cys Ser Ala Pro
            340                 345                 350

Thr Glu Thr His Ser Leu Ser Trp Asp Asn
            355                 360
```

<210> SEQ ID NO 19
<211> LENGTH: 1086
<212> TYPE: DNA
<213> ORGANISM: Homo sapiens
<220> FEATURE:
<221> NAME/KEY: CDS
<222> LOCATION: (1)...(1086)

<400> SEQUENCE: 19

```
atg ggg acg gag gcc aca gag cag gtt tcc tgg ggc cat tac tct ggg      48
Met Gly Thr Glu Ala Thr Glu Gln Val Ser Trp Gly His Tyr Ser Gly
 1               5                  10                  15 gat gaa gag gac gca tac tcg gct gag cca ctg ccg gag ctt tgc tac      96
Asp Glu Glu Asp Ala Tyr Ser Ala Glu Pro Leu Pro Glu Leu Cys Tyr
             20                  25                  30 aag gcc gat gtc cag gcc ttc agc cgg gcc ttc caa ccc agt gtc tcc     144
Lys Ala Asp Val Gln Ala Phe Ser Arg Ala Phe Gln Pro Ser Val Ser
         35                  40                  45 ctg acc gtg gct gcg ctg ggt ctg gcc ggc aat ggc ctg gtc ctg gcc     192
Leu Thr Val Ala Ala Leu Gly Leu Ala Gly Asn Gly Leu Val Leu Ala
     50                  55                  60 acc cac ctg gca gcc cga cgc gca gcg cgc tcg ccc acc tct gcc cac     240
Thr His Leu Ala Ala Arg Arg Ala Ala Arg Ser Pro Thr Ser Ala His
 65                  70                  75                  80 ctc ctc cag ctg gcc ctg gcc gac ctc ttg ctg gcc ctg act ctg ccc     288
Leu Leu Gln Leu Ala Leu Ala Asp Leu Leu Leu Ala Leu Thr Leu Pro
                 85                  90                  95 ttc gcg gca gca ggg gct ctt cag ggc tgg agt ctg gga agt gcc acc     336
Phe Ala Ala Ala Gly Ala Leu Gln Gly Trp Ser Leu Gly Ser Ala Thr
            100                 105                 110
```

```
tgc cgc acc atc tct ggc ctc tac tcg gcc tcc ttc cac gcc ggc ttc      384
Cys Arg Thr Ile Ser Gly Leu Tyr Ser Ala Ser Phe His Ala Gly Phe
        115                 120                 125 ctc ttc ctg gcc tgt atc agc gcc gac cgc tac gtg gcc atc gcg cga      432
Leu Phe Leu Ala Cys Ile Ser Ala Asp Arg Tyr Val Ala Ile Ala Arg
    130                 135                 140 gcg ctc cca gcc ggg ccg cgg ccc tcc act ccc ggc cgc gca cac ttg      480
Ala Leu Pro Ala Gly Pro Arg Pro Ser Thr Pro Gly Arg Ala His Leu
145                 150                 155                 160 gtc tcc gtc atc gtg tgg ctg ctg tca ctg ctc ctg gcg ctg cct gcg      528
Val Ser Val Ile Val Trp Leu Leu Ser Leu Leu Leu Ala Leu Pro Ala
                165                 170                 175 ctg ctc ttc agc cag gat ggg cag cgg gaa ggc caa cga cgc tgt cgc      576
Leu Leu Phe Ser Gln Asp Gly Gln Arg Glu Gly Gln Arg Arg Cys Arg
            180                 185                 190 ctc atc ttc ccc gag ggc ctc acg cag acg gtg aag ggg gcg agc gcc      624
Leu Ile Phe Pro Glu Gly Leu Thr Gln Thr Val Lys Gly Ala Ser Ala
        195                 200                 205 gtg gcg cag gtg gcc ctg ggc ttc gcg ctg ccg ctg ggc gtc atg gta      672
Val Ala Gln Val Ala Leu Gly Phe Ala Leu Pro Leu Gly Val Met Val
    210                 215                 220 gcc tgc tac gcg ctt ctg ggc cgc acg ctg gcc gcc agg ggg ccc gag      720
Ala Cys Tyr Ala Leu Leu Gly Arg Thr Leu Ala Ala Arg Gly Pro Glu
225                 230                 235                 240 cgc cgg cgt gcg ctg cgc gtc gtg gtg gct ctg gtg gcg gcc ttc gtg      768
Arg Arg Arg Ala Leu Arg Val Val Val Ala Leu Val Ala Ala Phe Val
                245                 250                 255 gtg ctg cag ctg ccc tac agc ctc gcc ctg ctg gat act gcc gat         816
Val Leu Gln Leu Pro Tyr Ser Leu Ala Leu Leu Asp Thr Ala Asp
            260                 265                 270 cta ctg gct gcg cgc gag cgg agc tgc cct gcc agc aaa cgc aag gat      864
Leu Leu Ala Ala Arg Glu Arg Ser Cys Pro Ala Ser Lys Arg Lys Asp
        275                 280                 285 gtc gca ctg ctg gtg acc agc ggc ttg gcc ctc gcc cgc tgt ggc ctc      912
Val Ala Leu Leu Val Thr Ser Gly Leu Ala Leu Ala Arg Cys Gly Leu
    290                 295                 300 aat ccc gtt ctc tac gcc ttc ctg ggc ctg cgc ttc cgc cag gac ctg      960
Asn Pro Val Leu Tyr Ala Phe Leu Gly Leu Arg Phe Arg Gln Asp Leu
305                 310                 315                 320 cgg agg ctg cta cgg ggt ggg agc tgc ccc tca ggg cct caa ccc cgc     1008
Arg Arg Leu Leu Arg Gly Gly Ser Cys Pro Ser Gly Pro Gln Pro Arg
                325                 330                 335 cgc ggc tgc ccc cgc cgg ccc cgc ctt tct tcc tgc tca gct ccc acg     1056
Arg Gly Cys Pro Arg Arg Pro Arg Leu Ser Ser Cys Ser Ala Pro Thr
            340                 345                 350 gag acc cac agt ctc tcc tgg gac aac tag                             1086
Glu Thr His Ser Leu Ser Trp Asp Asn *
        355                 360

<210> SEQ ID NO 20
<211> LENGTH: 361
<212> TYPE: PRT
<213> ORGANISM: Homo sapiens

<400> SEQUENCE: 20

Met Gly Thr Glu Ala Thr Glu Gln Val Ser Trp Gly His Tyr Ser Gly
 1               5                  10                  15

Asp Glu Glu Asp Ala Tyr Ser Ala Glu Pro Leu Pro Glu Leu Cys Tyr
                20                  25                  30

Lys Ala Asp Val Gln Ala Phe Ser Arg Ala Phe Gln Pro Ser Val Ser
```

```
            35                  40                  45
Leu Thr Val Ala Ala Leu Gly Leu Ala Gly Asn Gly Leu Val Leu Ala
     50                  55                  60

Thr His Leu Ala Ala Arg Arg Ala Ala Arg Ser Pro Thr Ser Ala His
 65                  70                  75                  80

Leu Leu Gln Leu Ala Leu Ala Asp Leu Leu Ala Leu Thr Leu Pro
                 85                  90                  95

Phe Ala Ala Gly Ala Leu Gln Gly Trp Ser Leu Gly Ser Ala Thr
                100                 105                 110

Cys Arg Thr Ile Ser Gly Leu Tyr Ser Ala Ser Phe His Ala Gly Phe
                115                 120                 125

Leu Phe Leu Ala Cys Ile Ser Ala Asp Arg Tyr Val Ala Ile Ala Arg
                130                 135                 140

Ala Leu Pro Ala Gly Pro Arg Pro Ser Thr Pro Gly Arg Ala His Leu
145                 150                 155                 160

Val Ser Val Ile Val Trp Leu Leu Ser Leu Leu Leu Ala Leu Pro Ala
                165                 170                 175

Leu Leu Phe Ser Gln Asp Gly Gln Arg Glu Gly Gln Arg Arg Cys Arg
                180                 185                 190

Leu Ile Phe Pro Glu Gly Leu Thr Gln Thr Val Lys Gly Ala Ser Ala
                195                 200                 205

Val Ala Gln Val Ala Leu Gly Phe Ala Leu Pro Leu Gly Val Met Val
210                 215                 220

Ala Cys Tyr Ala Leu Leu Gly Arg Thr Leu Ala Ala Arg Gly Pro Glu
225                 230                 235                 240

Arg Arg Arg Ala Leu Arg Val Val Val Ala Leu Val Ala Ala Phe Val
                245                 250                 255

Val Leu Gln Leu Pro Tyr Ser Leu Ala Leu Leu Leu Asp Thr Ala Asp
                260                 265                 270

Leu Leu Ala Ala Arg Glu Arg Ser Cys Pro Ala Ser Lys Arg Lys Asp
                275                 280                 285

Val Ala Leu Leu Val Thr Ser Gly Leu Ala Leu Ala Arg Cys Gly Leu
                290                 295                 300

Asn Pro Val Leu Tyr Ala Phe Leu Gly Leu Arg Phe Arg Gln Asp Leu
305                 310                 315                 320

Arg Arg Leu Leu Arg Gly Gly Ser Cys Pro Ser Gly Pro Gln Pro Arg
                325                 330                 335

Arg Gly Cys Pro Arg Arg Pro Arg Leu Ser Ser Cys Ser Ala Pro Thr
                340                 345                 350

Glu Thr His Ser Leu Ser Trp Asp Asn
                355                 360

<210> SEQ ID NO 21
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 21
ccatcgtggc cttggctgtc tgtg                                          24

<210> SEQ ID NO 22
<211> LENGTH: 24
<212> TYPE: DNA
<213> ORGANISM: Artificial Sequence
```

-continued

<220> FEATURE:
<223> OTHER INFORMATION: Synthetic oligonucleotide

<400> SEQUENCE: 22
gccgtatgtt tcgtgtttcc cctg     24

<210> SEQ ID NO 23
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 23
gggaagtatg gcttctgagg c     21

<210> SEQ ID NO 24
<211> LENGTH: 9
<212> TYPE: PRT
<213> ORGANISM: Influenza virus

<400> SEQUENCE: 24

Tyr Pro Tyr Asp Val Pro Asp Tyr Ala
1               5

METHOD FOR IDENTIFYING AGENTS WHICH MODULATE CHEMOKINE "MEC"-INDUCED FUNCTIONS OF CCR3

RELATED APPLICATIONS

This application is a continuation-in-part of U.S. application Ser. No. 09/638,914, filed Aug. 15, 2000, the teachings of which are incorporated herein by reference in their entirety.

GOVERNMENT SUPPORT

The invention was supported, in part, by grants GM-37734, AI-37832, HL-57492 and AI-47822 from National Institutes of Health and an award from the Veterans Administration. The Government has certain rights in the invention.

BACKGROUND OF THE INVENTION

Chemokines are a large and growing family of 6–14 kD proteins that mediate a wide range of biological functions (Taub, D. D. and Openheim, J. J., *Ther. Immunol.*, 1:229–246 (1994)). The chemokines can be divided into families based on the position of four cysteine residues that form two disulfide bonds (Kelner, G. S., et al., *Science*, 266:12395–1399 (1994); Bazan, J. F., et al., *Nature*, 385:640–644 (1997); Pin, Y., et al, *Nature*, 385:611–617 (1997)). Chemokine receptors can also be divided into families based on the type of chemokine they bind, although, no clear structural differences have been identified that distinguish the receptor sub-families (Mackay, C. R., *J. Exp. Med.*, 184:799–802 (1996)). In addition, there are a number of so-called "orphan" chemokine receptors which have amino acid sequences that are similar to well-characterized chemokine receptors, but for which the biological functions and specific receptor agonists (e.g., natural ligands) remain unknown.

Chemokines play a vital role in leukocyte adhesion and extravasation, and help direct lymphocyte localization to specialized microenvironments within tissues. Chemokines also help define sites of targeted lymphocyte trafficking from the blood. For example, the chemokines SLC and ELC which are both ligands for C—C chemokine receptor 7 (CCR7) play a critical role in lymphocyte and dendritic cell trafficking to secondary lymphoid tissues, including lymph nodes (Warnock, R. A. et al., *J. Exp. Med.* 191:77 (2000); Stein J. V. et al., *J. Exp. Med.* 191:61 (2000); Iwasaki, A and Kelsall, B. L., *J. Exp. Med.* 191:1381 (2000); and Cyster, J. G., *Curr. Biol.* 10:R30 (2000)). Further, the chemokine TARC, a ligand for C—C chemokine receptor 4 (CCR4), has been implicated in regulating lymphocyte-endothelial cell interactions and lymphocyte recruitment into non-intestinal tissues, particularly the skin (Campbell, J. J. et al., *Nature* 400:776 (1999)). Of further interest in the context of the regional specialization of immune responses is the constitutive and selective expression of chemokine TECK (a ligand for C—C chemokine receptor 9 (CCR9)) by epithelial cells of the small intestine (Wurbel, M. A. et al., *Eur. J. Immunol.* 30:262 (2000)), and of the chemokine CTACK (a ligand for C—C chemokine receptor 10 (CCR10)) by skin keratinocytes (Morales, J. et al, *Proc. Natl. Acad. Sci. U.S.A.* 96:14470 (1999)).

Agents which can inhibit particular chemokine/chemokine receptor interactions can prevent leukocyte trafficking (e.g., to particular tissues) and can have beneficial effects in models of acute and chronic inflammation ((Bargatze, R. F. and Butcher, E. C., *J. Exp. Med.*, 178:367–372 (1993); Sekido, N., et al., *Nature*, 365:654–657 (1993); and Karpus, W. J., et al, *J. Immunol.*, 155:5003–5010 (1995)). Therefore, there is a need for methods for identifying agents which can inhibit the binding of particular chemokines to particular chemokine receptors. There is also a need for methods for treating inflammatory conditions using such agents.

SUMMARY OF THE INVENTION

The invention relates to a method of detecting or identifying an agent (i.e., molecule or compound) which modulates the binding of a mammalian MEC to a mammalian C—C chemokine receptor 3 (CCR3) and/or to a mammalian C—C chemokine receptor 10 (CCR10) and/or which modulates the function of CCR3 and/or CCR10 upon MEC binding (e.g., MEC-induced signaling). Binding of agent to CCR3 and/or CCR10 can be detected directly or indirectly. For example, binding can be detected indirectly by monitoring a cellular response induced upon binding of MEC to CCR3 and/or CCR10. An agent which modulates (inhibits or promotes) the binding of MEC to CCR3 and/or CCR10 can be identified in a competitive binding assay. In some embodiments, the agent can be a small organic molecule. In other embodiments, the agent can be an antibody or antigen-binding fragment thereof. A suitable mammalian CCR3 or MEC-binding variant thereof and/or a mammalian CCR10 or MEC-binding variant thereof can be used. In one embodiment, a cell (e.g., primary cell, cell line, recombinant cell) that expresses a mammalian CCR3 or MEC-binding variant thereof is used. In another embodiment, a cell (e.g., cell line, recombinant cell) that expresses a mammalian CCR10 or MEC-binding variant thereof is used. In additional embodiments, a membrane preparation of a cell that expresses a mammalian CCR3 or MEC-binding variant thereof and/or a mammalian CCR3 or MEC-binding variant thereof is used.

The invention further relates to an agent, identified by the methods described herein, which modulates (inhibits or promotes) binding of a mammalian MEC to a mammalian CCR3 or MEC-binding variant thereof and/or a mammalian CCR10 or MEC-binding variant thereof and/or which modulates the function of mammalian CCR3 or variant and/or mammalian CCR10 or variant upon MEC binding (e.g., MEC-induced signaling). In one embodiment, the invention relates to an immunoglobulin or antigen-binding fragment thereof which binds a naturally occurring mammalian CCR10 and inhibits binding of a naturally occurring mammalian MEC to said receptor. In another embodiment, the invention relates to an immunoglobulin or antigen-binding fragment thereof which binds a naturally occurring mammalian MEC and inhibits binding of said MEC to a naturally occurring mammalian CCR3 and/or a naturally occurring mammalian CCR10. In a further embodiment, the invention relates to a small organic molecule which modulates (inhibits or promotes) binding of a mammalian MEC to a mammalian CCR3 or MEC-binding variant thereof and/or a mammalian CCR10 or MEC-binding variant thereof.

The invention also relates to therapeutic methods in which agents that modulate (inhibits or promotes) the binding of a mammalian MEC to a mammalian C—C chemokine receptor 3 (CCR3) and/or to a mammalian C—C chemokine receptor 10 (CCR10) are administered to a subject in need of such therapy. In one aspect, the therapeutic method is a method of treating a subject having an inflammatory disease. In one embodiment, the subject has an oral inflammatory condition, such as Sjogren's syndrome or Behcet's syndrome. In another embodiment, the subject has a chronic obstructive lung disease, such as asthma. In additional embodiments the subject has inflammatory bowel disease (e.g., Crohn's disease, ulcerative colitis, celiac disease), mastitis, IgA nephropathy or dermatitis herpetiformis. In other embodiments, an immunoglobulin or antigen-binding fragment thereof which inhibits the binding of MEC to CCR3 and/or CCR10 is administered to a subject in need thereof.

The invention further relates to an agent which modulates (inhibits or promotes) binding of a mammalian MEC to a mammalian CCR3 or MEC-binding variant thereof and/or modulates binding of a mammalian MEC to a mammalian CCR10 or MEC-binding variant thereof (e.g., antibody, antigen-binding fragment), as described herein, for use in therapy (including prophylaxis) or diagnosis, and to the use of such an agent for the manufacture of a medicament for the treatment of a particular disease or condition as described herein (e.g., an inflammatory disease).

The invention also relates to an agent that modulates (inhibits or promotes) the activity of an IgA antibody-secreting cell in a subject. In one embodiment, the invention is a method of modulating the activity of an IgA antibody-secreting cell comprising administering an effective amount of MEC to a subject. In another embodiment, the invention is a method of modulating the activity of an IgA antibody-secreting cell comprising administering an effective amount of an agent that promotes the binding of MEC to CCR3 and/or CCR10 or an agent that inhibits the binding of MEC to CCR3 and/or CCR10.

BRIEF DESCRIPTION OF THE DRAWINGS

FIG. 1A illustrates the nucleotide sequence (SEQ ID NO:1) of a cDNA encoding human (*Homo sapiens*) mucosae-associated epithelial chemokine (MEC), and the amino acid sequence of the encoded protein (SEQ ID NO:2). The cloned cDNA consists of 768 nucleotides with an open reading frame encoding 127 amino acids. The open reading frame includes a predicted signal peptide of 22 amino acids (amino acid residues 1–22 of SEQ ID NO:2, underlined).

FIG. 1C is a multiple sequence alignment of amino acid residues 23–127 of human MEC (residues 23–127 of SEQ ID NO: 2), amino acid residues 25–112 of human CTACK (residues 25–112 of SEQ ID NO:11), amino acid residues 26–120 of murine (*Mus musculus*) CTACK (residues 26–120 of SEQ ID NO:12), amino acid residues 24–150 of human TECK (residues 24–150 of SEQ ID NO:13) and amino acid residues 24–144 of murine TECK (residues 24–144 of SEQ ID NO:14). The sequence of human CTACK, murine CTACK, human TECK and murine TECK are deposited in GenBank under accession numbers AF082393, AF082392, U86358 and U86357, respectively. The entire teachings of each of the foregoing GenBank entries are incorporated herein by reference. Gaps that were inserted to provide optimal alignment are represented by "-".

FIGS. 3A and 3B are a photograph of an autoradiogram of a multiple tissue RNA dot blot that was probed for MEC transcripts using $^{32}$P-labeled full-length MEC cDNA probe (nucleotides 1–739 of SEQ ID NO:1) and a diagram that shows the type and position of the RNA on the dot blot membrane, respectively. High levels of MEC-encoding mRNA were detected in diverse mucosal organs such as salivary gland, mammary gland, trachea, colon, and rectum with lower message levels in various segments of the small intestine.

FIGS. 4A–4B illustrates the nucleic acid sequence of a cDNA encoding human a C—C chemokine receptor 3 (CCR3) (SEQ ID NO:15) deposited in GenBank under Accession Number U49727 having an open-reading frame beginning at position 181. The entire teachings of GenBank Accession Number U49727 are incorporated herein by reference.

FIG. 5 illustrates the amino acid sequence of human CCR3 polypeptide (SEQ ID NO:16) encoded by the DNA sequence shown in FIGS. 4A–4B (SEQ ID NO:15).

FIGS. 6A–6B illustrates the nucleic acid sequence of a cDNA encoding a human C—C chemokine receptor 10 (CCR10) (SEQ ID NO:17) deposited in GenBank under Accession Number NM_016602, having an open-reading frame beginning at position 5. The entire teachings of GenBank Accession Number NM_016602 are incorporated herein by reference.

FIG. 7 illustrates the amino acid sequence of human CCR10polypeptide (SEQ ID NO:18) encoded by the DNA sequence shown in FIGS. 6A–6B (SEQ ID NO:17).

FIGS. 8A–8B illustrates the nucleic acid sequence of a cDNA encoding human C—C chemokine receptor 10 (CCR10) (SEQ ID NO:19) deposited in GenBank under Accession Number AF208237, having an open-reading frame beginning at position 1. The entire teachings of GenBank Accession Number AF208237 are incorporated herein by reference.

FIG. 9 illustrates the amino acid sequence of human CCR10 polypeptide (SEQ ID NO:20) encoded by the DNA sequence shown in FIGS. 8A–8B (SEQ ID NO:19).

FIG. 10 is a histogram showing that IgA antibody-secreting cells (IgA ASC) from mouse spleens exhibit chemotaxis to human MEC (hMEC) in a dose-dependent manner with an optimal chemotactic dose of 250 nM. Medium, or medium containing 100 nM, 250 nM or 500 nM of hMEC, was added to the bottom chamber of TRANSWELL plates (tissue culture plates fitted with TRANSWELL permeable tissue culture support devices), and media containing $2 \times 10^6$ cells isolated from mouse spleens was added to the top chamber. The plates were cultured for about 2 hours and the number of IgA antibody-secreting cells that migrated into the bottom chamber was determined using an ELISPOT assay. Percent migration is the number of IgA antibody-secreting cells which migrated to hMEC divided by the number of IgA antibody-secreting cells in the input cell population (determined separately using an ELISPOT assay), displayed as a percentage. The error bars represent standard error of the mean.

FIG. 11 is a histogram showing that IgA antibody-secreting cells (IgA ASC) from mouse spleens exhibit chemotaxis to human MEC (hMEC) and mouse MEC (mMEC). Media or media containing 100 nM of mMEC, 250 nM of mMEC or 250 nM of hMEC was added to the bottom chamber of TRANSWELL plates (tissue culture plates fitted with TRANSWELL permeable tissue culture support devices), and media containing $2 \times 10^6$ cells isolated from mouse spleens was added to the top chamber. The plates were cultured for about 2 hours and the number of IgA antibody-secreting cells that migrated into the bottom chamber was determined using an ELISPOT assay. Percent migration is the number of IgA antibody-secreting cells which migrated to hMEC divided by the number of IgA antibody-secreting cells in the input cell population (determined separately using an ELISPOT assay), displayed as a percentage. The error bars represent standard error of the mean.

FIG. 12 is a histogram showing that IgA antibody-secreting cells (IgA ASC) are present in the following mouse tissues: Peyer's Patch, mesenteric lymph nodes (MLN), spleen, salivary gland lymph nodes (SG-LN), tracheo-bronchial lymph nodes (TB-LN) and the lymph node draining the genital tract (iliac). Cells from the listed tissues were subjected to an ELISPOT assay to quantify the number of IgA antibody-secreting cells. Values are plotted as the number of IgA ASC/million cells. n values indicate the number of assays that were performed for each tissue and the error bars represent standard error of the mean.

FIG. 13 is a histogram showing that IgA antibody-secreting cells (IgA ASC) from mouse Peyer's Patch (PP), mesenteric lymph nodes (MLN), spleen, salivary gland lymph nodes (SGLN) and tracheo-bronchial lymph nodes (TBLN) exhibit chemotaxis to SDF-1 (SDF) and human MEC (hMEC). Media or media containing 100 nM of SDF-1 (positive control) or 250 nM of hMEC was added to the bottom chamber of TRANSWELL plates (tissue culture plates fitted with TRANSWELL permeable tissue culture support devices), and media containing $2 \times 10^6$ cells isolated from the identified tissues was added to the top chamber. The plates were cultured for about 2 hours and the number of IgA antibody-secreting cells that migrated into the bottom chamber was determined using an ELISPOT assay. Percent migration is the number of IgA antibody-secreting cells which migrated in the presence of chemokine (either SDF-1 or hMEC) divided by the number of IgA antibody-secreting cells in the input cell population (determined separately using an ELISPOT assay), displayed as a percentage. n values indicate the number of assays that were performed for each tissue and the error bars represent standard error of the mean.

FIG. 14 is a histogram showing that IgA antibody-secreting cells (IgA ASC) from sheep red blood cell (SRBC)-inflamed mouse lung tissue exhibit chemotaxis to SDF-1 (SDF) and human MEC (MEC). Media or media containing 100 nM of SDF-1 (positive control) or 250 nM of human MEC was added to the bottom chamber of TRANSWELL plates (tissue culture plates fitted with TRANSWELL permeable tissue culture support devices), and media containing $2 \times 10^6$ cells isolated from SRBC-inflamed mouse lung tissue was added to the top chamber. The plates were cultured for about 2 hours and the number of IgA antibody-secreting cells that migrated into the bottom chamber was determined using an ELISPOT assay. Percent migration is the number of IgA antibody-secreting cells which migrated in the presence of chemokine (either SDF-1 or MEC) divided by the number of IgA antibody-secreting cells in the input cell population (determined separately using an ELISPOT assay), displayed as a percentage. The error bars represent standard error of the mean.

DETAILED DESCRIPTION OF THE INVENTION

Figure 1B:
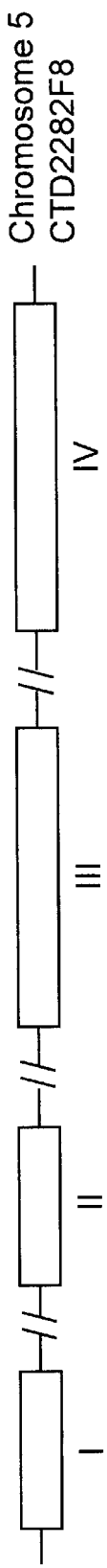
FIG. 1B is a schematic diagram showing the structure of a segment of human genomic DNA from chromosome 5 (bacterial artificial chromosome CTD-2282F8) which encodes MEC. The genomic DNA contains at least four exons which encode MEC. Exon I has the nucleotide sequence of nucleotides 1–116 of SEQ ID NO:1. Exon II has the nucleotide sequence of nucleotides 117–243 of SEQ ID NO:1. Exon III has the nucleotide sequence of nucleotides 244–495 of SEQ ID NO:1. Exon IV has the nucleotide sequence of nucleotides 495–739 of SEQ ID NO:1. The intron between exons I and II is greater than about 22,000 base pairs, the intron between exons II and III is about 6,285 base pairs, and the intron between exons III and IV is about 4857 base pairs. The nucleotide sequences of segments of the genomic DNA at the intron-exon junctions (e.g., 5' and 3' splice sites) of the cloned genomic DNA (bacterial artificial chromosome CTD-2282F8) are also illustrated (upper case letters represent bases that are part of the exons, lower case letters represent bases that are part of the introns). SEQ ID NO:3 illustrates the nucleotide sequence at the 5' end of exon I. SEQ ID NO:4 illustrates the nucleotide sequence of the 5' splice site found at the intron-exon junction at the 3' end of exon I. SEQ ID NO:5 illustrates the nucleotide sequence of the 3' splice site found at the intron-exon junction at the 5' end of exon II. SEQ ID NO:6 illustrates the nucleotide sequence of the 5' splice site found at the intron-exon junction at the 3' end of exon II. SEQ ID NO:7 illustrates the nucleotide sequence of the 3' splice site found at the intron-exon junction at the 5' end of exon III. SEQ ID NO:8 illustrates the nucleotide sequence of the 5' splice site found at the intron-exon junction at the 3' end of exon III. SEQ ID NO:9 illustrates the nucleotide sequence of the 3' splice site found at the intron-exon junction at the 5' end of exon IV. SEQ ID NO:10 illustrates the nucleotide sequence of the 5' splice site found at the intron-exon junction at the 5' end of exon IV.
Figure 1D:
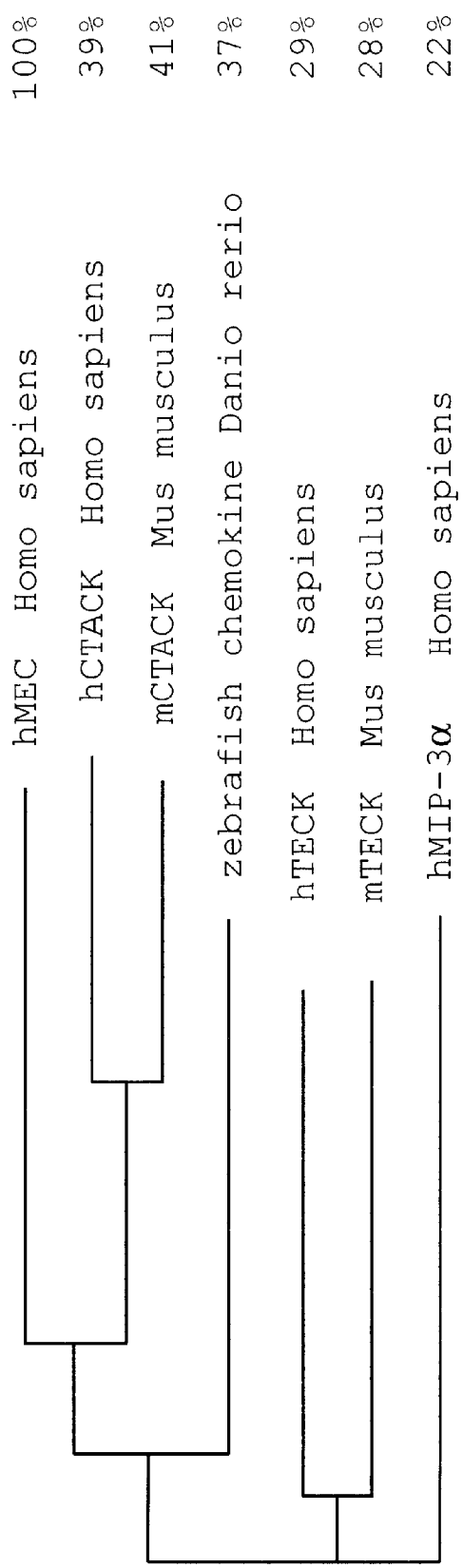
FIG. 1D is a dendrogram illustrating the relationship of human MEC (SEQ ID NO:2) to human CTACK, murine CTACK, human TECK, murine TECK, zebra fish (*Danio rerio*) CC chemokine CCL1 (GenBank Accession No. AF201450) and human MIP-3α (GenBank Accession No. D86955). Using ClustalW alignment analysis program, the protein sequences were aligned and the phylogenetic distances between the proteins were determined. The percent amino acid sequence identity in the overlapping homology regions of each chemokine, relative to the sequence of human MEC, is indicated.

Described herein is the identification and sequencing of a cDNA encoding a chemokine referred to herein as Mucosae-associated Epithelial Chemokine (MEC), which is also referred to as Dvic-1 (WO 98/23750) or CCL28 (Wang, W. et al, *J. Biol. Chem.*, 275:22313–22323 (2000)). Also described herein are receptor binding and chemotaxis studies, the results of which demonstrated that MEC is a novel ligand for C—C chemokine receptor 10 (CCR10; CCR10is also referred to as GPR-2 (see, e.g., Homey, B. et al., *J. Immunol*, 164:3465–3470 (2000)) and for C—C chemokine receptor 3 (CCR3), and that MEC is a chemoattractant for subsets of memory lymphocytes, as well as eosinophils. MEC was found to be expressed in mucosal tissues by, for example, mucosal epithelial cells. Analysis of cultured cell lines and laser capture microdissected epithelia revealed constitutive MEC expression by mucosal epithelial cells, but not endothelial cells, fibroblastic cells or lymphoid cells. The results of the studies described herein indicate that MEC plays an important role in the physiology and/or recruitment of specialized cells into mucosal tissues, including the respiratory mucosa, oral mucosa and colon.

The invention relates to the interaction of MEC with CCR3 or CCR10 and to agents (e.g., ligands, antibodies, antagonists, agonists, inhibitors, promoters) which alter said interaction. In one aspect, the invention relates to methods for detecting or identifying an agent (i.e., molecule or compound) which can modulate (inhibit (reduce or prevent) or promote) the binding of MEC to CCR3 and/or CCR10.

As used herein "mammalian CCR3" and "mammalian CCR10" refer to naturally occurring or endogenous mammalian CCR3 proteins (e.g., SEQ ID NO:16) and to naturally occurring or endogenous mammalian CCR10 proteins (e.g., SEQ ID NO:18, SEQ ID NO:20), respectively, and to proteins having an amino acid sequence which is the same as that of a naturally occurring or endogenous corresponding mammalian receptor (CCR3 or CCR10) protein (e.g., recombinant proteins, synthetic proteins (i.e., produced using the methods of synthetic organic chemistry)). Accordingly, as defined herein, the terms include mature receptor protein, polymorphic or allelic variants, and other isoforms of a mammalian CCR3 or CCR10 (e.g., produced by alternative splicing or other cellular processes), and modified or unmodified forms of the foregoing (e.g., lipidated, glycosylated, unglycosylated). Naturally occurring or endogenous mammalian CCR3 or CCR10 proteins include wild type proteins such as mature receptor, polymorphic or allelic variants and other isoforms which occur naturally in mammals (e.g., humans, non-human primates). Such proteins can be recovered or isolated from a source which naturally produces mammalian CCR3 or CCR10, for example. These proteins and mammalian receptor proteins having the same amino acid sequence as a naturally occurring or endogenous corresponding mammalian CCR3 or CCR10, are referred to by the name of the corresponding mammal. For example, where the corresponding mammal is a human, the protein is designated as a human CCR3 protein (e.g., a recombinant human CCR3 produced in a suitable host cell).

"Functional variants" of mammalian CCR3 or CCR10 proteins include functional fragments, functional mutant proteins, and/or functional fusion proteins which can be produced using suitable methods (e.g., mutagenesis (e.g., chemical mutagenesis, radiation mutagenesis), recombinant DNA techniques). A "functional variant" is a protein or polypeptide which has at least one function characteristic of a mammalian CCR3 or CCR10 protein as described herein, such as MEC-binding, a signaling activity and/or ability to stimulate a cellular response. Preferred functional variants can bind MEC (e.g., naturally occurring mammalian MEC) and signal (e.g., MEC-induced $Ca^{2+}$ flux) or stimulate a cellular response (e.g., MEC-induced chemotaxis).

Generally, fragments or portions of mammalian CCR3 or CCR10 proteins include those having a deletion (i.e., one or more deletions) of an amino acid (i.e., one or more amino acids) relative to the mature mammalian CCR3 or CCR10 protein (such as N-terminal, C-terminal or internal deletions). Fragments or portions in which only contiguous amino acids have been deleted or in which non-contiguous amino acids have been deleted relative to mature mammalian CCR3 or CCR10 protein are also envisioned.

Mutant mammalian CCR3 or CCR10 proteins include natural or artificial variants of a mammalian CCR3 or CCR10 proteins differing by the addition, deletion and/or substitution of one or more contiguous or non-contiguous amino acid residues (e.g., receptor chimeras). Such mutations can occur at one or more sites on a protein, such as a conserved region or nonconserved region (compared to other chemokine receptors or G-protein coupled receptors), extracellular region, cytoplasmic region, or transmembrane region.

Fusion proteins encompass polypeptides comprising a mammalian CCR3 or CCR10 (e.g., human CCR3 or human CCR10) or variants thereof (e.g., MEC-binding variant) as a first moiety, linked via a covalent bond (e.g., a peptide bond) to a second moiety not occurring in the mammalian CCR3 or CCR10 as found in nature. Thus, the second moiety can be an amino acid, oligopeptide or polypeptide. The second moiety can be linked to the first moiety at a suitable position, for example, the N-terminus, the C-terminus or internally. In one embodiment, the fusion protein comprises an affinity ligand (e.g., an enzyme, an antigen, epitope label (tag)(e.g., a hemagglutinin (HA) epitope (e.g., influenza virus HA epitope, YPYDVPDYA; SEQ ID NO:24)), a binding domain) as the first moiety, and a second moiety comprising a linker sequence and human CCR3 or portion thereof, or human CCR10 or portion thereof. Additional (e.g., third, fourth) moieties can be present as appropriate.

"Functional variants" of mammalian CCR3 or CCR10 proteins, such as MEC-binding variant CCR3 and MEC-binding variant CCR10 proteins, also include proteins and polypeptides in which one or more naturally occurring amino acid residues are conservatively substituted. A conservative amino acid substitution refers to the replacement of a first amino acid by a second amino acid that has chemical and/or physical properties (e.g., charge, structure, polarity, hydrophobicity/hydrophilicity) which are similar to those of the first amino acid. Groups of amino acids with similar chemical and/or physical properties are known in the art and include, for example, those with hydrophilic side chains (e.g., asparagine, glutamine, serine, threonine, tyrosine, lysine, arginine, histidine, aspartate, glutamate), hydrophobic side chains (e.g., alanine, valine, leucine, isoleucine, proline, phenylalanine, tryptophan, methionine, cysteine, glycine), acidic side chains (e.g., aspartate, glutamate), basic side chains (e.g., lysine, arginine, histidine), aromatic side chains (e.g., phenylalanine, tryptophan, histidine, tyrosine) and nucleophilic side chains (e.g., cysteine, serine, threonine). In one embodiment, a functional variant of mammalian CCR3 or CCR10 (e.g., a MEC-binding variant) shares at least about 80% amino acid sequence similarity or identity with a naturally occurring mammalian CCR3 or CCR10, preferably at least about 90% amino acid sequence similarity or identity, and more preferably at least about 95% amino acid sequence similarity or identity with said naturally occurring mammalian CCR3 or CCR10. In another embodiment, a functional fusion protein comprises a first moiety which shares at least about 80% sequence similarity or identity with a naturally occurring mammalian CCR3 or CCR10, preferably at least about 90% sequence similarity or identity, and more preferably at least about 95% sequence similarity or identity with a naturally occurring mammalian CCR3 or CCR10 (e.g., a human CCR3 (e.g., SEQ ID NO:16), a human CCR10 (e.g., SEQ ID NO:18, SEQ ID NO:20). Amino acid sequence similarity and amino acid sequence identity can be determined using a suitable sequence alignment algorithm, such as the Lasergene system (DNASTAR, Inc., Madison, Wis.), using the Clustal method with the PAM 250 residue weight table, a gap penalty of 10, a gap length penalty of 10 and default parameters (pairwise alignment parameters: ktuple=1, gap penalty=3, window=4 and diagonals saved=5). In one embodiment, a mammalian CCR3 or CCR10 or portion thereof is encoded by a nucleic acid sequence which is different from a naturally-occurring nucleic acid sequence, but which, due to the degeneracy of the genetic code, encodes mammalian CCR3 or CCR10 or a portion thereof.

In one embodiment, the MEC-binding variant of CCR3 or CCR10 is a recombinant protein that has been designed to bind MEC. Generally, such MEC-binding variant proteins can comprise one or more of the extracellular domains or ligand-binding portion thereof of CCR3 or CCR10. For example, the MEC-binding variant can be a recombinant 7-transmembrane spanning G-protein coupled receptor wherein the amino acid sequence of one or more of the extracellular domains is at least about 80% similar or identical to the amino acid sequence of the corresponding extracellular domain of CCR3 or CCR10, preferably at least about 90% similar or identical to the amino acid sequence of the corresponding extracellular domain of CCR3 or CCR10, more preferably at least about 95% similar or identical to the amino acid sequence of the corresponding extracellular domain of mammalian CCR3 or CCR10 (e.g., a human CCR3 (e.g., SEQ ID NO:16), a human CCR10 (e.g., SEQ ID NO:18, SEQ ID NO:20)). A number of 7-transmembrane spanning G-protein coupled receptors, such as chemokine receptors, are known in the art and can be used as a scaffold for preparing such a MEC-binding recombinant protein. For example, a nucleic acid encoding human C—C chemokine receptor 1 (CCR1) can be altered by replacing the sequences encoding the amino terminal extracellular domain, first extracellular loop, second extracellular loop and/or third extracellular loop with the corresponding sequences which encode these regions of a naturally occurring human CCR3 or CCR10, and the nucleic acid can be expressed to produce a recombinant receptor that binds MEC. Such receptors and nucleic acids encoding the receptors can be prepared using any suitable method, for example as described in Pease, J. E., et al, *J. Biol. Chem.*, 273:19972–19976 (1998), the entire teachings of which are incorporated herein by reference.

As used herein "mammalian Mucosae-associated Epithelial Chemokine" or "mammalian MEC" refers to naturally occurring or endogenous mammalian MEC proteins (e.g., SEQ ID NO:2, amino acid residues 21–127 of SEQ ID NO:2) and to proteins having an amino acid sequence which is the same as that of a naturally occurring or endogenous corresponding mammalian MEC protein (e.g., recombinant proteins, synthetic proteins (i.e., produced using the methods of synthetic organic chemistry)). Accordingly, as defined herein, the term includes mature protein, polymorphic or allelic variants, and other isoforms of a mammalian MEC (e.g., produced by alternative splicing, proteolytic processing or other cellular processes), and modified or unmodified forms of the foregoing (e.g., lipidated, glycosylated (e.g., with glycosaminoglycans), unglycosylated). Naturally occurring or endogenous mammalian MEC proteins include wild type MEC, polymorphic or allelic variants and other isoforms which occur naturally in mammals (e.g., humans, non-human primates). Such proteins can be recovered or isolated from a source which naturally produces mammalian MEC, for example. These proteins and mammalian MEC proteins having the same amino acid sequence as a naturally occurring or endogenous corresponding mammalian MEC, are referred to by the name of the corresponding mammal. For example, where the corresponding mammal is a human, the protein is designated as a human MEC protein (e.g., a recombinant human MEC produced in a suitable host cell).

"Receptor-binding variants" of mammalian MEC proteins include CCR3-binding and CCR10-binding fragments (e.g., proteolytic fragments), receptor-binding mutant proteins and receptor-binding fusion proteins which can be produced using suitable methods (e.g., mutagenesis (e.g., chemical mutagenesis, radiation mutagenesis), recombinant DNA techniques). A "receptor-binding variant" can be identified using a suitable receptor-binding assay such as a CCR3 or CCR10 binding assay. In one embodiment, the receptor-binding variant MEC can bind mammalian CCR3 and/or CCR10 and thereby induce signaling (e.g., a transient increase in the concentration of intracellular free calcium ions ($[Ca^{2+}]_i$) ($Ca^{2+}$ flux)) or a cellular response (e.g., chemotaxis).

Generally, fragments or portions of mammalian MEC proteins include those having a deletion (i.e., one or more deletions) of an amino acid (i.e., one or more amino acids) relative to the mature mammalian MEC protein (such as N-terminal, C-terminal or internal deletions). Fragments or portions in which only contiguous amino acids have been deleted or in which non-contiguous amino acids have been deleted relative to mature mammalian MEC protein are also envisioned.

Mutant mammalian MEC proteins include natural or artificial variants of a mammalian MEC protein differing by the addition, deletion and/or substitution of one or more contiguous or non-contiguous amino acid residues. Such mutations can occur at one or more sites on a protein, for example a conserved region or nonconserved region (compared to other chemokines).

Fusion proteins encompass polypeptides comprising a mammalian MEC (e.g., human MEC) or a receptor-binding variant thereof as a first moiety, linked via a covalent bond (e.g., a peptide bond) to a second moiety not occurring in the mammalian MEC or variant as found in nature. Thus, the second moiety can be an amino acid, oligopeptide or polypeptide. The second moiety can be linked to the first moiety at a suitable position, for example, the N-terminus, the C-terminus or internally. In one embodiment, the fusion protein comprises an affinity ligand (e.g., an enzyme, an antigen, epitope tag, a binding domain) as the first moiety, and a second moiety comprising a linker sequence and human MEC or a portion thereof. Additional (e.g., third, fourth) moieties can be present as appropriate.

Receptor-binding variants of mammalian MEC also include proteins and polypeptides in which one or more naturally occurring amino acid residues are conservatively substituted. In one embodiment, the receptor-binding variant of mammalian MEC shares at least about 80% sequence similarity or identity with a naturally occurring mammalian MEC (e.g., SEQ ID NO:2), preferably at least about 90% sequence similarity or identity with a naturally occurring mammalian MEC, and more preferably at least about 95% sequence similarity or identity with a corresponding naturally occurring mammalian MEC. In another embodiment, a functional fusion protein comprises a first moiety which shares at least about 80% sequence similarity or identity with a naturally occurring mammalian MEC, preferably at least about 90% sequence similarity or identity, and more preferably at least about 95% sequence similarity or identity with a naturally occurring mammalian MEC. Variants can be prepared using any suitable method, (e.g., solid phase peptide synthesis, by expression of nucleic acids encoding the variant), and tested for receptor binding.

A composition comprising a mammalian CCR3 or functional variant thereof (e.g., MEC-binding variant) and/or a mammalian CCR10 or functional variant thereof (e.g., MEC-binding variant) can be used in a binding assay to detect and/or identify agents that can inhibit binding of MEC to receptor. Compositions suitable for use in a binding assay include, for example, cells which naturally express a mammalian CCR3 and/or CCR10 or functional variant thereof. For example, eosinophils which express CCR3 or melanocytes, dermal fibroblasts or skin-derived Langerhans cells which express CCR10 (Homey, B., et al, *J. Immunol.*, 164:3465–3470 (2000)) can be used. Recombinant cells comprising an exogenous nucleic acid sequence which encodes a mammalian CCR3 or functional variant thereof or CCR10 or functional variant thereof are also suitable for use in a binding assay. Compositions suitable for use in a binding assay also include, membrane preparations which comprise a mammalian CCR3 or functional variant thereof and/or a mammalian CCR10 or functional variant thereof. Such membrane preparations can contain natural (e.g., plasma membrane) or synthetic membranes. Preferably, the membrane preparation is a membrane fraction of a cell that expresses a mammalian CCR3 or a functional variant thereof or a mammalian CCR10 or a functional variant thereof. In one embodiment, paramagnetic proteoliposomes which contain a mammalian CCR3 or a functional variant thereof or a mammalian CCR10 or a functional variant thereof can be used (see, for example, Mirzabekov, T. et al, *Nature Biotechnology*, 18:649–654 (2000)).

Binding Assays

In one embodiment, the method of detecting or identifying an agent that can modulate the binding of MEC to CCR3 and/or CCR10 is a competitive binding assay in which the capacity of a test agent to inhibit or promote the binding of MEC (e.g., a naturally occurring mammalian MEC (e.g., SEQ ID NO:2, amino acid residues 23–127 of SEQ ID NO:2)) is assessed. For example, MEC can be labeled with a suitable label as described herein, and the amount of labeled MEC required to saturate the CCR3 and/or CCR10 present in the assay can be determined. A saturating amount or non-saturating amount (e.g., amount sufficient to occupy about 5% to about 10% of receptors) of labeled MEC and various amounts of a test agent can be contacted with a composition comprising a mammalian CCR3 (e.g., a naturally occurring mammalian CCR3 (e.g., SEQ ID NO:15) or functional variant thereof and/or a mammalian CCR10 (e.g., a naturally occurring mammalian CCR10 (e.g., SEQ ID NO:18, SEQ ID NO:20)) or functional variant thereof under conditions suitable for binding, and complex formation determined. In this type of assay, a decrease in the amount of complex formed between the labeled MEC and receptor (CCR3 and/or CCR10) or functional variant thereof indicates that the test agent inhibits the binding of MEC to CCR3 and/or CCR10.

Agents which promote the binding of MEC to CCR3 and/or CCR10 (e.g., agonists of MEC-induced CCR3 and/or CCR10 function) can be identified, for example, by contacting a non-saturating amount of labeled MEC and a test agent with a composition comprising a mammalian CCR3 (e.g., a naturally occurring mammalian CCR3 (e.g., SEQ ID NO:15) or functional variant thereof and/or a mammalian CCR10 (e.g., a naturally occurring mammalian CCR10 (e.g., SEQ ID NO:18, SEQ ID NO:20)) or functional variant thereof under conditions suitable for binding, and complex formation determined. In this type of assay, an increase in the amount of complex formed between the labeled MEC and receptor (CCR3 and/or CCR10) or functional variant thereof indicates that the test agent augments the binding of MEC to CCR3 and/or CCR10.

The formation of a complex between MEC and receptor or functional variant thereof can be detected or measured directly or indirectly using any suitable method. For example, MEC can be labeled with a suitable label and the formation of a complex can be determined by detection of the label. The specificity of the complex can be determined using a suitable control such as excess unlabeled MEC or label alone. Labels suitable for use in detection of a complex between MEC and a mammalian CCR3 or functional variant thereof and/or a mammalian CCR10 or functional variant thereof include, for example, a radioisotope, an epitope label (tag)(e.g., a hemagglutinin (HA) epitope (e.g., SEQ ID NO:24)), an affinity label (e.g., biotin, avidin), a spin label, an enzyme label, a fluorescent group or a chemiluminescent group. When labels are not employed, complex formation can be determined by surface plasmon resonance or other suitable methods.

The capacity of the test agent to inhibit the formation of a complex between MEC and a mammalian receptor (e.g., CCR3, CCR10) can be reported as the concentration of test agent required for 50% inhibition ($IC_{50}$ values) of specific binding of labeled MEC. Specific binding is preferably defined as the total binding (e.g., total label in complex) minus the non-specific binding. Non-specific binding is preferably defined as the amount of label detected in complexes formed in the presence of excess unlabeled MEC.

Functional Assays

Functional assays can be used to detect and identify agents that modulate binding of MEC to CCR3 and/or CCR10 and/or which modulate the function of CCR3 and/or CCR10 upon MEC binding (e.g., MEC-induced signaling or activation). An agent can be studied in one or more suitable functional assays to determine if said agent can modulate (inhibit (reduce or prevent) or promote) one or more signaling activities or cellular responses induced upon binding of MEC to CCR3 or CCR10. For example, an agent can be tested in an extracellular acidification assay, calcium flux assay, ligand binding assay, chemotaxis assay or assay which monitors degranulation or inflammatory mediator release (see, for example, Hesselgesser et al., *J. Biol. Chem.* 273(25):15687–15692 (1998) and WO 98/02151). Functional assays can also be used to detect and identify agents which modulate (e.g., inhibit) signaling or cellular responses induced upon binding of MEC to CCR3 or CCR10 (e.g., antagonists of MEC-induced function of CCR3 and/or CCR10, agonists of MEC-induced function of CCR3 and/or CCR10).

For example, an agent (e.g., an antibody which binds to a mammalian CCR3 or mammalian CCR10) can be tested in a leukocyte chemotaxis assay using suitable cells. Suitable cells include, for example, cell lines, recombinant cells or isolated cells which express a mammalian CCR3 or CCR10 and undergo MEC-induced chemotaxis. For example, eosinophils or CCR3-expressing recombinant L1/2 cells (see Campbell, et al. *J. Cell. Biol*, 134:255–266 (1996) regarding L1/2 cells), can be used in a modification of a transendothelial migration assay (Ponath, P. D. et al, *J. Exp. Med.*, 183:2437–2448 (1996); Carr, M. W., et al. T. A., *Proc. Natl Acad. Sci., USA*, 91:3652 (1994)). The endothelial cell line, ECV304 (Takahashi, K et al., *In Vitro Cell Dev. Biol.*, 26(3 Pt 1):265–274 (1990); available from European Collection of Animal Cell Cultures (Reference No: 92091712), Salisbury, United Kingdom)) can be used. Endothelial cells can be cultured on 6.5 mm diameter TRANSWELL culture inserts (Costar Corp., Cambridge, Mass.) having a pore size of about 3.0–5.0 $\mu$m. Culture media for the ECV 304 cells can consist of equal parts RPMI 1640 and M199 with 10%

FCS, L-glutamine, and antibiotics. The assay media can consist of equal parts RPMI 1640 and M199 with 1–3% FCS. About 24 hours to about 1 week before the assay, $2 \times 10^5$ ECV 304 cells can be plated onto each insert of the 24 well TRANSWELL plate (tissue culture plates fitted with TRANSWELL permeable tissue culture support devices) and incubated at 37° C. MEC can be added to the 24-well tissue culture plates in a final volume of 600 μL. Endothelial-coated TRANSWELLs (permeable tissue culture support devices) can be inserted into each well and $10^6$ cells of the cell type being studied can be added to the top chamber in a final volume of 100 μL of assay medium. The plate can then be incubated at 37° C. in 5% $CO_2$/95% air for about 1–2 hours (e.g., for primary cells) or for up to about 18 hours (e.g., for transfected cells). The cells that migrate to the bottom chamber during incubation can be counted, for example using flow cytometry. To count cells by flow cytometry, 500 μL of the cell suspension from the lower chamber can be placed in a tube and relative counts can obtained for a set period of time, for example, 30 seconds. This counting method is highly reproducible and allows gating on the leukocytes and the exclusion of debris or other cell types from the analysis. Other methods of counting the migrated cells can be used, for example, cells can be counted manually using a microscope. Assays to evaluate agents that can inhibit or enhance MEC-induced chemotaxis can be performed in the same way as the control experiment described above, except that agent solutions, in assay media containing up to 1% of DMSO co-solvent, can be added to both the top and bottom chambers prior to addition of the cells. The capacity of an agent to inhibit or promote chemotaxis can be determined by comparing the number of cell that migrate to the bottom chamber in wells which contain the agent, to the number of cells which migrate to the bottom chamber in control wells. Control wells can contain equivalent amounts of DMSO, but no agent. If desired, the endothelial cells can be omitted from the described chemotaxis assay and ligand-induced migration across the TRANSWELL insert can be measured.

An agent can also be assessed by monitoring cellular responses induced upon MEC binding to CCR3 or CCR10, using suitable cells which express a mammalian CCR3 or a functional variant thereof or a mammalian CCR10 or a functional variant thereof. For instance, exocytosis (e.g., degranulation of cells leading to release of one or more enzymes or other granule components, such as esterases (e.g., serine esterases), perforin, and/or granzymes), inflammatory mediator release (such as release of bioactive lipids such as leukotrienes (e.g., leukotriene $C_4$)), and respiratory burst, can be monitored by methods known in the art or other suitable methods (see e.g., Taub, D. D. et al., *J. Immunol.*, 155: 3877–3888 (1995), regarding assays for release of granule-derived serine esterases; Loetscher et al., *J. Immunol.*, 156: 322–327 (1996), regarding assays for enzyme and granzyme release; Rot, A. et al., *J. Exp. Med.*, 176: 1489–1495 (1992) regarding respiratory burst; Bischoff, S. C. et al., *Eur. J. Immunol.*, 23: 761–767 (1993) and Baggliolini, M. and C. A. Dahinden, *Immunology Today*, 15: 127–133 (1994)). A variety of functional assays which employ cells which express a mammalian CCR3 or functional variant thereof and/or a mammalian CCR10 or functional variant thereof can be employed (e.g., recombinant cells). For example, assays in which expression of an endogenous or exogenous reporter gene (e.g., β-galactosidase, green fluorescent protein) is induced upon MEC binding to receptor (CCR3, CCR10) or variant expressed by recombinant cells (e.g., recombinant bacteria, recombinant yeast, recombinant mammalian cells) can be used.

In one embodiment, an agent that can inhibit or promote a receptor-mediated function or response (e.g., signaling activity, chemotaxis) induced upon MEC binding to CCR3 or CCR10 is identified by monitoring the release of an enzyme upon degranulation or exocytosis by a cell capable of this function. For example, cells expressing a mammalian CCR3 or a functional variant thereof (e.g., human eosinophils) can be maintained in a suitable medium under suitable conditions, and degranulation can be induced. The cells are contacted with an agent to be tested, and release of granule components (e.g., enzymes (e.g., peroxidase, serine proteases, serine esterases, histaminase, kininase, lysophospholipase, aryl sulfatase (e.g., A type and/or B type), phospholipase D), major basic protein (MBP), histamine) can be assessed. The release of granule components into the medium can be detected or measured using a suitable assay, such as an immunological assay (see, for example, Egesten, A. et al., *Allergy*, 53(11):1066–1073 (1998)), or biochemical assay for enzyme activity.

The medium can be assayed directly, by introducing components of the assay (e.g., substrate, co-factors, antibody) into the medium (e.g., before, simultaneous with or after the cells and agent are combined). The assay can also be performed on medium which has been separated from the cells or further processed (e.g., fractionated) prior to assay. For example, convenient assays are available for enzymes, such as serine esterases (see e.g., Taub, D. D. et al., *J. Immunol.*, 155: 3877–3888 (1995) regarding release of granule-derived serine esterases).

In another embodiment, cells expressing a mammalian CCR3 or a functional variant thereof or CCR10 or a functional variant thereof are combined with MEC, an agent to be tested is added before, after or simultaneous therewith, and $Ca^{2+}$ flux is assessed. Inhibition of ligand-induced $Ca^{2+}$ flux is indicative that the agent inhibits MEC binding and/or signaling through CCR3 and/or CCR10. A variety of suitable assays for assessing $Ca^{2+}$ flux are available (see, for example, Hauser, C. J., *Surgery*, 126(2):208–215 (1999); Kumae, T., *Luminescence*, 14(6):375–381 (1999); Hesselgesser et al., *J. Biol. Chem.* 273(25):15687–15692 (1998)).

Engagement of the chemokine receptors of a lymphocyte can cause integrin activation, and induction of adherence to adhesion molecules expressed in vasculature or the perivascular space. Cellular adherence can be monitored by methods known in the art or other suitable methods. In one embodiment, an agent that inhibits binding of MEC to CCR3 and/or CCR10 is identified by monitoring cellular adherence by a cell capable of adhesion. For example, an agent to be tested can be combined with (a) cells expressing a mammalian CCR3 or functional variant thereof or CCR10 or functional variant thereof (preferably non-adherent cells which when transfected with receptor and stimulated with MEC acquire adhesive ability), (b) a composition comprising a suitable adhesion molecule (e.g., a substrate such as a culture well coated with an adhesion molecule, such as fibronectin), and (c) MEC, and maintained under conditions suitable for MEC-induced adhesion. Labeling of cells with a fluorescent dye provides a convenient means of detecting adherent cells. Nonadherent cells can be removed (e.g., by washing) and the number of adherent cells determined. The effect of the agent in inhibiting or enhancing ligand- or promoter-induced adhesion can be indicative of inhibitor or promoter activity, respectively. Agents active in the assay include inhibitors and promoters of binding, signaling, and/ or cellular responses. In another embodiment, an agent to be tested can be combined with cells expressing a mammalian CCR3 or a functional variant thereof or a mammalian CCR10 or a functional variant thereof and a composition comprising a suitable adhesion molecule under conditions suitable for MEC-induced adhesion, and adhesion is monitored. Decreased adhesion relative to a suitable control is indicative of the presence of an inhibitor.

The binding assays and functional assays described above can be used, alone or in combination with each other or other suitable methods, to detect or identify agents which modulate binding of MEC to CCR3 and/or CCR10 and/or modulators (antagonists, agonists) of a cellular function (e.g., signaling, activation, chemotaxis) induced upon binding of MEC to CCR3 or CCR10. The in vitro methods of the present invention can be adapted for high-throughput screening in which large numbers of samples are processed (e.g., a 96-well format). In one embodiment, recombinant cells expressing mammalian CCR3 or a MEC-binding variant thereof and/or mammalian CCR10 or a MEC-binding variant thereof can be used and MEC-induced intracellular calcium mobilization can be monitored using a fluorometric imaging plate reader (FLIPR)(see, for example, Coward, P., et al, $Anal.\ Biochem.$, 270:242–248 (1999)). Other suitable assays can monitor complex formation between MEC, for example, using time-resolved fluorescence or fluorometric microvolume assay technology (FMAT)(see, e.g., Kane, S. A. et al., $Anal.\ Biochem.$, 278(1):29–38 (2000), Degan, P. et al., $Mol.\ Biotechnol.$, 13(3):215–222 (1999) and Saarinen, K. et al., $J.\ Immunol.\ Methods$, 236(1–2): 19–26 (2000) regarding time-resolved fluorescence; Miraglia, S. et al., $J.\ Biomol.\ Screen$, 4(4):193–204 (1999), regarding FMAT). Cells expressing a mammalian CCR3 or a functional variant thereof or a mammalian CCR10 or a functional variant thereof at levels suitable for high-throughput screening can be used, and thus, are valuable in the identification and/or isolation of agents which modulate binding of MEC to CCR3 and/or CCR10 and/or modulator cellular functions (e.g., signaling, chemotaxis) induced upon binding of MEC to CCR3 or CCR10. Expression of receptor (CCR3, CCR10) or a variant thereof can be monitored in a variety of ways. For instance, expression can be monitored using antibodies which bind receptor or a portion thereof or using a suitable ligand (e.g., MEC). Also, commercially available antibodies (e.g., mAB HA.11 which binds the influenza hemagglutinin epitope (SEQ ID NO 24); BAbCO, Richmond, Calif.) can be used to detect expression of an antigen- or epitope-tagged receptor protein or polypeptide (e.g., influenza virus HA epitope-(e.g., SEQ ID NO: 24) tagged receptors, FLAG-tagged receptors), and cells expressing epitope-labeled receptor at the desired level can be selected (e.g., by fluorescence activated cell sorting).

A variety of agents, such as proteins (e.g., antibodies and antigen-binding fragments thereof), peptides, peptidomimetics, small organic molecules, nucleic acids and the like, can be tested for the capacity to inhibit the binding of MEC to CCR3 and/or CCR10. According to the method of the present invention, agents can be individually screened or one or more agents can be tested simultaneously. Where a mixture of compounds is tested, the compounds selected by the processes described can be separated (as appropriate) and identified using suitable methods (e.g., sequencing, chromatography). The presence of one or more compounds (e.g., a ligand, inhibitor, promoter) in a test sample can also be determined according to these methods.

Agents which modulate binding of MEC to CCR3 and/or CCR10 and/or which modulate the function of CCR3 and/or CCR10 upon MEC binding (e.g., MEC-induced signaling or activation) can be used in the therapeutic methods described herein and can be identified, for example, by screening libraries or collections of molecules, such as, the Chemical Repository of the National Cancer Institute, in assays described herein or using other suitable methods. Combinatorial libraries of compounds (e.g., organic compounds, recombinant or synthetic peptides, "peptoids", nucleic acids) produced by combinatorial chemical synthesis or other methods can be tested (see e.g., Zuckerman, R. N. et al., $J.\ Med.\ Chem.$, 37: 2678–2685 (1994) and references cited therein; see also, Ohlmeyer, M. H. J. et al., $Proc.\ Natl.\ Acad.\ Sci.\ USA$ 90:10922–10926 (1993) and DeWitt, S. H. et al., $Proc.\ Natl.\ Acad.\ Sci.\ USA$ 90:6909–6913 (1993), relating to tagged compounds; Rufter, W. J. et al. U.S. Pat. No. 5,010,175; Huebner, V. D. et al., U.S. Pat. No. 5,182,366; and Geysen, H. M., U.S. Pat. No. 4,833,092). Where compounds selected from a combinatorial library by the present method carry unique tags, identification of individual compounds by chromatographic methods is possible.

In one embodiment, the agent or agents tested and/or identified according to the methods of the invention do not comprise viruses or viral proteins (e.g., viral envelope proteins). In another embodiment, the agent or agents tested and/or identified according to the methods of the invention do not comprise chemokines or mutants or analogues thereof. For example, the agent or collection of agents tested according to the methods of the invention can exclude mutant chemokines having an amino-terminal deletion (see, for example, U.S. Pat. No. 5,739,103 regarding such mutants). In another embodiment, the agent or agents tested and/or identified according to the methods of the invention do not comprise immunoglobulins (antibodies) or antigen-binding fragments thereof (e.g., antibodies or antigen-binding fragments which have binding specificity for human CCR3, human CCR10 and/or human MEC).

The invention also relates to a method of identifying or isolating an agent (i.e., molecule or compound) which can be used in therapy (e.g., in treating a subject having an inflammatory disease), as described herein. In one embodiment, the agent is identified or isolated in a competitive binding assay as described above. In another embodiment, the method is a method of identifying or isolating an agent for use in inhibiting a cellular response to ligand (e.g., MEC) binding to CCR3 and/or CCR10 on the surface of a cell (e.g., leukocytes, such as eosinophils and T cells).

Agents that modulate (promote, inhibit) the binding of MEC to other receptors can be identified by suitable modification of the methods described herein. For example, a recombinant cell that expresses a desired receptor can be used in a binding assay or functional assay as described herein.

Antibodies and Antibody Producing Cells

The invention relates to immunoglobulins (antibodies) which bind to mammalian CCR3, CCR10 or MEC and inhibit the binding of MEC to CCR3 and/or CCR10. The antibody of the invention can be polyclonal or monoclonal, and the term "antibody" is intended to encompass both polyclonal and monoclonal antibodies. The terms polyclonal and monoclonal refer to the degree of homogeneity of an antibody preparation, and are not intended to be limited to particular methods of production. The term "antibody" as used herein also encompasses functional fragments of antibodies, including fragments of chimeric, human, humanized, primatized, veneered or single chain antibodies. Functional fragments including antigen-binding fragments, including, but not limited to Fv, Fab, Fab' and F(ab')$_2$ fragments are encompassed by the invention. Such fragments can be produced by enzymatic cleavage or by recombinant techniques. For example, papain or pepsin cleavage can generate Fab or F(ab')$_2$ fragments, respectively. Other proteases with the requisite substrate specificity can also be used to generate Fab or F(ab')$_2$ fragments. Antibodies can also be produced in a variety of truncated forms using antibody genes in which one or more stop codons has been introduced upstream of the natural stop site. For example, a chimeric gene encoding a F(ab')$_2$ heavy chain portion can be designed to include DNA sequences encoding the $CH_1$ domain and hinge region of the heavy chain.

Single chain antibodies, and chimeric, humanized or primatized (CDR-grafted), or veneered antibodies comprising portions derived from different species, and the like are also encompassed by the present invention and the term "antibody". The various portions of these antibodies can be joined together chemically by conventional techniques, or can be prepared as a contiguous protein using recombinant DNA technology. For example, nucleic acids encoding a chimeric or humanized chain can be expressed to produce a contiguous protein. See, e.g., Cabilly et al., U.S. Pat. No. 4,816,567; Cabilly et al, European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al, European Patent No. 0,194,276 B1; Winter, U.S. Pat. No. 5,225,539; Winter, European Patent No. 0,239,400 B1; Queen et al., European Patent No. 0 451 216 B1; and Padlan, E. A. et al., EP 0 519 596 A1. See also, Newman, R. et al., *BioTechnology*, 10: 1455–1460 (1992), regarding primatized antibody, and Ladner et al., U.S. Pat. No. 4,946,778 and Bird, R. E. et al., *Science*, 242: 423–426 (1988)) regarding single chain antibodies.

Humanized antibodies can be produced using synthetic or recombinant DNA technology using standard methods or other suitable techniques. Nucleic acid (e.g., cDNA) sequences coding for humanized variable regions can also be constructed using PCR mutagenesis methods to alter DNA sequences encoding a human or humanized chain, such as a DNA template from a previously humanized variable region (see e.g., Kamman, M., et al., *Nucl. Acids Res.*, 17: 5404 (1989)); Sato, K., et al., *Cancer Research*, 53: 851–856 (1993); Daugherty, B. L. et al., *Nucleic Acids Res.*, 19(9): 2471–2476 (1991); and Lewis, A. P. and J. S. Crowe, *Gene*, 101: 297–302 (1991)). Using these or other suitable methods, variants can also be readily produced. In one embodiment, cloned variable regions can be mutated, and sequences encoding variants with the desired specificity can be selected (e.g., from a phage library; see e.g., Krebber et al., U.S. Pat. No. 5,514,548; Hoogenboom et al., WO 93/06213, published Apr. 1, 1993).

Antibodies which are specific for mammalian (e.g., human) CCR3 or mammalian (e.g., human) CCR10 or mammalian (e.g., human) MEC can be raised against an appropriate immunogen. For example, antibodies which specifically bind mammalian CCR3, such as isolated and/or recombinant human CCR3 or portions thereof (including synthetic molecules, such as synthetic peptides), can be raised. Antibodies can also be raised by immunizing a suitable host (e.g., mouse) with cells that express CCR3 and/or CCR10, such as eosinophils or skin-derived Langerhans cells. In addition, cells expressing a recombinant mammalian CCR3 or CCR10, such as transfected cells, can be used as immunogens or in a screen for antibody which binds thereto (See e.g., Chuntharapai et al., *J. Immunol.*, 152: 1783–1789 (1994); Chuntharapai et al., U.S. Pat. No. 5,440,021).

Preparation of immunizing antigen, and polyclonal and monoclonal antibody production can be performed using any suitable technique. A variety of methods have been described (see e.g., Kohler et al., *Nature*, 256: 495–497 (1975) and *Eur. J. Immunol.* 6: 511–519 (1976); Milstein et al., *Nature* 266: 550–552 (1977); Koprowski et al., U.S. Pat. No. 4,172,124; Harlow, E. and D. Lane, 1988, *Antibodies: A Laboratory Manual*, (Cold Spring Harbor Laboratory: Cold Spring Harbor, N.Y.); *Current Protocols In Molecular Biology*, Vol. 2 (Supplement 27, Summer '94), Ausubel, F. M. et al., Eds., (John Wiley & Sons: New York, N.Y.), Chapter 11, (1991)). Where monoclonal antibodies are desired, a hybridoma is generaly produced by fusing a suitable immortal cell line (e.g., a myeloma cell line such as SP2/0, P3X63Ag8.653 or a heteromyeloma) with antibody producing cells. Antibody producing cells can be obtained from the peripheral blood or, preferably the spleen or lymph nodes, of humans or other suitable animals immunized with the antigen of interest. The fused cells (hybridomas) can be isolated using selective culture conditions, and cloned by limiting dilution. Cells which produce antibodies with the desired specificity can be selected by a suitable assay (e.g., ELISA).

Other suitable methods of producing or isolating antibodies of the requisite specificity can be used, including, for example, methods which select recombinant antibody from a library (e.g., a phage display library). Transgenic animals capable of producing a repertoire of human antibodies (e.g., XenoMouse® (Abgenix, Fremont, Calif.)) can be produced using suitable methods (see e.g., Jakobovits et al., *Proc. Natl. Acad. Sci. USA*, 90: 2551–2555 (1993); Jakobovits et al., *Nature*, 362: 255–258 (1993)). Additional methods which are suitable for production of transgenic animals capable of producing a repertoire of human antibodies have been described (e.g., Lonberg et al., U.S. Pat. No. 5,545,806; Surani et al., U.S. Pat. No. 5,545,807; Lonberg et al., WO97/13852).

In one embodiment, the invention is an immunoglobulin or antigen-binding fragment thereof which binds a naturally occurring mammalian MEC and inhibits binding of said MEC to a naturally occurring mammalian C—C chemokine receptor 3 (CCR3) and/or a naturally occurring mammalian C—C chemokine receptor 10 (CCR10). In another embodiment, the invention is an immunoglobulin or antigen-binding fragment thereof which binds a naturally occurring mammalian CCR3 and inhibits binding of a naturally occurring mammalian MEC thereto. In another embodiment, the invention is an immunoglobulin or antigen-binding fragment thereof which binds a naturally occurring mammalian CCR10 and inhibits binding of a naturally occurring mammalian MEC thereto. Preferably the immunoglobulin is a chimeric, humanized or human immunoglobulin or an antigen-binding fragment of a chimeric, humanized or human immunoglobulin.

Models of Inflammation

In vivo models of inflammation are available which can be used to assess the efficacy of agents identified by the methods described herein as in vivo therapeutics. For example, leukocyte infiltration upon intradermal injection of MEC and antibody or antigen-binding fragment thereof that binds mammalian CCR3 and inhibits binding of MEC to CCR3 into a suitable animal, such as rabbit, mouse, rat, guinea pig or primate (e.g., *Rhesus macaque*) can be monitored (see e.g., Van Damme, J. et al., *J. Exp. Med.*, 176: 59–65 (1992); Zachariae, C. O. C. et al., *J. Exp. Med.* 171: 2177–2182 (1990); Jose, P. J. et al., *J. Exp. Med.* 179: 881–887 (1994)). In one embodiment, skin biopsies are assessed histologically for infiltration of leukocytes (e.g., $CCR3^+$ eosinophils or T cells).

In another embodiment, labeled cells (e.g., stably transfected cells expressing a mammalian CCR10, labeled with $^{111}$In for example) capable of chemotaxis and extravasation are administered to the animal. For example, an agent to be assessed which binds a mammalian CCR10 and inhibits binding of MEC to CCR10 can be administered, either before, simultaneously with or after MEC is administered to the test animal. A decrease in the extent of infiltration in the presence of agent (e.g., an antibody or antigen-binding fragment thereof) as compared with the extent of infiltration in the absence of said agent is indicative of inhibition of binding of MEC to CCR10.

A variety of in vivo models of inflammatory diseases can be used to assess the effects of agents in vivo. For example, agents which inhibit the binding of MEC to CCR3 and/or CCR10 can be evaluated in a sheep model for asthma (see e.g., Weg, V. B. et al., *J. Exp. Med.*, 177: 561 (1993), the teachings of which are incorporated herein by reference), a rat delayed type hypersensitivity model (Rand, M. L. et al., *Am. J. Pathol.*, 148: 855–864 (1996), the teachings of which are incorporated herein by reference), or other suitable models. Additional suitable models include, models of mucosal inflammatory diseases (e.g., respiratory tract (bronchus, lung), urogenital tract, alimentary canal and associated organs and tissues (e.g., pancreas, liver, gall bladder)). For example, the agents identified by the methods described herein, can be studied in the cotton-top tamarin model of inflammatory bowel disease (Podolsky, D. K., et al., *J. Clin. Invest.* 92:372–380 (1993)). The CD45RB$^{Hi}$/SCID model provides a mouse model with similarity to both Crohn's disease and ulcerative colitis (Powrie, F. et al., *Immunity*, 1: 553–562 (1994)). Therapeutic efficacy in this model can be assessed, for example, by using parameters such as inhibition of recruitment of $^{111}$In-labeled cells to the colon and reduction in the number of CD4$^+$ T lymphocytes in the lamina propria of the large intestine after administration (e.g., intravenous (i.v.), intraperitoneally (i.p.) and per oral (p.o.)) of an agent. Knockout mice which develop intestinal lesions similar to those of human inflammatory bowel disease have also been described (Strober, W. and Ehrhardt, R. O., *Cell*, 75: 203–205 (1993)), and NOD mice provide an animal model of insulin-dependent diabetes mellitus. Well established animal models for multiple sclerosis (e.g., experimental autoimmune encephalitis in rodents (e.g., mice, rats)), cancers and infectious diseases can be used. For example, anti-tumor activity can be evaluated in a MCA26 colon carcinoma liver tumor model, in SCID mice injected with human gastric tumor cell line MKN-45, in mice (C3H/HeN) injected with CL-62 melanoma cells, in mice injected with HOPE2 metastatic melanoma cells or other suitable models (see, for example, Pham-Nguyen, K. B., et al., *Int. J. Cancer*, 81:813–819 (1999); Senba, T., et al., *Anticancer Res.*, 18:17–24 (1998), Thibault, C., et al., *Int. J. Cancer*, 67:232–237 (1996), Hariharan, K., et al., *Int. J. Oncol.*, 12:1229–1235 (1998)). Animal models which closely resemble human diseases, such as viral infections (HIV, EBV, hepatitis C virus) and cancers (e.g., lymphoid tumors) in SCID-hu mice can be used (see, for example, Seydel K. B. et al., *Gastroenterology*, 115:1446–1453 (1998), Bristol, G. C. et al., *Methods*, 12:343–347 (1997), Jansen, B. et al., *Int. J Cancer*, 67:821–825 (1996), McCune, J. M., et al., *Curr. Top. Microbiol. Immunol.*, 152:183–193 (1989)).

Methods of Therapy

Modulation of cellular functions (e.g., signaling, chemotaxis, degranulation, exocytosis, secretion, adhesion, extravisation) induced upon binding of ligand (e.g., MEC) to CCR3 and/or CCR10 provides an effective and selective way of modulating the functions (e.g., leukocyte infiltration including recruitment and/or accumulation) of leukocytes. Once lymphocytes are recruited to a site, other leukocyte types, such as monocytes, may be recruited by secondary signals. Thus, agents which modulate the binding of MEC to CCR3 and/or CCR10, including ligands, inhibitors and/or promoters, such as those identified as described herein, can be used to modulate leukocyte function (e.g., leukocyte (e.g., eosinophil, T cell) infiltration including recruitment and/or accumulation).

In one aspect, the present invention provides a method of modulating (inhibiting or promoting) an inflammatory response in a subject in need of such therapy, comprising administering an effective amount of an agent which modulates the binding of MEC to CCR3 and/or CCR10 to a subject in need of such therapy. In one embodiment, an effective amount of an agent which inhibits the binding of MEC to CCR3 and/or CCR10 is administered to a subject to inhibit inflammation (e.g., to reduce inflammation, to prevent inflammation). For example, antibodies and antigen-binding fragments which bind to CCR3 or CCR10 and inhibit the binding of MEC to CCR3 or CCR10, or antibodies or antigen-binding fragments thereof which bind MEC and inhibit binding of the chemokine to CCR3 and/or CCR10 can be used in the method. As a result, one or more inflammatory processes, such as leukocyte emigration, chemotaxis, exocytosis (e.g., of enzymes) or inflammatory mediator release, can be inhibited. For example, leukocytic infiltration into inflammatory sites (e.g., in an inflamed mucosal tissues (e.g., colon, small intestine, salivary gland, mammary gland, lung, bronchus)) can be inhibited according to the present method. According to the method the severity of symptoms associated with an inflammatory condition can be inhibited (reduced) in whole or in part. Where the subject has a relapsing or chronic condition, an effective amount of an agent which inhibits the binding of MEC to CCR3 and/or CCR10 can be administered to treat the condition, and therapy can be continued (maintenance therapy) with the same or different dosing as indicated, to inhibit relapse or renewed onset of symptoms.

Thus, the invention relates to a method of treating a subject having an inflammatory disease, comprising administering to the subject an effective amount of an agent which inhibits the binding of MEC to CCR3 and/or CCR10 and/or which inhibits the function of CCR3 and/or CCR10 upon MEC binding (e.g., MEC-induced signaling or activation). In one embodiment, the subject has an inflammatory bowel disease, such as Crohn's disease or colitis. In another embodiment the subject has mastitis.

In another embodiment the invention is a method of treating a subject having an oral inflammatory condition, comprising administering to the subject an effective amount of an agent which inhibits the binding of MEC to CCR3 and/or CCR10. In additional embodiments, the subject has Sjogren's syndrome or Behcet's syndrome.

In another embodiment the invention is a method of treating a subject having a chronic obstructive lung disease (e.g, chronic bronchitis, asthma, silicosis, chronic obstructive pulmonary disease), comprising administering to the subject an effective amount of an agent which inhibits the binding of MEC to CCR3 and/or CCR10. In another embodiment, the subject has asthma.

The invention also relates to a method of inhibiting CCR3 and/or CCR10-mediated homing of leukocytes (e.g., MEC-induced homing) in a subject, comprising administering an effective amount of an agent which inhibits the binding of MEC to CCR3 and/or CCR10 and/or which inhibits the function of CCR3 and/or CCR10 upon MEC binding (e.g., MEC-induced signaling or activation). For example, the homing of leukocytes (e.g., antibody-secreting cells (e.g., IgA antibody-secreting cells)) to mucosal sites can be inhibited.

In another embodiment, an agent which promotes or augments one or more MEC-induced functions of a mammalian CCR3 and/or CCR10 protein is administered to induce (trigger or enhance) the recruitment of cells to a desired site or to induce an inflammatory response, such as leukocyte emigration, chemotaxis, exocytosis (e.g., of enzymes) or inflammatory mediator release, resulting in the beneficial stimulation of inflammatory processes. For example, T cells and/or particular subsets of lymphocytes can be recruited to combat infections (e.g., viral, bacterial, fungal). For example, antibody-secreting cells (e.g., IgA antibody-secreting cells) can be recruited to a desired location, such as mucosal tissues. Recruitment of antibody-secreting cells, such as IgA antibody-secreting cells, to mucosal sites by, for example, the local administration of MEC, can result in enhanced secretion of antibody (e.g., IgA) across the mucosa. Such enhanced secretion can accompany a concurrent reduction in the quantity of circulating antibody. Thus, recruitment of antibody-secreting cells to mucosal tissues can be efficacious for the treatment of hyper-immunoglobulin syndromes (e.g., hyper IgA syndrome, hyper gammaglobulinemia) and associated nephropathies (e.g., glomerulonephritis).

In another embodiment, the invention relates to a method of promoting MEC-induced homing of cells (e.g., leukocytes, such as antibody-secreting cells (e.g., IgA antibody-secreting cells)) which express CCR3 and/or CCR10 in a subject, comprising administering to the subject an effective amount of an agent which promotes or augments binding of MEC to CCR3 and/or CCR10, and/or augments one or more MEC-induced functions of a mammalian CCR3 and/or CCR10 protein.

Agents which can inhibit the binding of MEC to CCR3 and/or CCR10, including antibodies, such as those identified as described herein, can be used to modulate leukocyte function (e.g., leukocyte infiltration including recruitment and/or accumulation). In one aspect, the present invention provides a method of modulating (inhibiting or promoting) an inflammatory response in a subject in need of such therapy, comprising administering an effective amount of an antibody or antigen-binding fragment thereof which inhibits binding of MEC to CCR3 and/or CCR10 to an individual in need of such therapy. In one embodiment, an effective amount of an antibody or antigen-binding fragment thereof which inhibits binding of mammalian MEC to mammalian CCR3 and/or mammalian CCR10 is administered to a subject to inhibit (reduce or prevent) inflammation. As a result, one or more inflammatory processes, such as leukocyte emigration, chemotaxis, exocytosis (e.g., of enzymes) or inflammatory mediator release, is inhibited. For example, leukocytic infiltration of inflammatory sites (e.g., in an inflamed mucosal tissue (e.g., colon, small intestine, bronchus, lung, mammary gland, salivary gland)) can be inhibited according to the present method. In another embodiment, an effective amount of an antibody or antigen-binding fragment thereof which inhibits binding of mammalian MEC to mammalian CCR3 and/or CCR10 protein (e.g., human CCR3 and/or human CCR10) is administered to a subject to inhibit MEC-induced homing of leukocytes. In another embodiment, a humanized or human antibody having the same or similar binding specificity as murine monoclonal antibody 7B11 can be administered to a subject in need thereof, thereby beneficially inhibiting binding of MEC to CCR3 and/or CCR10. In one example, a humanized antibody which comprises at least one complementarity determining region (CDR) of the heavy chain (CDR1, CDR2 and/or CDR3) and at least one CDR of the light chain (CDR1, CDR2 and/or CDR3) of murine monoclonal antibody 7B11 and a human framework region, and which has the same or similar binding specificity as murine monoclonal antibody 7B11 can be administered in accordance with the invention.

In one embodiment, the agent or agents to be administered in accordance with the invention do not include viruses or viral proteins (e.g., viral envelope proteins). In another embodiment, the agent or agents to be administered in accordance with the invention do not include chemokines or mutants or analogues thereof. In another embodiment, the agent or agents to be administered in accordance with the invention do not include immunoglobulins (antibodies) or antigen-binding fragments thereof (e.g., antibodies or antigen-binding fragments which have binding specificity for human CCR3, human CCR10 and/or human MEC).

The term "subject" is defined herein to includes humans and animals such as mammals, including, but not limited to, primates, cows, sheep, goats, horses, dogs, cats, rabbits, guinea pigs, rats, mice or other bovine, ovine, equine, canine, feline, rodent or murine species.

Diseases and conditions associated with inflammation, infection, and cancer can be treated using the method. In a preferred embodiment, the disease or condition is one in which the actions of lymphocytes, such as eosinophils or activated or stimulated T lymphocytes, are to be inhibited or promoted for therapeutic or prophylactic purposes.

Diseases or conditions, including chronic diseases, of humans or other species which can be treated with agents which can inhibit the binding of MEC to CCR3 and/or CCR10 or MEC-induced functions thereof, include, but are not limited to:

inflammatory or allergic diseases and conditions, including systemic anaphylaxis or hypersensitivity responses, drug allergies (e.g., to penicillin, cephalosporins), insect sting allergies; inflammatory bowel diseases, such as Crohn's disease, ulcerative colitis, ileitis, enteritis, nontropical sprue and celiac disease; vaginitis; psoriasis and inflammatory dermnatoses such as dermatitis, eczema, atopic dermatitis, allergic contact dermatitis, dermatitis herpetiformis, linear IgA disease, urticaria; vasculitis (e.g., necrotizing, cutaneous, and hypersensitivity vasculitis); spondyloarthropathies; scleroderma; respiratory allergic diseases such as asthma, allergic rhinitis, hypersensitivity lung diseases, hypersensitivity pneumonitis, interstitial lung diseases (ILD) (e.g., idiopathic pulmonary fibrosis, or ILD associated with rheumatoid arthritis, or other autoimmune conditions);

autoimmune diseases, such as arthritis (e.g., rheumatoid arthritis, psoriatic arthritis), multiple sclerosis, systemic lupus erythematosus, myasthenia gravis, diabetes, including diabetes mellitus and juvenile onset diabetes, glomerulonephritis and other nephritides, (e.g., antibody-mediated nephropathy (e.g., IgA nephropathy (Berger's Disease))), autoimmune thyroiditis, Behcet's syndrome;

graft rejection (e.g., in transplantation), including allograft rejection or graftversus-host disease;

viral infection, e.g., infection by simian immunodeficiency virus (SIV) or human immunodeficiency virus (HIV);

other diseases or conditions in which undesirable inflammatory responses are to be inhibited can be treated, including, but not limited to, atherosclerosis (e.g., transplant accelerated atherosclerosis), restenosis, cytokine-induced toxicity, myositis (including polymyositis, dermatomyositis).

Diseases or conditions of humans or other species which can be treated with agents that can promote or augment one or more MEC-induced functions of a mammalian CCR3 and/or CCR10, include, but are not limited to:

cancers, for example, solid tumors and/or those with leukocytic infiltration of the skin or organs such as cutaneous T cell lymphoma (e.g., mycosis fungoides);

diseases in which angiogenesis or neovascularization plays a role, including neoplastic disease, retinopathy (e.g., diabetic retinopathy), and macular degeneration;

infectious diseases, such as bacterial infections and tuberculoid leprosy, and especially viral infections;

immunosuppression, such as that in individuals with immunodeficiency syndromes such as AIDS, IgA deficiency and selective IgA deficiency (including diseases associated with IgA deficiency and selective IgA deficiency, e.g., neutropenias, bronchiectasis), individuals undergoing radiation therapy, chemotherapy, or other therapy which causes immunosuppression; immunosuppression due to congenital deficiency in receptor function or other causes.

Modes of Administration

According to the method, one or more agents can be administered to the subject by an appropriate route, either alone or in combination with another drug. An effective amount of an agent (e.g., an antibody which binds CCR3 and inhibits binding of MEC to CCR3, an antibody which binds CCR10 and inhibits binding of MEC to CCR10) is administered. An effective amount is an amount sufficient to achieve the desired therapeutic or prophylactic effect, under the conditions of administration, such as an amount sufficient to inhibit binding of MEC to CCR3 and/or CCR10, and thereby, inhibit an inflammatory response. The agents can be administered in a single dose or multiple doses. The dosage can be determined by methods known in the art and is dependent, for example, upon the agent chosen, the subject's age, sensitivity and tolerance to drugs, and overall well-being. Typically, an effective amount can range from about 0.01 mg per day to about 100 mg per day for an adult. Preferably, the dosage ranges from about 1 mg per day to about 100 mg per day or from about 1 mg per day to about 10 mg per day. Antibodies and antigen-binding fragments thereof, such as human, humanized and chimeric antibodies and antigen-binding fragments can often be administered with less frequency than other types of therapeutics. For example, an effective amount of an antibody can range from about 0.01 mg/kg to about 5 or 10 mg/kg administered daily, weekly, biweekly or monthly.

A variety of routes of administration are possible including, for example, oral, dietary, topical, transdermal, rectal, parenteral (e.g., intravenous, intraarterial, intramuscular, subcutaneous, intradermal injection), and inhalation (e.g., intrabronchial, intranasal or oral inhalation, intranasal drops) routes of administration, depending on the agent and disease or condition to be treated. Administration can be local or systemic as indicated. The preferred mode of administration can vary depending upon the agent chosen, and the condition (e.g., disease) being treated, however, oral or parenteral administration is generally preferred.

The agent can be administered as a neutral compound or as a salt. Salts of compounds containing an amine or other basic group can be obtained, for example, by reacting with a suitable organic or inorganic acid, such as hydrogen chloride, hydrogen bromide, acetic acid, perchloric acid and the like. Compounds with a quaternary ammonium group also contain a counteranion such as chloride, bromide, iodide, acetate, perchlorate and the like. Salts of compounds containing a carboxylic acid or other acidic functional group can be prepared by reacting with a suitable base, for example, a hydroxide base. Salts of acidic functional groups contain a countercation such as sodium, potassium and the like.

The agent can be administered to the individual as part of a pharmaceutical composition for modulation (e.g., inhibition) of MEC-induced CCR3 and/or CCR10 function comprising an inhibitor or promoter of MEC-induced CCR3 and/or CCR10 function and a pharmaceutically or physiologically acceptable carrier. Formulation will vary according to the route of administration selected (e.g., solution, emulsion, capsule). Suitable pharmaceutical and physiological carriers can contain inert ingredients which do not interact with the agent (e.g, inhibitor of MEC binding to CCR3 and/or CCR10). Standard pharmaceutical formulation techniques can be employed, such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% benzyl alcohol), phosphate-buffered saline, Hank's solution, Ringer's-lactate and the like. Methods for encapsulating compositions (such as in a coating of hard gelatin or cyclodextran) are known in the art (Baker, et al., "Controlled Release of Biological Active Agents", John Wiley and Sons, 1986). For inhalation, the agent can be solubilized and loaded into a suitable dispenser for administration (e.g., an atomizer, nebulizer or pressurized aerosol dispenser).

Furthermore, where the agent is a protein or peptide, the agent can be administered via in vivo expression of the recombinant protein. In vivo expression can be accomplished via somatic cell expression according to suitable methods (see, e.g. U.S. Pat. No. 5,399,346). In this embodiment, a nucleic acid encoding the protein can be incorporated into a retroviral, adenoviral or other suitable vector (preferably, a replication deficient infectious vector) for delivery, or can be introduced into a transfected or transformed host cell capable of expressing the protein for delivery. In the latter embodiment, the cells can be implanted (alone or in a barrier device), injected or otherwise introduced in an amount effective to express the protein in a therapeutically effective amount.

The present invention will now be illustrated by the following Exemplification, which is not intended to be limiting in any way.

EXEMPLIFICATION

Example 1

Materials and Methods

Cloning and Sequencing of MEC.

TBLASTN (Altschul S. F. et al., *J. Mol. Biol.*, 215:403–410 (1990)) searches of the GenBank dbEST database with the sequences of known CC chemokines identified the expressed sequence tag (EST) for human MEC. IMAGE consortium clone #136910, prepared using cDNAs from human full term placenta, was obtained from the American Type Culture Collection (Manassas, Va.; Accession Number 374823). The clone contained an about 1 kb *EcoRI-NotI* insert in the pT7T3D-Pac vector. The nucleotide sequence was confirmed by automated sequencing. Protein similarity and dendrogram analysis was done using ClustalW (Thompson J. D., et al., *Nucleic Acids Res.*, 22:4673–4680 (1994)). BLASTN searches of the high throughput genome database using the MEC cDNA sequence revealed two BAC clones from human chromosome 5, CTD-2282F8 (GenBank Accession No. AC010465) and CTD-2202K16 (GenBank Accession No. AC025457), that encode the human MEC gene. The entire teachings of GenBank Accession Numbers AC010465 and AC025457 are incorporated herein by reference.

Synthesis of MEC.

The signal sequence of MEC was predicted using SignalP (Nielsen H. et al. *Protein Engineering* 10:1–6 (1997); available online at http://www.cbs.dtu.dk/signal/cbssignalp.html). The predicted 105 amino acid mature protein (amino acids 23–127 of the coding sequence) was synthesized by FMOC chemistry (automated 433 peptide synthesizer, PE Biosystems). A biotin moiety (aminocaproic acid-biotin) was added to Lysine 124. The purity (>95%) and molecular integrity of the purified folded chemokine was determined by analytical reversed phase high pressure liquid chromatography (RP-HPLC) using a C18 column, as well as by mass spectrometry. Synthesized MEC had an experimentally determined molecular weight of 12408.7 Daltons (versus a theoretical weight of 12409.5 Daltons). CTACK, TECK, and other chemokines were synthesized and/or purchased from Peprotech (Rocky Hill, N.J.).

Blood Cells and Cell Lines.

A panel of 15 known chemokine receptor and 12 orphan G protein-coupled receptor stable transfectants were generated in the murine pre-B lymphoma cell line L1/2 as described (Ponath, P. D. et al, *J. Exp. Med.*, 183:2437–2448 (1996); Honda, S. et al., *J. Immunol.* 152:4026 (1994)). Some of the transfectants expressed chemokine receptors and orphan receptors that contained an amino terminal influenza hemagglutinin epitope tag (SEQ ID NO:24). The CCR3 transfectants used in the study expressed human CCR3 that did not contain an HA epitope tag. CCR10 transfectants used in the study expressed human CCR10 that contained an amino terminal HA epitope tag or expressed human CCR10 that did not contain an HA epitope tag. Constructs encoding human CCR3 or CCR10 were prepared using the vector pCDNA3 (Invitrogen, Carlsbad, Calif.). The CCR10 (GPR-2) full length sequence was kindly provided by Dr. Craig Gerard (Jarmin, D. I. et al., *J. Immunol.* 164:3460 (2000)). L1/2 transfectants were stimulated overnight with 10 mM butyric acid prior to performing chemotaxis assays. Peripheral blood mononuclear leukocytes and eosinophils were isolated from whole blood as described previously (Campbell, J. J. et al., *J. Cell Biol.* 141:1053 (1998) and Ponath, P. D. et al., *J. Exp. Med.* 183:2437 (1996)).

Chemotaxis of L1/2 Transfectants and Blood Lymphocytes.

Chemotaxis assays were performed using 24-well TRANSWELL plates (tissue culture plates fitted with TRANSWELL permeable tissue culture support devices (Corning Costar, Cambridge, Mass.); 3 $\mu$m pores for L1/2 cells and eosinophils and 5 $\mu$m pores for lymphocytes) as described (Campbell, J. J. et al., *J. Cell Biol* 141:1053 (1998); Ponath, P. D. et al., *J. Exp. Med.* 183:2437 (1996)). L1/2 transfectants were incubated from 5 hrs to overnight and lymphocytes and eosinophils were incubated for 1.5 hr. Migrated cells were quantified by flow cytometry (number of migrated cells corresponds to events acquired in a fixed time of 30 seconds). Migrated cells were stained with CD4-APC or CD8-APC, CD45RA-Cy, CLA-FITC, and $\alpha_4\beta_7$-PE to analyze T cells, IgD-FITC, CD19-PE, and CD45RA-Cy for B cell analysis, or CD49d-PE for eosinophil analysis (all conjugated antibodies were purchased from Pharmingen, San Diego, Calif.). Four color flow cytometry was done on a FACSCalibur™ flow cytometer (Becton-Dickinson, San Jose, Calif.) using CellQuest™ version 3.1 analysis software (Becton-Dickinson). Optimal chemotactic doses were as follows: MEC, 300 nM; CTACK, 300 nM; SDF-1$\alpha$, 100 nM; TARC, 100 nM; Eotaxin, 30 nM (all chemokines except MEC and CTACK were purchased from Peprotech, Rocky Hill, N.J.). For gradient disruption experiments, chemotaxis was carried out identically, except that three times the optimal chemotactic dose of chemokine was added to the cells in the top well, and for antibody blockade experiments, 50 ug/mL of blocking mAb (mAb 7B11, mouse $IgG_{2a}$; Millennium Pharmaceuticals, Inc., Cambridge, Mass.) or control mAb (isotype control or eosinophil-binding anti-L-selectin mAb) was added to the top well. mAb 7B11 can be produced by murine hybridoma 7B11, which was deposited on Sep. 25, 1996, on behalf of LeukoSite, Inc., 215 First Street, Cambridge, Mass. 02142, U.S.A. (now Millennium Pharmaceuticals, Inc., 75 Sidney Street, Cambridge, Mass. 02139, U.S.A.) at the American Type Culture Collection, 10801 University Boulevard, Manassas, Va. 20110, U.S.A., under Accession No. HB-12195 (WO 98/14480).

Laser Capture Microdissection.

8 $\mu$m sections from normal human salivary gland and colon (obtained from patients undergoing elective surgery at Stanford University Medical Center) embedded in OCT were cut and immediately fixed in 70% ethanol/diethylpyrocarbonate (DEPC)-treated water for 30 s. Sections were counterstained with Toludine blue (Sigma, St. Louis, Mo.)/DEPC-treated water for 30 s, dehydrated in increasing concentrations of ethanol/DEPC-treated water, and cleared in xylene. Sections were allowed to air dry in a slide case containing dessicant to prevent rehydration. Laser capture microdissection was performed using a PixCell II® laser capture microdissection system (Arcturus Engineering, Mountain View, Calif.). Epithelial and non-epithelial cells were captured from each tissue, lysed in guanidinium buffer, and placed on ice for later RT-PCR and Southern analysis. Total RNA was isolated and subjected to a semi-quantitative RT-PCR analysis as described (Campbell, J. J. et al., *J. Immunol.* 163:2353 (1999)). PCR was performed using synthetic oligonucleotide (DNA) primers for human MEC:

5'-CCATCGTGGCCTTGGCTGTCTGTG-3' (SEQ ID NO: 21) and

5'-GCCGTATGTTTCGTGTTTCCCCTG-3' (SEQ ID NO: 22) with the internal probe

5'-GGGAAGTATGGCTTCTGAGGC-3' (SEQ ID NO: 23).

Northern Analysis for MEC mRNA.

Human epithelial cells derived from bronchus-associated epithelium or mammary gland epithelium were obtained from Clonetics (Walkerville, Md.) and cultured in complete medium according to the manufacturer's instructions. EA.hy926, a hybrid human umbilical vein endothelial cell line was a gift from Dr. Edgell at the University of North Carolina (Edgell, C. J. et al., *Proc. Natl Acad. Sci. U.S.A.*, 80:3734–3737 (1983)). PolyA+ RNA from these cell lines was isolated using a FastTrack™ mRNA isolation kit (Invitrogen, Carlsbad, Calif.). PolyA+ RNA from various human tissues was purchased from Clontech (Palo Alto, Calif.) or Clemente Associates (Madison, Wis.). RNA was separated on a 1.5% formaldehyde-agarose gel and quantified by northern blot analysis.

Results and Discussion

MEC is a Novel Chemokine Ligand for CCR10 and CCR3

A BLAST search of the GenBank human EST database with the coding region of CTACK identified an EST encoding a novel chemokine, here termed MEC (for mucosae-associated epithelial chemokine). The MEC coding sequence displays 49% and 45% nucleotide identity with the coding sequences of CTACK and TECK, respectively (FIG. 1A). Interestingly, unlike CTACK on chromosome 9, and TECK on chromosome 19, MEC is encoded on human chromosome 5 by at least four exons separated by large introns (FIG. 1B). At the protein level, MEC displays ~40% amino acid identity in the common homology region with CTACK, and some amino acid identity with TECK, but MEC has a longer C-terminus than CTACK and contains 6 cysteines (FIG. 1C).

Figure 2A:
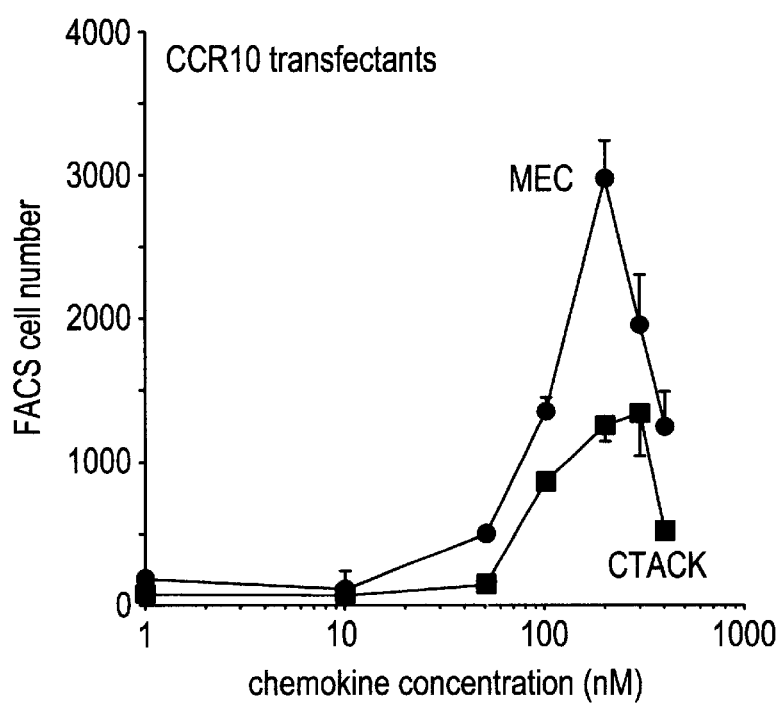
FIG. 2A is a graph showing dose-dependent chemotaxis of L1/2 cells that expressed recombinant human C—C chemokine receptor 10 (CCR10 transfectants) toward MEC (-●-) or CTACK (-■-; a positive control) in in vitro chemotaxis assays. Medium that contained a predetermined concentration of MEC or CTACK was added to the bottom chamber of TRANSWELL plates (tissue culture plates fitted with TRANSWELL permeable tissue culture support devices (Costar Corporation, Cambridge, Mass.)), and CCR10 transfectants in medium were added to the top chamber. The plates were cultured for about 5 hours to overnight and the number of cells that migrated into the bottom chamber was determined by flow cytometry. "FACs cell number" is the number of events (cells in the lower chamber) counted by flow cytometry during a 30 second time period.
Figure 2B:
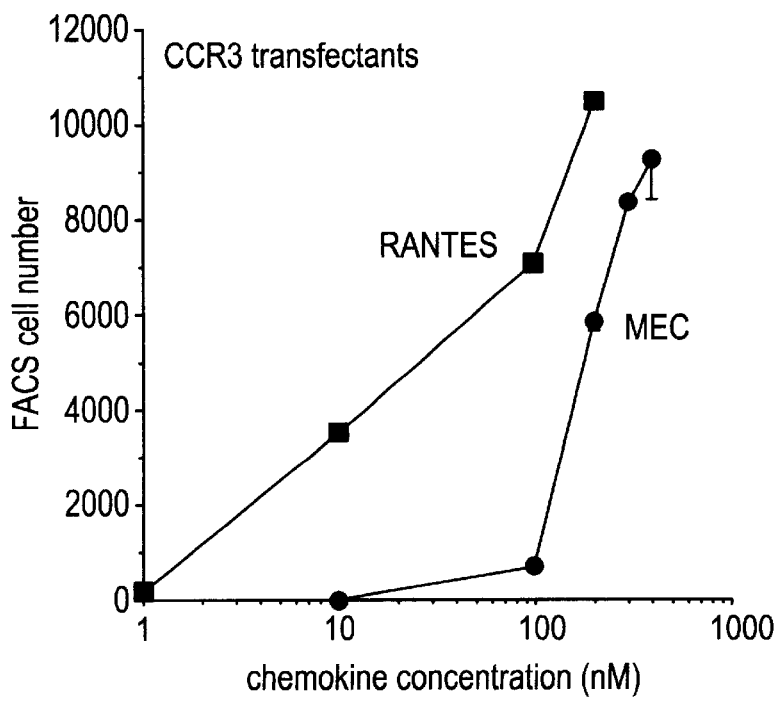
FIG. 2B is a graph showing dose-dependent chemotaxis of L1/2 cells that expressed recombinant human C—C chemokine receptor 3 (CCR3 transfectants) toward MEC (-●-) or RANTES (-■-; a positive control) in in vitro chemotaxis assays. Medium that contained a predetermined concentration of MEC or RANTES was added to the bottom chamber of TRANSWELL plates (tissue culture plates fitted with TRANSWELL permeable tissue culture support devices), and CCR3 transfectants in medium were added to the top chamber. The plates were cultured for about 5 hours to overnight and the number of cells that migrated into the bottom chamber was determined by flow cytometry. "FACs cell number" is the number of events (cells in the lower chamber) counted by flow cytometry during a 30 second time period.

Synthetic MEC was screened in in vitro chemotaxis assays for activity on L1/2 lymphoid cell lines transfected with known or orphan chemokine receptors. Transfectants expressing CCR10 (GPR-2) or CCR3 migrated efficiently to MEC with an optimal concentration of ~300 nM (FIG. 2A), whereas transfectants expressing other chemokine receptors (CCR2, CCR4, CCR5, CCR6, CCR7, CCR8, CCR9, CXCR3, CXCR4, CXCR5) or orphan G protein-coupled receptors (RDC-1, APJ, FEG-1/LyGPR, STRL33/BONZO, GPR-15/BOB, FLPR-2, TDAG8, CRTH2, ChemR23, GPR1, GusB, AF015524/CRAM) did not migrate toward MEC, even though the transfected cells did migrate toward known chemokine ligands for their receptors.

Figure 2C:
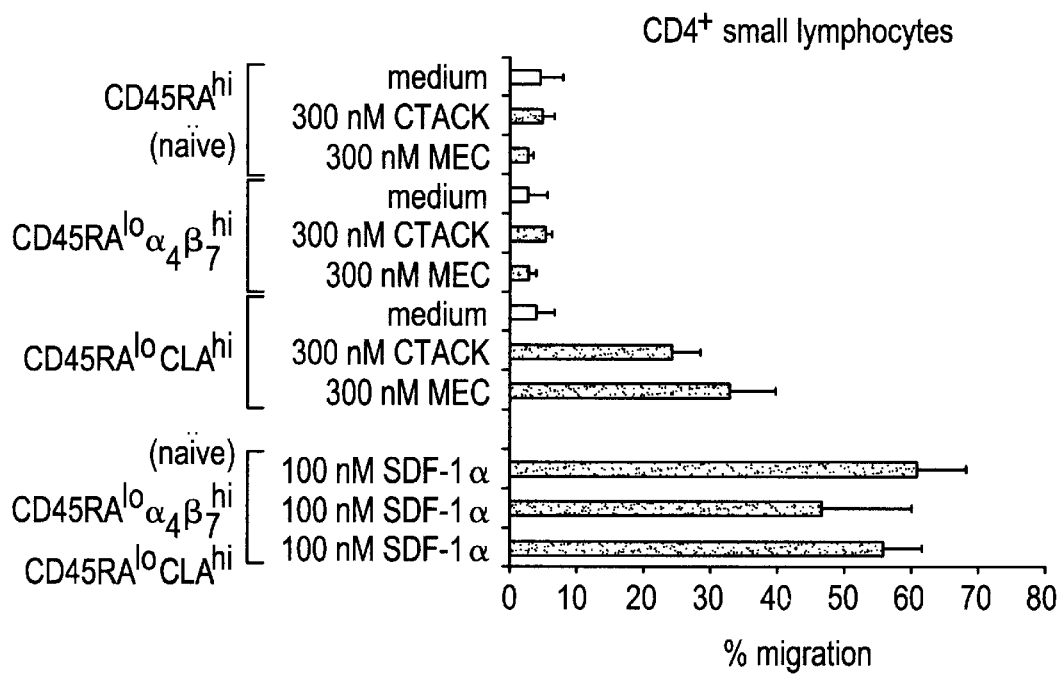
FIG. 2C is a histogram illustrating the phenotypes of human CD4+ lymphocytes that migrated toward MEC, CTACK or SDF-1α in in vitro chemotaxis assays. Medium that contained predetermined concentrations of MEC (300 nM), CTACK (300 nM) or SDF-1α (100 nM) was added to the bottom chamber of TRANSWELL plates (tissue culture plates fitted with TRANSWELL permeable tissue culture support devices), and peripheral blood mononuclear leukocytes in medium were added to the top chamber. The plates were cultured for about 1.5 hours and the number of cells that migrated into the bottom chamber was determined by flow cytometry. The phenotype of cells that migrated to the bottom chamber was determined by staining the cells with labeled antibodies followed by flow cytometry. The histogram presents the percentage of cells of the indicated phenotype in the starting population that migrated toward chemokine. Both MEC and CTACK were chemotactic for memory (CD45RA$^{lo}$) CD4+ T lymphocytes that expressed CLA.
Figure 2D:
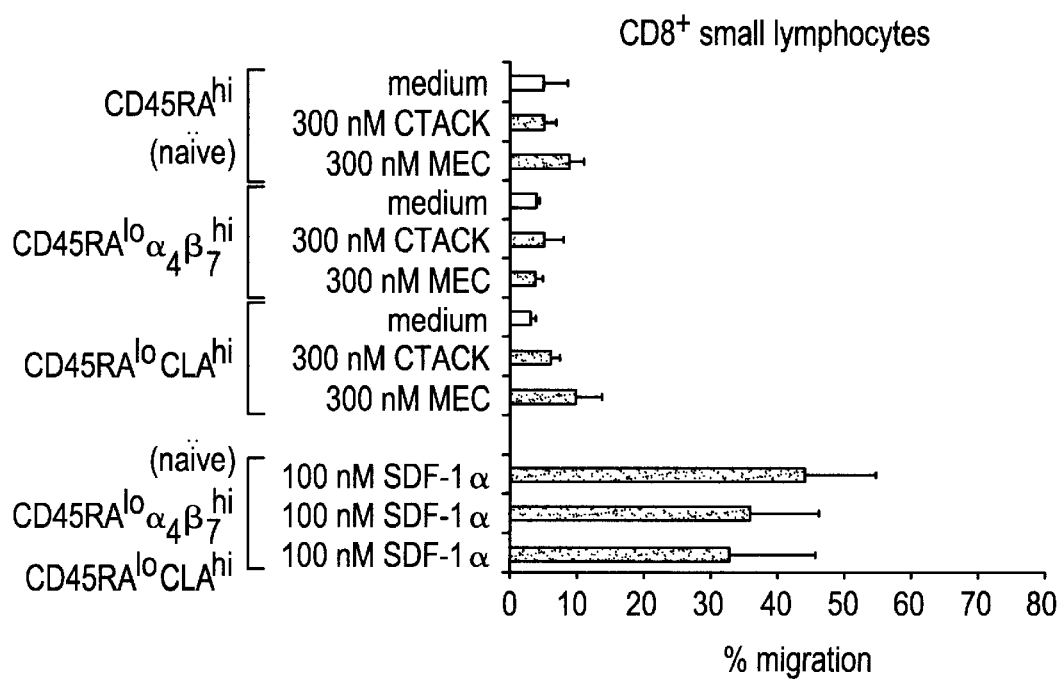
FIG. 2D is a histogram illustrating the phenotypes of human CD8+ lymphocytes that migrated toward MEC, CTACK or SDF-1α in in vitro chemotaxis assays. Medium that contained predetermined concentrations of MEC (300 nM), CTACK (300 nM) or SDF-1α (100 nM) was added to the bottom chamber of TRANSWELL plates (tissue culture plates fitted with TRANSWELL permeable tissue culture support devices), and peripheral blood mononuclear leukocytes in medium were added to the top chamber. The plates were cultured for about 1.5 hours and the number of cells that migrated into the bottom chamber was determined by flow cytometry. The phenotype of cells that migrated to the bottom chamber was determined by staining the cells with labeled antibodies followed by flow cytometry. The histogram presents the percentage of cells of the indicated phenotype in the starting population that migrated toward chemokine.
Figure 2E:
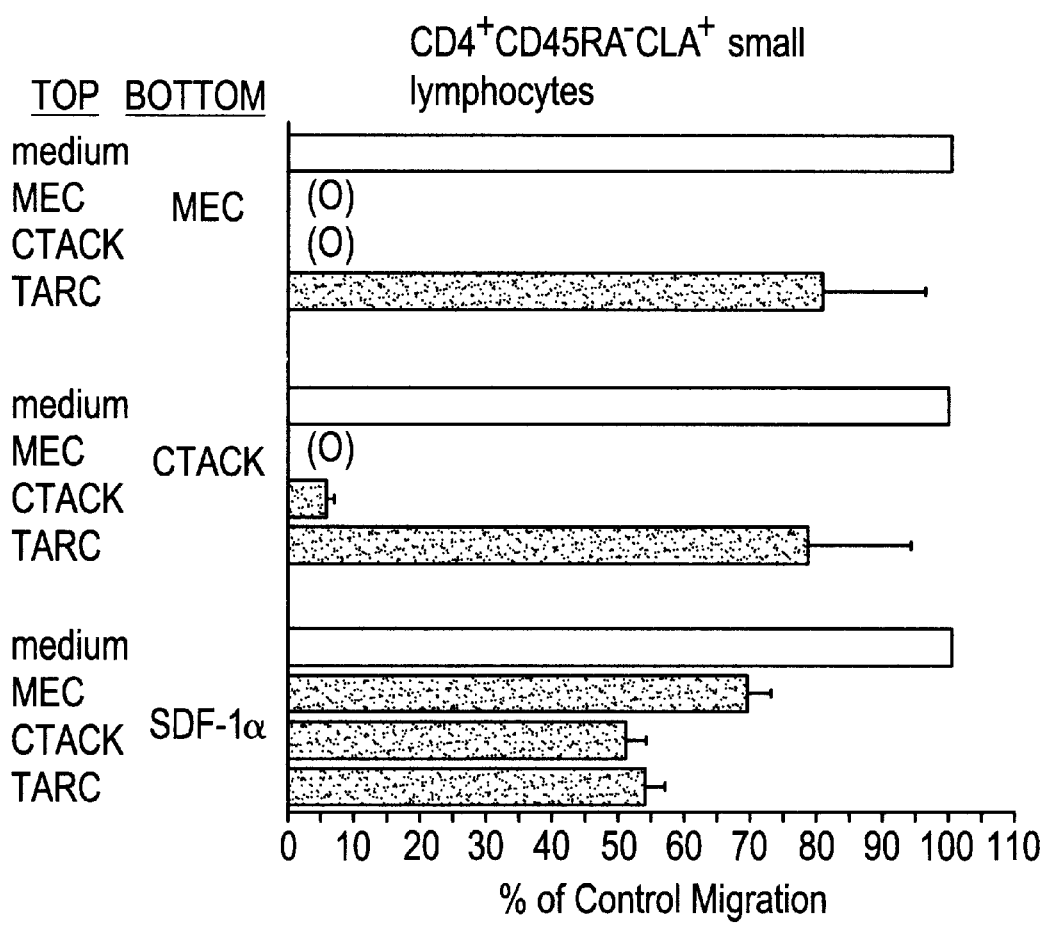
FIG. 2E is a histogram showing that MEC-induced or CTACK-induced chemotaxis of CD4+CD45RA−CLA+ small lymphocytes was inhibited by competing gradients of CTACK or MEC, respectively, in in vitro chemotaxis assays. Medium containing MEC, CTACK or SDF-1α (used at optimal concentrations: MEC, 300 nM; CTACK, 300 nM; SDF-1α, 100 nM) was added to the bottom chamber of TRANSWELL plates (tissue culture plates fitted with TRANSWELL permeable tissue culture support devices), and peripheral blood mononuclear leukocytes in medium or in medium that contained three times the optimal concentration of a competing chemokine (MEC, CTACK, TARC) were added to the top chamber. The plates were cultured for about 1.5 hours and the number and phenotype of cells that migrated into the bottom chamber was determined by flow cytometry. 100% migration was defined as the number of CD4+CD45RA−CLA+ small lymphocytes that migrated to the bottom chamber in wells that did not contain a competing chemokine.

CTACK attracts circulating skin-homing memory CD4+ T cells which express the cutaneous lymphocyte antigen (CLA). To determine if MEC might also be able to recruit memory T cells, human blood T cells were migrated to MEC, CTACK, and SDF-1α, and the phenotype of the starting population and of the chemokine-recruited cells was analyzed by flow cytometry. As shown in FIGS. 2C and 2D, the phenotypes of T cells that migrated in response to MEC or CTACK were indistinguishable. Although MEC and CTACK exhibited similar potencies, MEC was more efficacious at the optimal chemotactic dose (FIGS. 2A–2D). MEC was not detectably chemotactic for naive (IgD$^+$) or memory (IgD$^-$) blood B cells. Migration of T cells to MEC was inhibited by a competing gradient of CTACK (and vice versa) but not by a gradient of TARC (a ligand for CCR4). Similarly, migration of T cells to CTACK was inhibited by a competing gradient of MEC but not by TARC. The results of the competing gradient studies indicated that MEC and CTACK bind and signal through a common receptor on circulating memory CD4 lymphocytes (FIG. 2E).

Figure 2F:
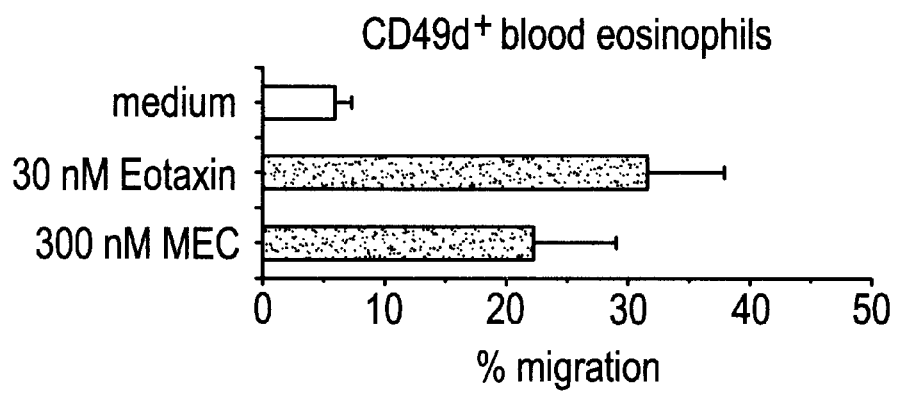
FIG. 2F is a histogram showing that CD49d+ eosinophils migrated in response to MEC or Eotaxin in in vitro chemotaxis assays. Medium containing MEC or Eotaxin (used at optimal concentrations) was added to the bottom chamber of TRANSWELL plates (tissue culture plates fitted with TRANSWELL permeable tissue culture support devices), and peripheral blood granulocytes in medium were added to the top chamber. The plates were cultured for about 1.5 hours and the number and phenotype of cells that migrated into the bottom chamber was determined by flow cytometry. % migration is the percentage of CD49d+ cells in the starting population that migrated to the bottom chamber.
Figure 2G:
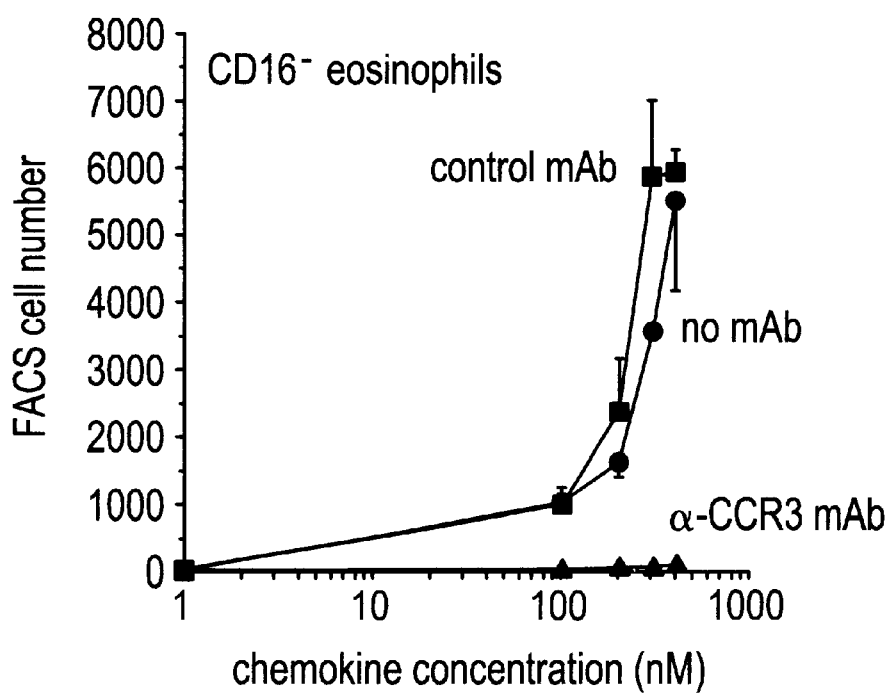
FIG. 2G is a graph showing dose-dependent chemotaxis of purified CD16− eosinophils in response to MEC (-●-) in an in vitro trans-endothelial cell (ECV304) chemotaxis assays. MEC-induced chemotaxis was inhibited by an antibody that binds CCR3 (-▲-) and inhibits binding of MEC thereto, but not by a control antibody (-■-). Peripheral blood CD16− eosinophils were prepared by negative selection of peripheral blood granulocytes using anti-CD16 antibody on magnetic beads. Media containing predetermined concentrations of MEC were added to the bottom chamber of TRANSWELL plates (tissue culture plates fitted with TRANSWELL permeable tissue culture support devices), and CD16− eosinophils in medium, CD16− eosinophils in medium that contained a blocking antibody which binds CCR3 (50 μg/mL) (clone 7B11, Millennium Pharmaceuticals, Inc., Cambridge, Mass.) or CD16− eosinophils in medium that contained an isotype control antibody (50 μg/mL) were added to the top chamber. The plates were cultured for about 1.5 hours and the number of cells that migrated into the bottom chamber was determined by flow cytometry.

Consistent with its ability to attract CCR3 transfectants, MEC also attracted blood eosinophils (FIGS. 2F and 2G). The optimal chemotactic concentration of MEC for both CCR3 transfectants (FIG. 2B) and eosinophils (FIG. 2G) was in the range of 300–400 nM, and was as efficacious as eotaxin or PTEC (another ligand for CCR3). Migration of eosinophils to MEC was completely inhibited by a blocking mAb to CCR3 (FIG. 2G), indicating that MEC binds and signals through CCR3 on eosinophils and not CCR10. This activity distinguishes MEC from CTACK, as CTACK fails to attract either eosinophils or CCR3 transfectants (Morales, J. et al., *Proc. Natl. Acad. Sci. U.S.A.* 96:14470 (1999)).

Mucosal Epithelial Cell Expression of MEC

Figure 3A:
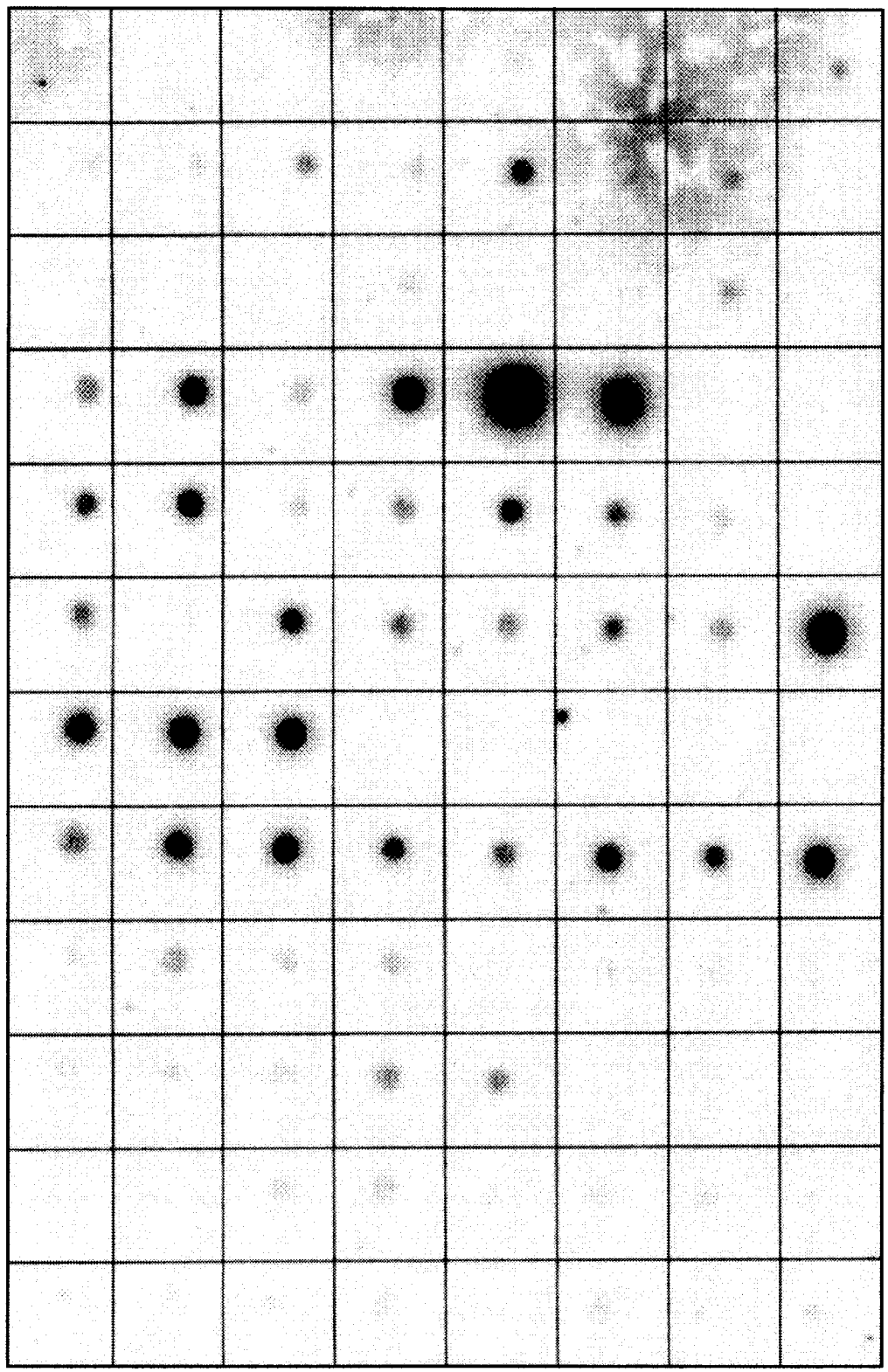
Figure 3C:
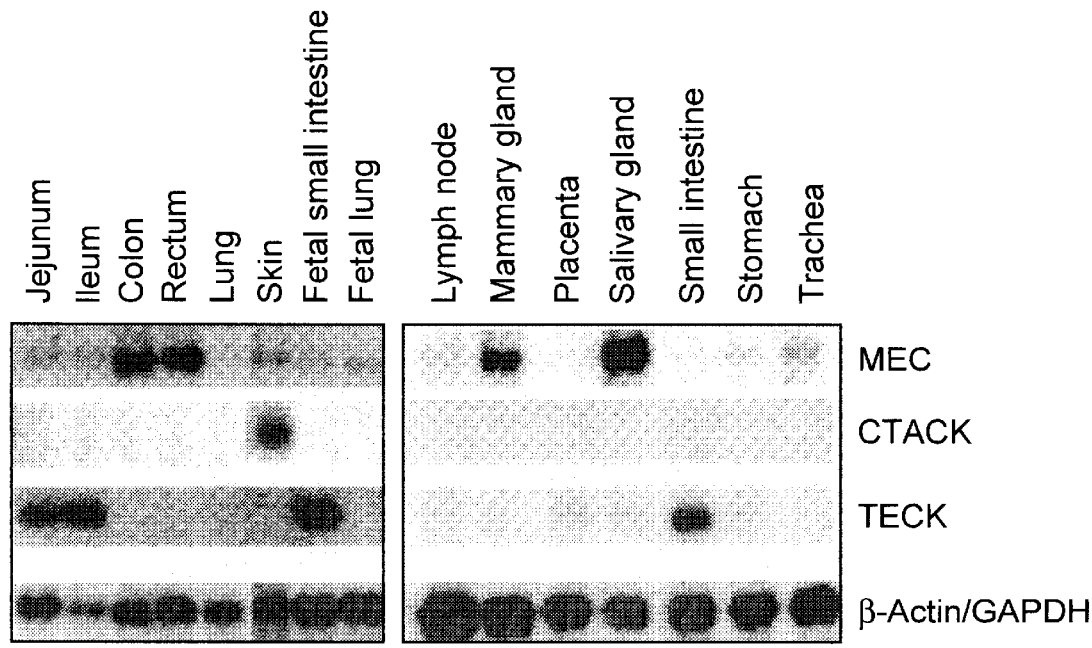
FIG. 3C is a photograph of an autoradiogram of a northern blot containing polyA+ RNA that was isolated from several human tissues and probed to detect mRNA encoding MEC, CTACK, TECK or β-actin and GAPDH. Northern analysis of mRNA from various human tissues confirms the high level of MEC message in salivary gland, colon, mammary gland, and trachea. In contrast, high expression of CTACK was only observed in skin, and high expression of TECK was restricted to the small intestine.

Dot blot analysis of mRNA from diverse human tissues revealed a unique pattern of expression of MEC (FIG. 3A). Further northern blot analysis revealed that MEC message was most abundant in salivary gland, but was also expressed in other tissues associated with mucosal epithelial surfaces, including trachea, mammary gland, colon and rectum (FIG. 3C). Interestingly, MEC message was rare or absent in skin (compare expression of CTACK and MEC in FIG. 3C), and was less abundant in small intestine than in the colon or rectum (compare TECK and MEC expression in FIG. 3C). However, the dot blot results suggested that there can be variable low expression of MEC in different segments of the small intestine and the stomach, pancreas, thyroid gland, and prostate (FIG. 3A). In the northern blots, the MEC cDNA probe detected five transcripts of different sizes (0.8, 1, 3, 3.5, and 6 kb), with the 3 kb transcript being the most abundant. The abundance of the other transcripts correlated with that of the 3 kb transcript, and there were no obvious tissue-specific transcripts in any tissues examined. The transcripts may represent splice variants of MEC and/or variations in polyadenylation sites.

Figure 3D:
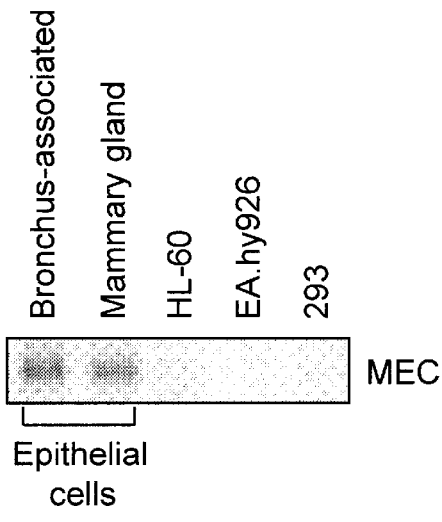
FIG. 3D is a photograph of an autoradiogram of a northern blot containing RNA samples isolated from bronchus-associated epithelial cells, mammary gland epithelial cells, myeloid (HL-60; ATCC Accession No. CCL-240), fibroblastic (293; ATCC Accession No. CRL-1573) or endothelial (EA.hy926) cell lines that was probed to detect expression of MEC using $^{32}$P-labeled full-length MEC cDNA probe (nucleotides 1–739 of SEQ ID NO:1). MEC was found to be expressed in bronchial and mammary gland epithelial cells, but not myeloid (HL-60), fibroblastic (293), or endothelial (EA.hy926) cell lines.
Figure 3E:
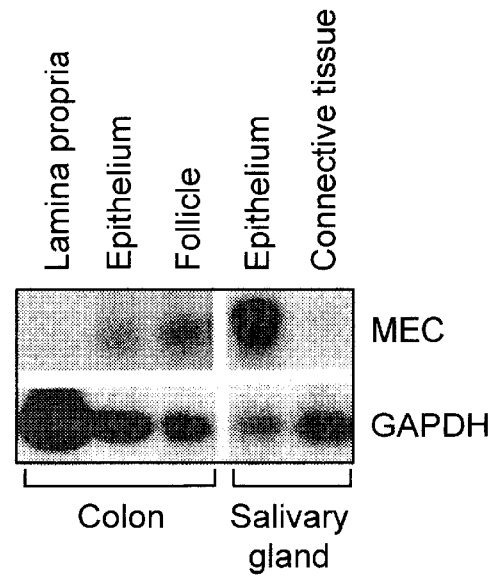
FIG. 3E is a photograph of an autoradiogram of a Southern blot showing the level of MEC mRNA detected in epithelial cells, follicular cells or lamina propria cells isolated from colon and in epithelial cells or connective tissue cells isolated from salivary gland. Epithelial cells and non-epithelial cells were isolated from colon or salivary gland using laser capture microdissection, lysed in guanidinium buffer and analyzed for MEC expression by RT-PCR followed by Southern blotting. MEC mRNA was enriched in laser capture microdissected epithelial cells and colon follicles, as compared to lamina propria or connective tissue from salivary gland or colon.

MEC expression was also detected in epithelial cells. As illustrated in FIG. 3D, MEC mRNA was expressed in bronchus-associated epithelial cells and mammary gland epithelial cells but not in HL-60 promyeloid cells, human umbilical vein endothelial cells, or in human fibroblastic cells. To confirm epithelial cell-specific expression of MEC in vivo, laser capture microdissection (Emmert-Buck, M. R. et al., *Science* 274:998 (1996)) was used to capture epithelial and non-epithelial cells from human colon and salivary gland. The isolated cells were analyzed for the presence of MEC mRNA by low cycle RT-PCR followed by Southern blot analysis. As illustrated in FIG. 3E, captured epithelial cells from the colon and salivary gland expressed much higher MEC mRNA than adjacent soft tissues.

The results of the studies described herein demonstrate that MEC is a novel epithelial cell-expressed chemokine ligand for CCR10 and CCR3 with a unique pattern of tissue expression. Chemokines can modulate tissue physiology at multiple levels, including regulation of cell proliferation and differentiation, as well as modulation of adhesion, locomotion, and chemotaxis. Furthermore, MEC can participate in the physiology of mucosal tissues. For example, the results described herein together with the demonstrated presence of CCR10 mRNA in Peyer's patches, colon, and stomach (Jarmin, D. I. et al., *J. Immunol.* 164:3460 (2000); Homey, B. et al., *J. Immunol.* 164:3465 (2000)) is indicative of the coordinate presence of MEC and CCR10$^+$ cells in these mucosal sites. MEC and CTACK have distinctive patterns of expression and are further distinguished by their capacities to attract cells via CCR3. MEC, but not CTACK, stimulated the migration of CCR3 transfectants as well as eosinophils. Thus, MEC/CCR3 interactions can mediate recruitment of eosinophils and/or CCR3$^+$ T cells into mucosal tissues, including trachea and bronchi.

The results described herein are indicative that MEC plays a role in the recruitment and/or microenvironmental localization of specialized CCR10-expressing memory and effector lymphocyte subsets. For example, the high levels of MEC expression in salivary glands can induce recruitment of a population of CLA$^+$ lymphocytes to this site, as the buccal mucosa is known to be a site of localization of CLA$^+$ T cells (Vigneswaran, N. et al., *J. Oral Pathol. Med.* 20:337 (1991); Walton, L. J. et al., *J. Oral Pathol. Med.* 26:402 (1997)).

In conclusion, its unique pattern of mucosal epithelial expression and of chemokine receptor usage is indicative that MEC plays important roles in the physiology and pathophysiology of mucosal tissues.

Example 2

MEC is a Chemoattractant for IgA Antibody-secreting Cells

Materials and Methods

Mice

Female C57BL/6 mice were obtained from Jackson Laboratory (Bar Harbor, Me.). For analysis of cells derived from the spleen, Peyer's patch, mesenteric lymph node (MLN), asthmatic lung and the lamina propria of the small intestine, the mice were between six and eight weeks old. For analysis of cells isolated from salivary gland lymph nodes (SGLN) and tracheo-bronchial lymph nodes (TBLN), cells were obtained from six-month old mice as mice of this age had more IgA antibody-secreting cells associated with these sites.

Isolation of Cells from Mouse Tissue

Mice were sacrificed by $CO_2$ inhalation and the following tissues were removed: spleen, Peyer's patch, mesenteric lymph node, asthmatic lung, salivary gland lymph nodes (SGLN) and tracheo-bronchial lymph nodes (TBLN). These tissues were minced using scissors and single cell suspensions were obtained using mechanical dispersion through wire mesh. Red blood cells were lysed by hypotonic lysis and the remaining cells were allowed to recover at tissue culture conditions for an hour prior to being used.

Isolation of Lamina Propria Lymphocytes

Lamina propria lymphocytes (LPL) were isolated from normal murine small intestine as described (L. Lefrancois and N. Lycke. Isolation of Mouse Small Intestinal Intraepithelial Lymphocytes, Peyer's Patch, and Lamina Propria Cells. In *Current Protocols in Immunology*, 3.19.1–3.19.16. Edited by J. E. Coligan, A. M. Kruisbeek, D. H. Margulies, E. M. Shevach, and W. Strober. John Wiley & Sons, New York (1994)). Briefly, Peyer's patches were removed from 4–5 small intestines, the intestines were cut open longitudinally and then cut into short 5 mm segments. This segmented tissue was washed 3 times in $Ca^{2+}/Mg^{2+}$-free HBSS supplemented with 2% FCS and 15 mM HEPES. Epithelial cells and intraepithelial lymphocytes were removed by 5–6 vigorous washings in the same medium supplemented with 5 mM EDTA until no more shedding occurred. The segmented intestines were then washed twice in RPMI-1640 with 10% FCS and 15 mM HEPES. LPL were isolated by shaking the intestinal pieces 2–3 times for about 40 minutes in the RPMI medium supplemented with 300 U/mL of collagenase CLS-3 (Worthington Biochemical). LPL were allowed to recover in cRPMI in a $CO_2$ incubator for about 2 hours prior to analysis.

Induction of Asthma in Mice

Female C57BL/6 mice were primed by intraperitoneal injection of $1 \times 10^8$ sheep red blood cells. Two weeks later, the mice were challenged intratracheally with $5 \times 10^8$ sheep red blood cells. Three days later, the mice were sacrificed and total whole lung lymphocytes were subjected to analysis.

Chemotaxis Assay

Chemotaxis assays were performed as described herein. Briefly, two million cells which were isolated from particular mouse tissues were added to the top chamber of a 24 well TRANSWELL plate containing a TRANSWELL insert having a 5 μm pore size. Cells were exposed to medium (basal) or medium containing various concentrations of chemokines including human SDF-1 (hSDF-1), human MEC (hMEC) and mouse MEC (mMEC). Chemokines were obtained from R&D Systems (Minneapolis, Minn.) and were used at optimal concentrations, as determined by titration of the chemokine on splenocytes. After a two-hour incubation period, the antibody-secreting cells in the input cells and in the population that migrated to the bottom chamber were quantified by ELISPOT analysis.

ELISPOT Assay

IgA antibody-secreting cells, IgG antibody-secreting cells and IgM antibody-secreting cells were identified by conventional ELISPOT analysis. Briefly, nitrocellulose 96 well plates (Multiscreen 96 well filtration plate, Millipore, Bedford, Mass.) were incubated overnight with either goat-anti-mouse-IgA-specific polyclonal antibodies, goat-anti-mouse-IgG-specific polyclonal antibodies or goat-anti-mouse-IgM-specific polyclonal antibodies (Kirkegaard and Perry, Gaithersburg, Md.). Cells to be tested were then incubated in the antibody-coated wells overnight, after which the cells were washed off with phosphate-buffered saline (PBS). The nitrocellulose 96 well plates were then incubated with HRP-conjugated goat-anti-mouse-IgA, IgG or IgM antibodies for at least an hour at 37° C. The nitrocellulose 96 well plates were then washed with PBS and incubated for 15–20 minutes with the detection substrate, 3amino-9-ethylcarbazole. The number of antibody-secreting cells was counted using a dissecting microscope.

For the chemotaxis assays, percent migration is the number of IgA antibody-secreting cells which migrated in the presence of chemokine (either hSDF-1, hMEC or mMEC) divided by the number of IgA antibody-secreting cells in the input cell population (determined using a separate ELISPOT assay), displayed as a percentage.

Results and Discussion

MEC is a Chemoattractant for IgA Antibody-secreting Cells

IgA antibody-secreting cells from a variety of tissues exhibit chemotaxis to MEC. As depicted in FIGS. 10 and 11, IgA antibody-secreting cells (IgA ASC) from mouse spleens exhibited chemotaxis to human MEC (hMEC) (FIGS. 10 and 11) and mouse MEC (mMEC) (FIG. 11) in a dose-dependent manner (FIG. 10). Under the conditions of the in vitro chemotaxis assay, the optimal concentration of hMEC that induced chemotaxis of IgA antibody-secreting cells from mouse spleens was 250 nM. In contrast, IgG antibody-secreting cells and IgM antibody-secreting cells from the spleen failed to exhibit chemotaxis to MEC.

Analysis of IgA antibody-secreting cells from other mucosal lymphoid and effector sites also demonstrated MEC-induced chemotaxis. ELISPOT analysis revealed that IgA antibody-secreting cells were present in a variety of mouse tissues, including Peyer's patch, mesenteric lymph node (MLN), spleen, salivary gland lymph nodes (SG-LN), tracheo-bronchial lymph nodes (TB-LN) and iliac (the lymph node draining the genital tract) (FIG. 12). Human MEC and SDF-1 induced chemotaxis of IgA antibody-secreting cells from Peyer's patches, mesenteric lymph node (MLN), spleen, salivary gland lymph nodes (SG-LN) and tracheo-bronchial lymph nodes (TB-LN) in in vitro chemotaxis assays (FIG. 13) and IgA antibody-secreting cells from the lamina propria of the small intestine exhibited chemotaxis to MEC under the conditions tested in the in vitro chemotaxis assay. In addition, IgA antibody-secreting cells from asthmatic lung tissue also exhibited chemotaxis to MEC (FIG. 14), demonstrating that MEC can recruit IgA antibody-secreting cells to sites of mucosal inflammation.

IgA is secreted by plasmablasts and plasma cells at the epithelial layer of mucosal tissues and provides protection against pathogen entry through mucosal tissue. Thus, MEC, and agents which modulate (promote or inhibit) the binding of MEC to receptors (e.g., CCR3, CCR10) expressed on IgA antibody-secreting cells, can induce or modulate recruitment of IgA antibody-secreting cells to mucosal tissues.

The results of the studies described herein demonstrate that MEC can modulate the function (e.g., chemotaxis, locomotion, proliferation, differentiation) of lymphoid cells, such as memory and effector lymphoid cells including antibody-secreting cells (e.g., IgA antibody-secreting cells) and memory and/or effector T cells (e.g, TH1, TH2, TR1).

The results of the studies described herein clearly demonstrate the importance of MEC in the immuno-physiology of mucosal tissues.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of identifying an agent which inhibits the binding of a mammalian MEC to a mammalian C—C chemokine receptor 3 (CCR3) comprising:
   a) combining:
      i) an agent to be tested;
      ii) a composition comprising a mammalian CCR3 or a MEC-binding variant thereof; and
      iii) a mammalian MEC or a CCR3-binding variant thereof, under conditions suitable for binding of said MEC or CCR3-binding variant thereof to said CCR3 or MEC-binding variant thereof; and
   b) detecting or measuring the formation of a complex between said MEC or CCR3-binding variant thereof and said CCR3 or MEC-binding variant thereof, wherein inhibition of complex formation by the agent is indicative that the agent is an inhibitor, and
wherein said mammalian CCR3 or MEC-binding variant thereof is selected from the group consisting of:
   A) a polypeptide comprising an amino acid sequence that has at least about 90% amino acid sequence identity with SEQ ID NO:16 and binds MEC; and
   B) a MEC-binding fragment of A); and
said mammalian MEC or CCR3-binding variant thereof is selected from the group consisting of:
   1) a polypeptide comprising an amino acid sequence that has at least about 90% amino acid sequence identity with SEQ ID NO:2 and binds CCR3; and
   2) a CCR3-binding fragment of 1).

2. The method of claim 1, wherein said mammalian MEC or CCR3-binding variant thereof is labeled with a detectable label.

3. The method of claim 2, wherein said label is selected from the group consisting of a radioisotope, an epitope label, an affinity label, a spin label, an enzyme label, a fluorescent group and a chemiluminescent group.

4. The method of claim 1 wherein said composition comprising a mammalian CCR3 or MEC-binding variant thereof is a cell that expresses a human CCR3 or MEC-binding variant thereof.

5. The method of claim 4 wherein said cell is an eosinophil.

6. The method of claim 4 wherein said cell is a recombinant host cell.

7. The method of claim 1 wherein said composition comprising a mammalian CCR3 or MEC-binding variant thereof is a membrane preparation of a cell that expresses a mammalian CCR3 or MEC-binding variant thereof.

8. The method of claim 1 wherein said composition comprising a mammalian CCR3 or MEC-binding variant thereof comprises a MEC-binding variant that is a fusion protein comprising a first moiety and a second moiety,
   wherein said first moiety is a polypeptide that has at least about 90% amino acid sequence identity with SEQ ID NO:16 and binds MEC or a MEC-binding fragment thereof.

9. The method of claim 8 wherein said second moiety comprises an affinity ligand.

10. The method of claim 9 wherein said affinity ligand is selected from the group consisting of an enzyme, an antigen, an epitope tag and a binding domain.

11. The method of claim 10 wherein said affinity ligand is an epitope tag.

12. The method of claim 11 wherein said epitope tag is a hemagglutinin epitope.

13. The method of claim 1 wherein said mammalian CCR3 or MEC-binding variant thereof is a recombinant protein.

14. The method of claim 1 wherein said mammalian CCR3 or MEC-binding variant thereof is a naturally occurring mammalian CCR3.

15. The method of claim 14 wherein said naturally occurring mammalian CCR3 is a naturally occurring human CCR3.

16. The method of claim 1 wherein said composition comprising a mammalian MEC or CCR3-binding variant thereof comprises a CCR3-binding variant that is a fusion protein comprising a first moiety and a second moiety,
   wherein said first moiety is a polypeptide that has at least about 90% amino acid sequence identity with SEQ ID NO:2 and binds CCR3 or a CCR3-binding fragment thereof.

17. The method of claim 16 wherein said second moiety comprises an affinity ligand.

18. The method of claim 17 wherein said affinity ligand is selected from the group consisting of an enzyme, an antigen, an epitope tag and a binding domain.

19. The method of claim 1 wherein said mammalian MEC or CCR3-binding variant thereof is a naturally occurring mammalian MEC.

20. The method of claim 19 wherein said naturally occurring mammalian MEC is a naturally occurring human MEC.

21. The method of claim 1 wherein said composition comprising a mammalian CCR3 or MEC-binding variant thereof is a paramagnetic proteoliposome that comprises said mammalian CCR3 or MEC-binding variant thereof.

22. The method of claim 1 wherein said mammalian CCR3 or MEC-binding variant thereof is labeled with a detectable label.

23. The method of claim 22 wherein said detectable label is selected from the group consisting of a radioisotope, an epitope label, an affinity label, a spin label, an enzyme label, a fluorescent group and a chemiluminescent group.

24. The method of claim 1 wherein formation of a complex between said MEC or CCR3-binding variant thereof and said CCR3 or MEC-binding variant thereof is detected or measured by surface plasmon resonance.

25. The method of claim 1 wherein said agent is selected from the group consisting of a protein, a peptide, a peptidomimetic, a small organic molecule and a nucleic acid.

26. The method of claim 4 wherein said cell is a leukocyte.

* * * * *

UNITED STATES PATENT AND TRADEMARK OFFICE
CERTIFICATE OF CORRECTION

PATENT NO. : 6,692,922 B2
DATED : February 17, 2004
INVENTOR(S) : Butcher et al.

It is certified that error appears in the above-identified patent and that said Letters Patent is hereby corrected as shown below:

<u>Title page,</u>
Item [*] Notice, should read -- delete the phrase "by 78" and insert -- by 0 days --

Signed and Sealed this

Fourteenth Day of June, 2005

JON W. DUDAS
*Director of the United States Patent and Trademark Office*